US012797385B2

(12) United States Patent
He et al.

(10) Patent No.: US 12,797,385 B2
(45) Date of Patent: Nov. 17, 2026

(54) AROMATIC HETEROCYCLIC COMPOUND, PHARMACEUTICAL COMPOSITION CONTAINING THE SAME, AND USE THEREOF

(71) Applicant: HANG ZHOU YUHONG PHARMATECH CO., LTD., Hangzhou (CN)

(72) Inventors: Qiaojun He, Hangzhou (CN); Qinjie Weng, Hangzhou (CN); Binhui Chen, Hangzhou (CN); Jun Mo, Hangzhou (CN); Wenwen Nie, Hangzhou (CN); Qing Lin, Hangzhou (CN); Minjie Ge, Hangzhou (CN)

(73) Assignee: HANG ZHOU YUHONG PHARMATECH CO., LTD., Hangzhou (CN)

( * ) Notice: Subject to any disclaimer, the term of this patent is extended or adjusted under 35 U.S.C. 154(b) by 325 days.

(21) Appl. No.: 18/685,859

(22) PCT Filed: Aug. 24, 2022

(86) PCT No.: PCT/CN2022/114443
§ 371 (c)(1),
(2) Date: Feb. 22, 2024

(87) PCT Pub. No.: WO2023/025182
PCT Pub. Date: Mar. 2, 2023

(65) Prior Publication Data

US 2026/0158031 A1 Jun. 11, 2026

(30) Foreign Application Priority Data

Aug. 25, 2021 (CN) ........................ 202110984399.1

(51) Int. Cl.
*A61K 31/4985* (2006.01)
*A61K 31/437* (2006.01)
*A61K 31/519* (2006.01)
*A61K 31/551* (2006.01)
*A61P 37/06* (2006.01)
*C07D 519/00* (2006.01)

(52) U.S. Cl.
CPC ........ *A61K 31/4985* (2013.01); *A61K 31/437* (2013.01); *A61K 31/519* (2013.01); *A61K 31/551* (2013.01); *A61P 37/06* (2018.01); *C07D 519/00* (2013.01)

(58) Field of Classification Search
None
See application file for complete search history.

(56) References Cited

FOREIGN PATENT DOCUMENTS

| | | | | |
|---|---|---|---|---|
| CN | 106061973 A | | 10/2016 | |
| CN | 106146482 A | | 11/2016 | |
| CN | 109867676 A | | 6/2019 | |
| CN | 112165944 A | | 1/2021 | |
| CN | 113429427 A | | 9/2021 | |
| WO | 2013085802 A1 | | 6/2013 | |
| WO | WO-2014075318 A1 | * | 5/2014 | ............. A61P 35/02 |
| WO | 2021190616 A1 | | 9/2021 | |
| WO | 2023025182 A1 | | 3/2023 | |

OTHER PUBLICATIONS

PCT/CN2022/114443—International Search Report and Written Opinion mailed on Nov. 16, 2022, 16 pages.

* cited by examiner

*Primary Examiner* — Sarah Pihonak
*Assistant Examiner* — Donna M Nestor
(74) *Attorney, Agent, or Firm* — Getech Law LLC; Jun Ye

(57) ABSTRACT

The present invention discloses a compound of formula I, a composition including the same and use thereof, wherein A, X, Y, L, M and W are as defined herein. The compound disclosed in the present invention can be used for treating diseases related to over-activation or over-expression of JAK3 kinase, such as autoimmune diseases, lung injury, and organ transplant rejection. In vitro experiments show that this series of compounds have a good inhibitory activity on the JAK3 kinase and have good application prospects in the field of medicine.

5 Claims, 2 Drawing Sheets

Note: compared with the model group, *P < 0.05, **P < 0.01

AROMATIC HETEROCYCLIC COMPOUND, PHARMACEUTICAL COMPOSITION CONTAINING THE SAME, AND USE THEREOF

CROSS REFERENCE OF RELATED APPLICATION

The present application is a 371 of international Application PCT/CN2022/114443, filed Aug. 24, 2022, which claims priority to Chinese Patent Application No. 202110984399.1 filed Aug. 25, 2021. The contents of the applications are incorporated herein by reference in their entireties.

FIELD OF TECHNOLOGY

The present invention belongs to the technical field of medicine and relates to an aromatic heterocyclic compound with one or more Janus kinase (JAK) inhibitory activities. The present invention further relates to a pharmaceutical composition in which the compound is used as an active ingredient, and use thereof.

BACKGROUND

Janus kinase (JAK) is a cytoplasmic tyrosine protein kinase responsible for transducing many inflammation-related cytokine signals from cytokine membrane receptors to STAT transcription factors. Abnormalities in JAK/STAT signal transduction are associated with many diseases, including those involving immune inflammation such as organ transplant rejection, multiple sclerosis, rheumatoid arthritis, type I diabetes, lupus, psoriasis, asthma, food allergy, atopic dermatitis, rhinitis and rash; and they have also been reported to be closely related to the occurrence and development of solid and blood malignant tumors and myeloproliferative disorders (including lung cancer, breast cancer, chronic spontaneous myelofibrosis, polycythemia, essential thrombocythemia, etc.).

The first-generation JAK inhibitors exhibit broad inhibitory activity against JAK kinase family subtypes and have good therapeutic effects in inflammatory diseases, tumors, and blood diseases. However, because the JAK kinase family widely mediates the signaling of a variety of cytokines, the functions of many of which are closely related to the normal physiological functions of an organism, the side effects of Pan-JAK inhibitors shown in clinical applications include anemia, neutrophilic granulocytopenia, infection, lymphopenia, hyperlipidaemia, etc. Among them, Tofacitinib has the risk of infection and thrombus leading to a black box warning issued by the FDA; and Ruxolitinib also has received a black box warning due to platelet abnormality.

The second-generation selective JAK inhibitors usually mainly act on specific subtypes of the JAK family, which can reduce the occurrence of adverse events while controlling the development of the diseases. The currently marketed JAK selective inhibitors include a JAK2 inhibitor Fedratinib available from Celgene, a JAK1 selective inhibitor upadacitinib available from AbbVie, and a JAK1 inhibitor Filgotinib available from Gilead. JAK1 inhibitors have outstanding therapeutic effects in treating immune diseases, but they still pertain to broad-spectrum immunosuppressants with limited selectivity and heightened safety risks. The marketed JAK1 inhibitors Upadacitinib and Baricitinib both have black box warnings, and the marketed JAK2 inhibitor Fedratinib also has serious adverse responses such as Wernicke's encephalopathy and orbital inflammatory responses.

JAK3 is mainly expressed in various hematopoietic tissue cells, including bone marrow cells, thymocytes, NK cells, activated B lymphocytes, T lymphocytes, etc. Its physiological effects are only derived from the signal transduction process of a common y cytokine receptor family, therefore it acts on the JAK3 kinase with high selectivity, which can avoid unnecessary side effects. Therefore, improving the activity and selectivity of JAK3 kinase inhibitors can further improve the clinical use effect of the JAK3 kinase inhibitors, which has significant clinical advantages compared with currently clinically applied Pan-JAK inhibitors and selective JAK1 and JAK2 inhibitors. Currently, among highly selective JAK3 inhibitors, only PF-06651600 has entered the late clinical development stage and has been designated as a breakthrough therapy by the FDA for the treatment of alopecia areata, other JAK3 kinase inhibitors are still in the academic research and early clinical development stages. PF-06651600 also irreversibly inhibits a TEC kinase family (BTK, BMX, ITK, RLK, TEC). The therapeutic effect of PF-06651600 on autoimmune diseases largely comes from its inhibition on the TEC kinase family. The data of Clinical Phase 2a indicates that adverse events occurred during treatment with PF-06651600 are infection and skin and subcutaneous tissue diseases. Meanwhile, many patients have developed symptoms of thrombocytopenia, which may be related to the inhibitory effect of PF-06651600 on the TEC kinase family. (Robinson M. F., Damjanov N., Stamenkovic B. et al. Efficacy and Safety of PF-06651600 (Ritlecitinib), a Novel JAK3/TEC Inhibitor, in Patients With Moderate-to-Severe Rheumatoid Arthritis and an Inadequate Response to Methotrexate. *Arthritis Rheumatol.* 2020, 72 (10), 1621-1631.)

In view of the above, improving the activity and selectivity of JAK inhibitors against the JAK3 kinase and reducing off-target effects are of great significance for solving the poor therapeutic effects and safety issues that arise during the current use of JAK inhibitors.

SUMMARY

The present invention provides an aromatic heterocyclic compound with good Janus kinase (JAK) inhibitory activity, which has both good activity and selectivity for JAK3 kinase.

The present invention provides a composition and formulation including the aforementioned aromatic heterocyclic compound.

Meanwhile, the present invention further provides use of the aforementioned compound, composition or formulation in the preparation of a drug for preventing or treating a disease caused by a JAK-STAT signaling pathway abnormality. The compound of the present invention can be used as a JAK kinase inhibitor for treating and preventing clinical applications related to abnormal activity of these kinases, including autoimmune diseases, inflammatory diseases and other diseases.

The present invention adopts the following technical solutions.

The present invention provides a compound having a structure of general formula I, an optical isomer thereof, a deuterated compound thereof or a pharmaceutically acceptable salt thereof:

I

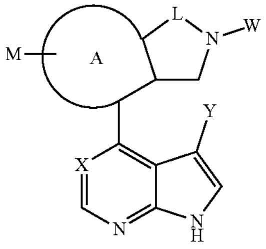

wherein:

a ring A is a five-membered aromatic heterocyclic ring containing 1-3 heteroatoms selected from O, N, and S;

M is a substituent of the ring A, and the M is selected from deletion, hydrogen, $C_1$-$C_4$ alkanoyl, $C_1$-$C_4$ alkyl, deuterated $C_1$-$C_4$ alkyl, $C_1$-$C_4$ alkanesulfonyl or $C_4$-$C_6$ heterocycloalkyl, wherein the $C_4$-$C_6$ heterocycloalkyl contains 1 heteroatom selected from O, N, S;

L is selected from

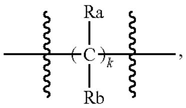,

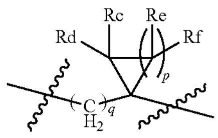

or

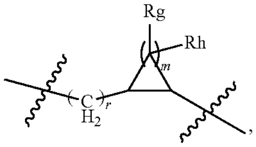, wherein $R_a$, $R_b$, $R_c$, $R_d$, $R_e$, $R_f$, $R_g$, and $R_h$ are each independently selected from hydrogen, cyano, hydroxyl, halogen, $C_1$-$C_4$ alkoxy, $C_1$-$C_4$ alkyl, monosubstituted $C_1$-$C_4$ alkyl, $C_1$-$C_4$ alkanoyl, $C_1$-$C_4$ alkylthio, $C_1$-$C_4$ alkanesulfonyl, the substituent in the "monosubstituted $C_1$-$C_4$ alkyl" are selected from $C_1$-$C_3$ alkylthio, $C_1$-$C_3$ alkanesulfonyl, $C_1$-$C_3$ alkanoyl, halogen, and cyano; k is an integer of 1-5, q is an integer of 0-4, r is an integer of 0-3, p and m are each independently selected from an integer of 1-4; when k is greater than 1, that is, when L is an alkyl chain segment containing two or more C, $R_a$ or $R_b$ on different carbon atoms are the same or different (that is, $R_a$ on different carbon atoms can be different or the same, and $R_b$ on different carbon atoms can be the same or different, that is, $R_a$ on different carbon atoms are independent of each other, and $R_b$ on different carbon atoms are independent of each other); when p is greater than 1, $R_e$ or $R_f$ on different carbon atoms are the same or different (explanation is the same as above); and when m is greater than 1, $R_g$ or $R_h$ on different carbon atoms are the same or different, and the explanation is the same as above);

W is a covalent target head which refers to a chemical group that can form a covalent bond with a nucleophilic reagent, W is selected from

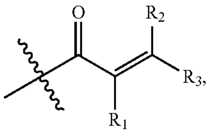,

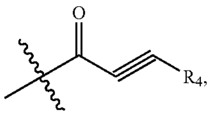,

-continued

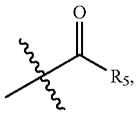,

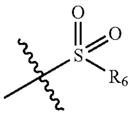

or a nitrile group; wherein $R_1$ and $R_2$ are each independently selected from hydrogen, deuterium, halogen, cyano, $C_1$-$C_4$ alkyl, halomethyl, $R_3$ is selected from hydrogen, deuterium, halogen, cyano, $C_1$-$C_4$ alkyl, halomethyl,

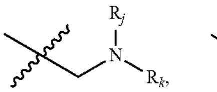,

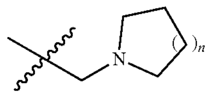

or

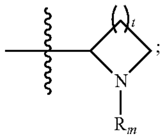;

n and t are each independently selected from an integer of 1-3; $R_4$, $R_j$, $R_k$ and $R_m$ are each independently selected from hydrogen or $C_1$-$C_4$ alkyl; $R_5$ is halomethyl; and $R_6$ is vinyl or halomethyl;

X is selected from N or CH; and Y is selected from hydrogen, $C_1$-$C_4$ alkyl or $C_1$-$C_4$ alkanoyl;

According to the compound of general formula (I), the present invention is preferably a compound of any of the following structures:

the ring A is a five-membered aromatic heterocyclic ring containing 1-3 heteroatoms selected from a N atom;

M is a substituent of the ring A, and M is selected from hydrogen, deuterated methyl, $C_1$-$C_4$ alkanoyl, $C_1$-$C_4$ alkyl or $C_4$-$C_6$ heterocycloalkyl, wherein the $C_4$-$C_6$ heterocycloalkyl contains 1 heteroatom, and the heteroatom is an oxygen atom;

L is selected from

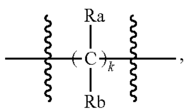,

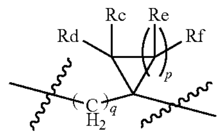

or

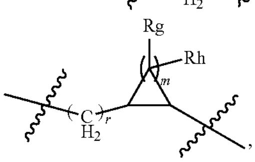, wherein $R_a$, $R_b$, $R_c$, $R_a$, $R_e$, $R_f$, $R_g$, and $R_h$ are each independently selected from hydrogen, $C_1$-$C_4$ alkyl, and monosubstituted $C_1$-$C_4$ alkyl, the substituent in the "monosubstituted $C_1$-$C_4$ alkyl" is selected from $C_1$-$C_3$ alkylthio, $C_1$-$C_3$ alkanesulfonyl, and cyano; k is an integer of 1-4, q is an integer of 0-3, r is an integer of 0-2, p is 1 or 2, and m is 3 or 4;

W is selected from

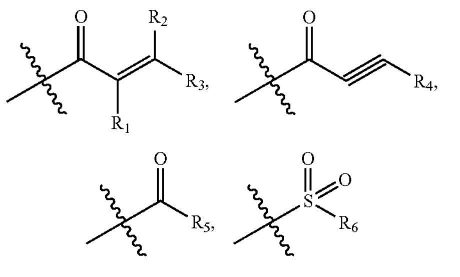

or a nitrile group; wherein $R_1$ and $R_2$ are each independently selected from hydrogen, deuterium, halogen, cyano, $C_1$-$C_4$ alkyl, $R_3$ is selected from hydrogen, deuterium, halogen, cyano, $C_1$-$C_4$ alkyl, halomethyl,

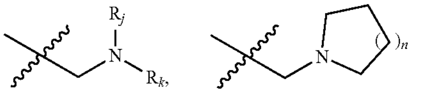

or

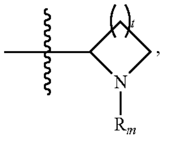

n and t are each independently selected from an integer of 1-3; $R_j$, $R_k$ and $R_m$ are each independently selected from hydrogen, methyl or ethyl; $R_4$ is selected from hydrogen or methyl; $R_5$ is halomethyl; and $R_6$ represents vinyl;

X is selected from N or CH; and Y is selected from hydrogen or $C_1$-$C_4$ alkanoyl;

The present invention more preferably has a structure of general formula II, or an optical isomer thereof, a deuterated compound thereof or a pharmaceutically acceptable salt thereof:

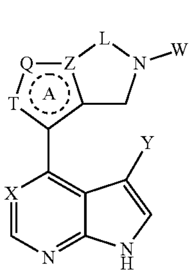

II wherein:

the ring A is a five-membered heterocyclic ring containing 2 double bonds; Z is N or C, Q is N or $NR_7$, Tis CH or N or $NR_8$, and when Z and T are N at the same time, Q is N; wherein $R_7$ and $R_5$ are independently hydrogen, deuterated methyl, $C_1$-$C_4$ alkanoyl, $C_1$-$C_4$ alkyl or $C_4$-$C_6$ heterocycloalkyl respectively, wherein the $C_4$-$C_6$ heterocycloalkyl contains 1 heteroatom, and the heteroatom is an oxygen atom.

L is selected from

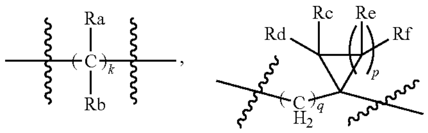

or

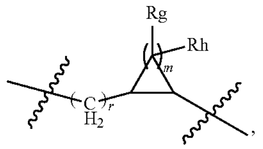

wherein $R_a$, $R_b$, $R_c$, $R_d$, $R_e$, $R_f$, $R_g$, and $R_h$ are each independently selected from hydrogen, $C_1$-$C_4$ alkyl, and monosubstituted $C_1$-$C_4$ alkyl, the substituent in the "monosubstituted $C_1$-$C_4$ alkyl" is selected from $C_1$-$C_3$ alkylthio, $C_1$-$C_3$ alkanesulfonyl, and cyano; k is an integer of 1-4, q is an integer of 0-3, r is an integer of 0-2, p is 1 or 2, and m is 3 or 4;

W is selected from

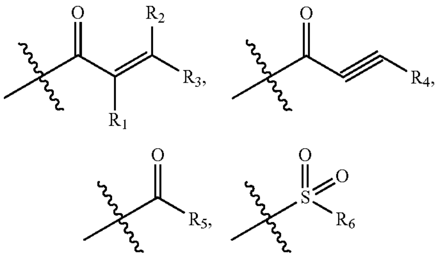

or a nitrile group; wherein $R_1$ and $R_2$ are each independently selected from hydrogen, deuterium, halogen, cyano, $C_1$-$C_4$ alkyl, $R_3$ is selected from hydrogen, deuterium, halogen, cyano, $C_1$-$C_4$ alkyl, halomethyl,

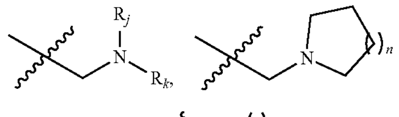

or

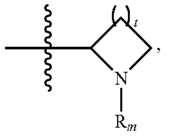

n and t are each independently selected from an integer of 1-3; $R_j$, $R_k$ and $R_m$ are each independently selected from hydrogen, methyl or ethyl; $R_4$ is selected from hydrogen or methyl; $R_5$ is halomethyl; and $R_6$ represents vinyl;

X is selected from N or CH; and Y is selected from hydrogen or $C_1$-$C_4$ alkanoyl;

The present invention more preferably has a structure of general formula III-1, III-2, III-3 or III-4, or an optical isomer thereof, a deuterated compound thereof or a pharmaceutically acceptable salt thereof:

III-1

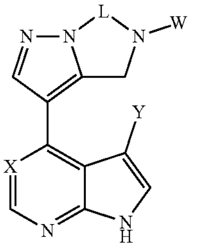

III-2

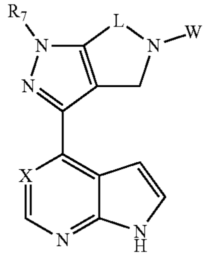

III-3

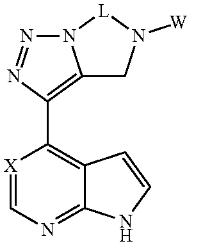

III-4

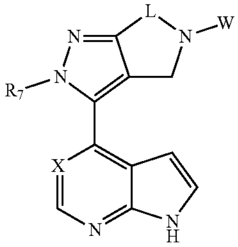

L is selected from

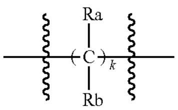,

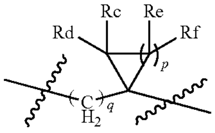

or

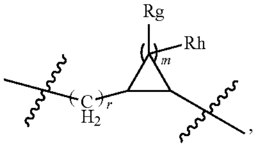, wherein $R_a$, $R_b$, $R_c$, $R_a$, $R_e$, $R_f$, $R_g$, and $R_h$ are each independently selected from hydrogen, $C_1$-$C_4$ alkyl, and monosubstituted $C_1$-$C_4$ alkyl, the substituent in the "monosubstituted $C_1$-$C_4$ alkyl" is selected from methylthio, methanesulfonyl, and cyano; k is an integer of 1-4, q is an integer of 0-3, r is an integer of 0-2, p is 1, and m is 3 or 4;

W is selected from

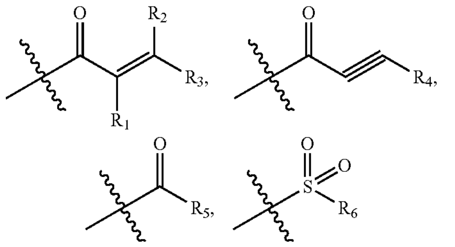

or a nitrile group; wherein $R_1$ is hydrogen, deuterium, halogen, cyano, or methyl, $R_2$ is hydrogen, deuterium, cyano or methyl, $R_3$ is hydrogen, deuterium, halogen, cyano, methyl, trifluoromethyl,

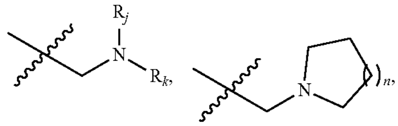

or

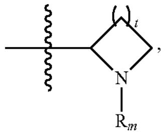, n and t are 2, $R_j$, $R_k$, and $R_m$ are methyl; $R_4$ is selected from hydrogen or methyl; $R_5$ is halomethyl; and $R_6$ represents vinyl;

X is selected from N or CH; and Y is selected from hydrogen or acetyl.

As a preference:

L is selected from

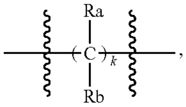,

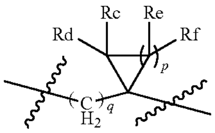

or

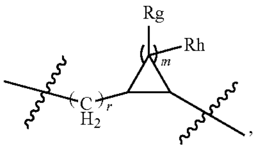, wherein: $R_a$ and $R_b$ are each independently selected from H, methyl, isopropyl, methylthio-substituted ethyl, and methanesulfonylethyl; $R_c$, $R_a$, $R_e$, and $R_f$ are each independently selected from H and methyl; $R_g$ and $R_h$ are each independently selected from H and methyl; k is 1, 2, 3, or 4, q is 1, r is 0, p is 1, and m is 3 or 4;

$R_7$ and $R_8$ are independently hydrogen, methyl, isopropyl, acetyl, deuterated methyl, $C_4$-$C_6$ heterocycloalkyl respectively, wherein the $C_4$-$C_6$ heterocycloalkyl contains 1 heteroatom, and the heteroatom is an oxygen atom.

As a specific preference:

the A ring is selected from a five-membered heterocyclic ring with two double bonds, and the hetero atoms are two adjacent N atoms; and preferably, the A ring is selected from a pyrazole ring.

In the general formula I,

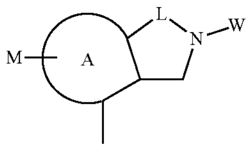
is selected from the following structures:
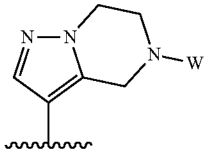 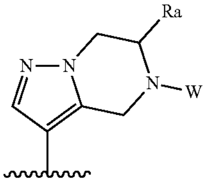
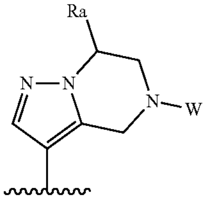 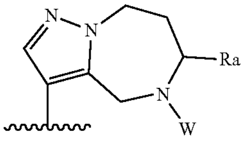
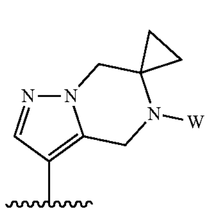 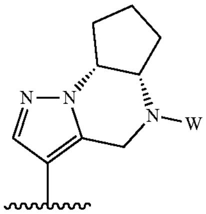
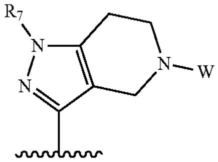 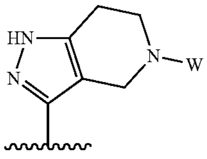
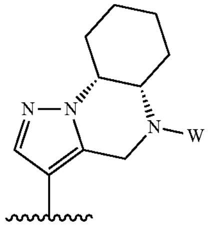 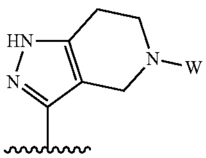
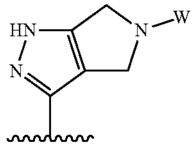 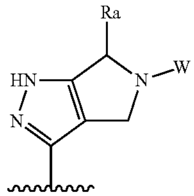
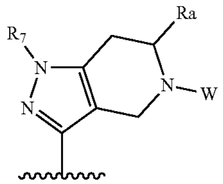 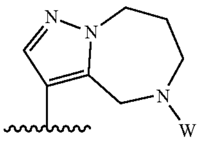
-continued
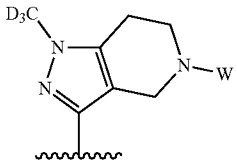
As a preference, the $R_a$ is preferably methyl, H, ethyl, isopropyl, methylthioethyl, or methanesulfonylethyl. The $R_7$ is preferably methyl, H, acetyl, or isopropyl.
As a preference, the W is preferably:
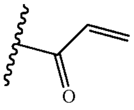 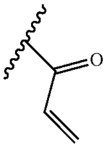 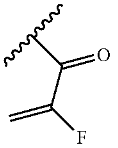
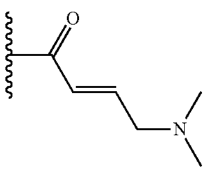 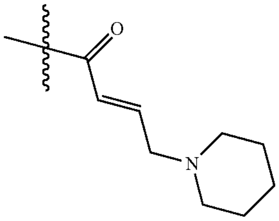
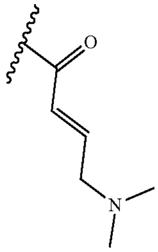 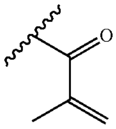 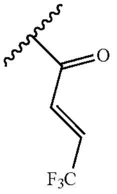
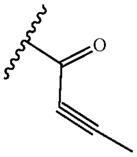 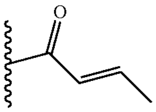 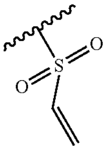
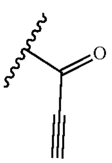 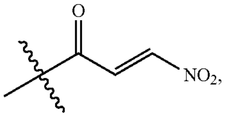, 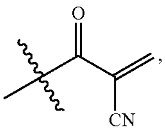,
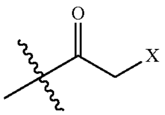
(X is fluorine, chlorine, bromine, or iodine),
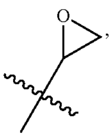 [SMILES: *C1CO1],

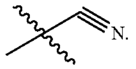

As a preference, the N adjacent to W in the general formula I is defined as N-1, and when there is a non-H substitution on the carbon atom adjacent to the N-1 in the L (for example, the substituent is methyl or isopropyl), the carbon atom has a chiral structure.

The present invention is further preferably a compound of any of the following structures:

YZ001001

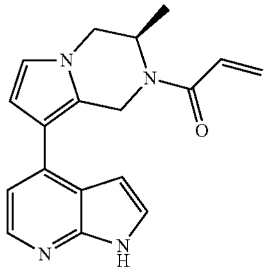

YZ001002

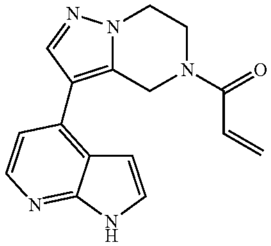

YZ001004

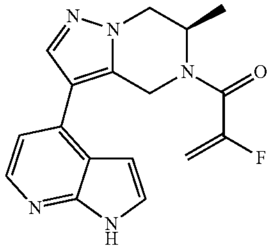

YZ001005

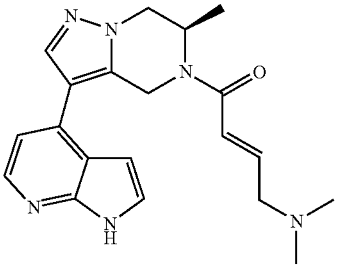

-continued

YZ001006

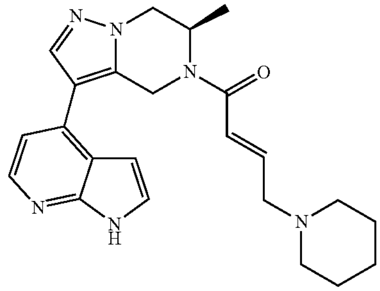

YZ001007

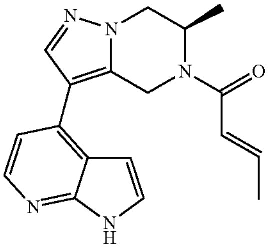

YZ001008

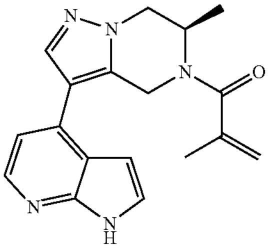

YZ001009

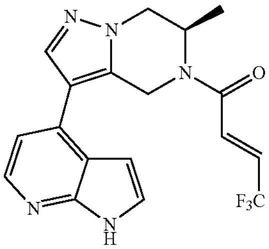

YZ001010

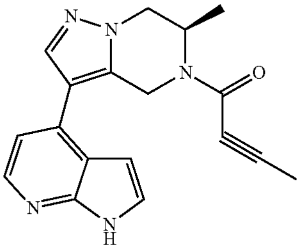

YZ001013

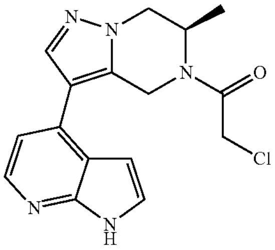

-continued
YZ001016
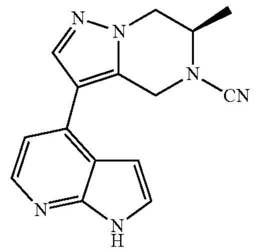
YZ001017
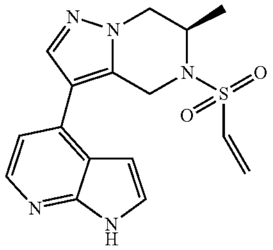
YZ001018
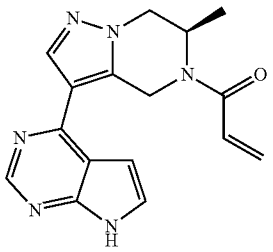
YZ001019
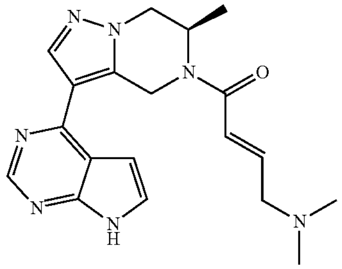
YZ001020
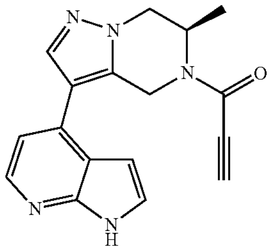
YZ001021
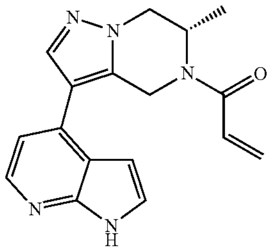
-continued
YZ001022
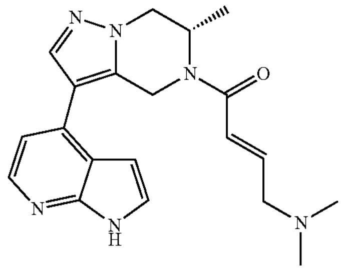
YZ001023
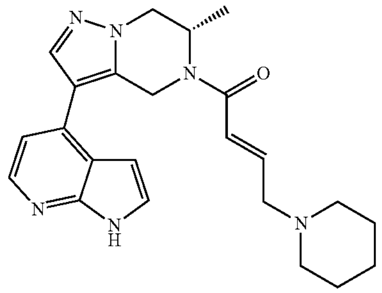
YZ001024
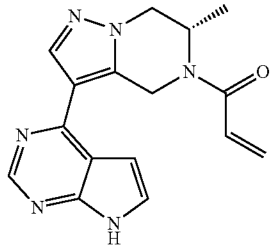
YZ001025
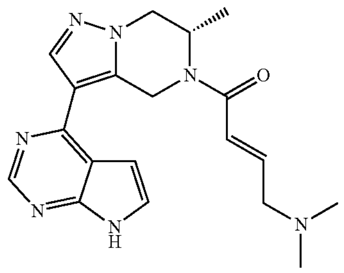
YZ001026
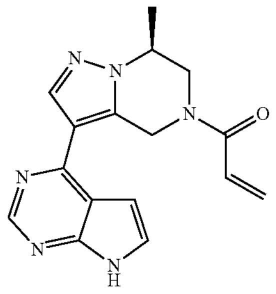

-continued
YZ001027
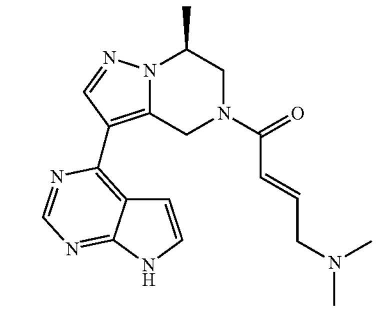
YZ001028
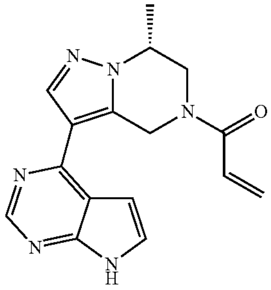
YZ001029
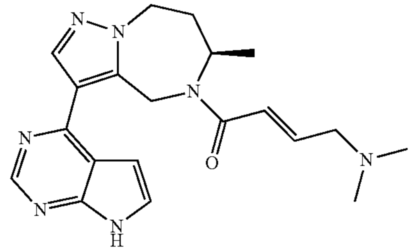
YZ001030
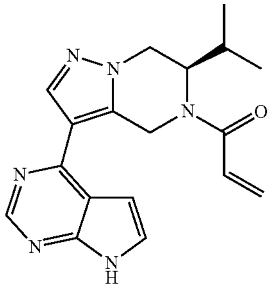
YZ001031
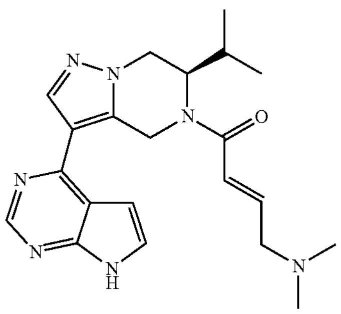
-continued
YZ001032
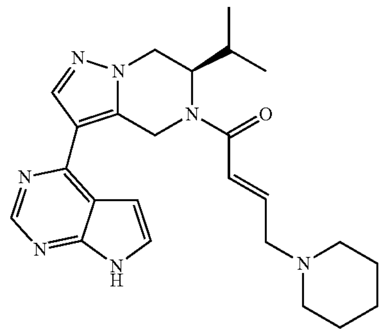
YZ001033
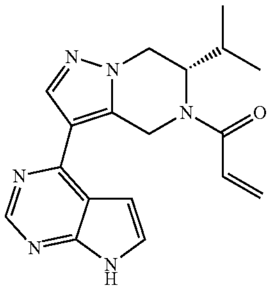
YZ001034
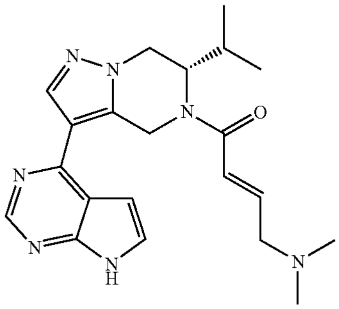
YZ001035
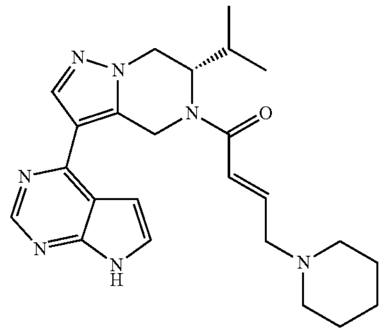
YZ001039
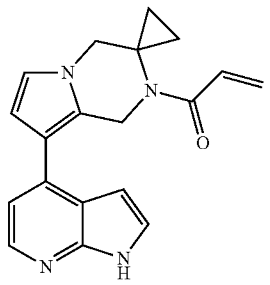

-continued
YZ001045
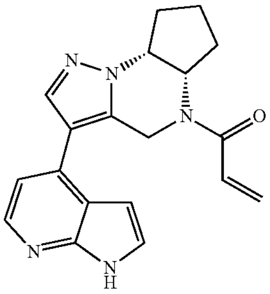
YZ001047
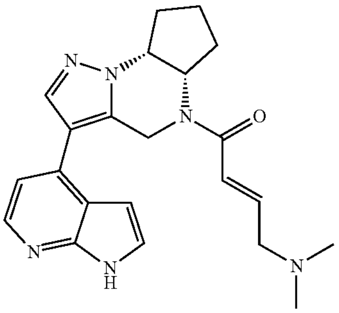
YZ001048
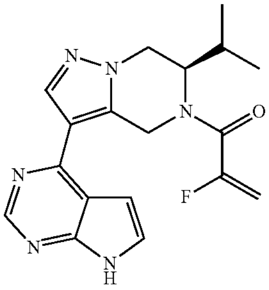
YZ001049
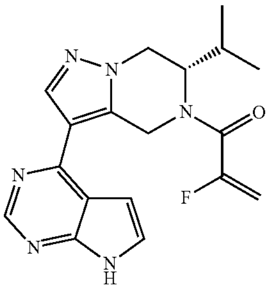
YZ001050
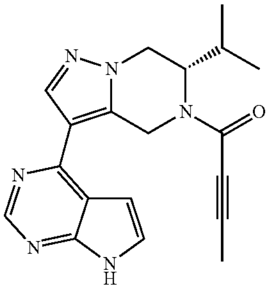
-continued
YZ001051
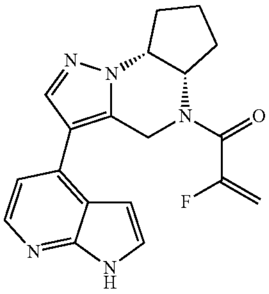
YZ001052
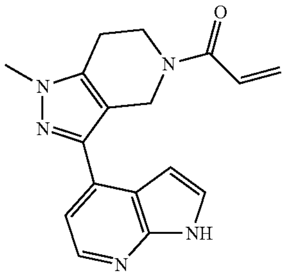
YZ001053
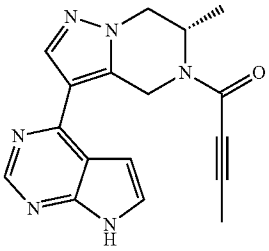
YZ001054
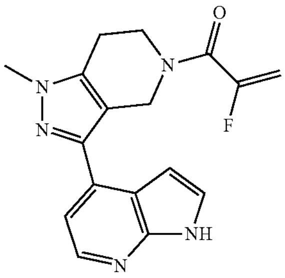
YZ001055
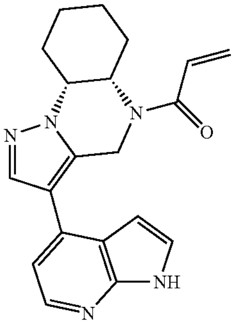

-continued
YZ001056
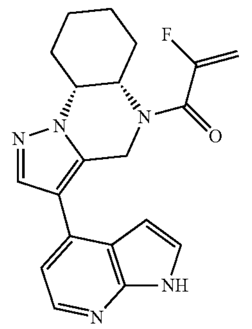
YZ001057
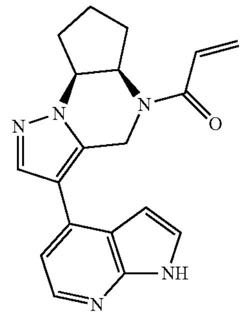
YZ001058
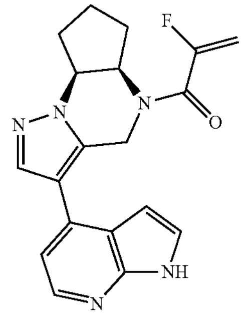
YZ001059
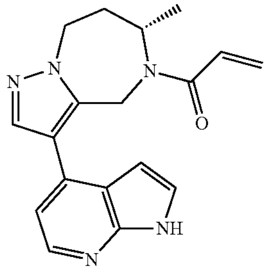
YZ001060
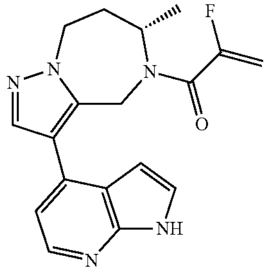
-continued
YZ001063
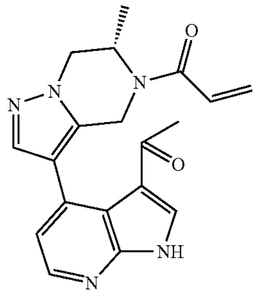
YZ001064
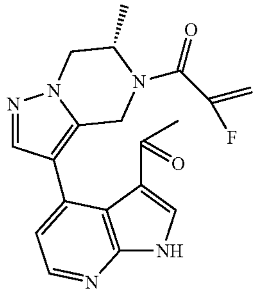
YZ001065
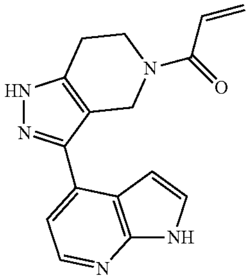
YZ001066
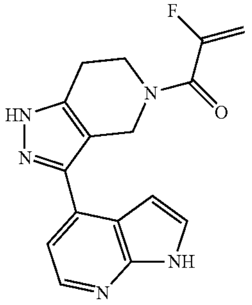
YZ001067
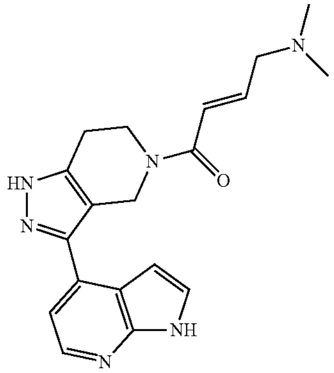

-continued
YZ001068
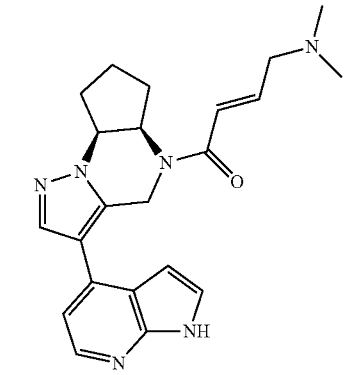
YZ001069
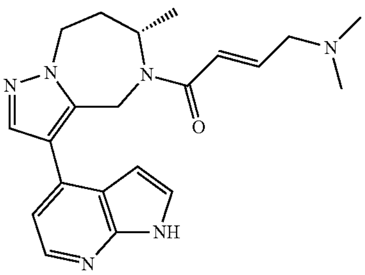
YZ001070
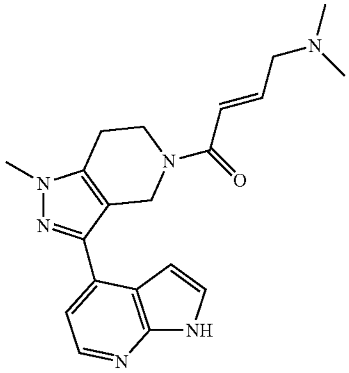
YZ001071
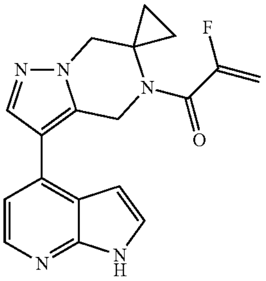
YZ001072
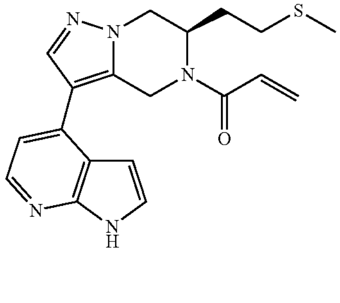
-continued
YZ001073
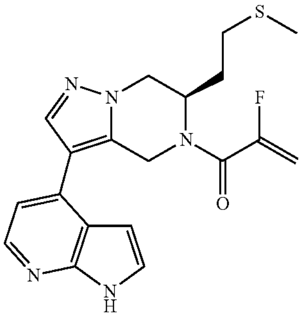
YZ001074
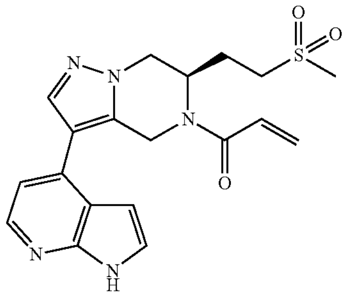
YZ001075
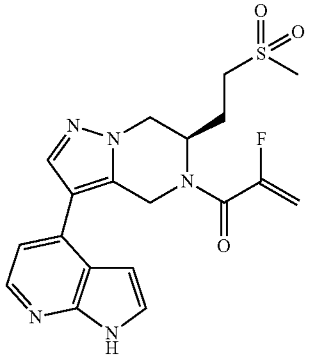
YZ001076
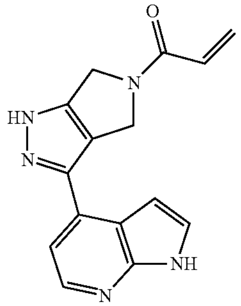
YZ001077
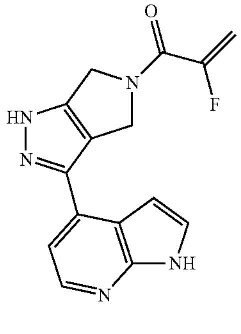

-continued
YZ001083
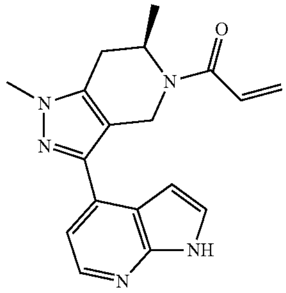
YZ001084
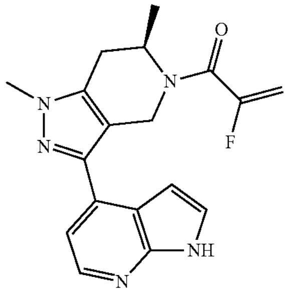
YZ001085
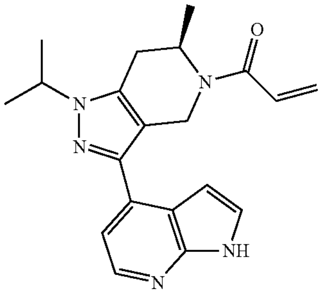
YZ001086
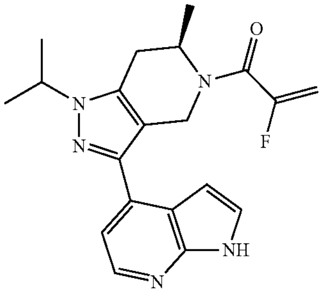
YZ001087
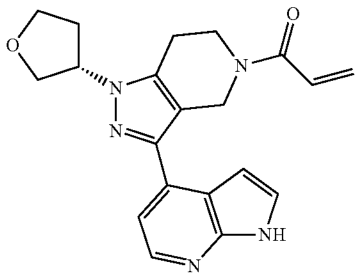
-continued
YZ001088
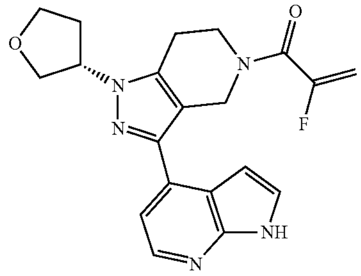
YZ001091
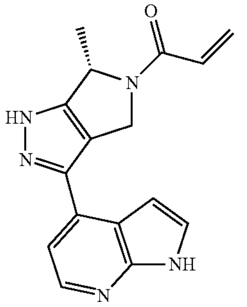
YZ001093
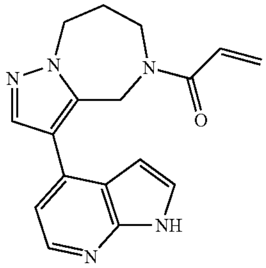
YZ001094
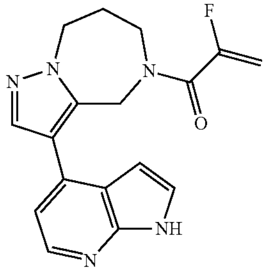
YZ001095
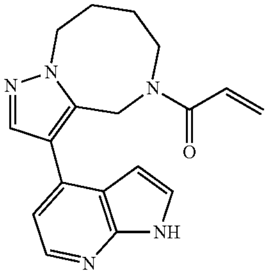

-continued
YZ001096
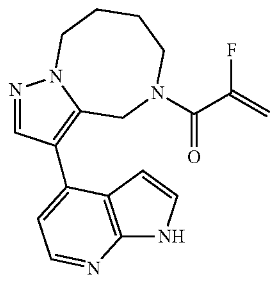
YZ001099
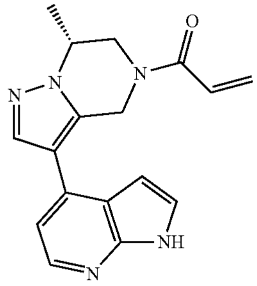
YZ001100
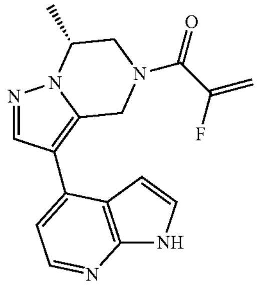
YZ001103
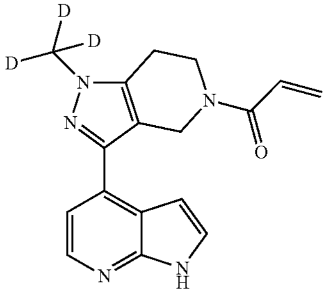
YZ001104
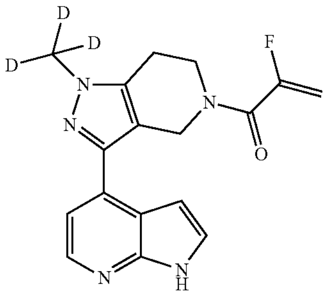
-continued
YZ001107
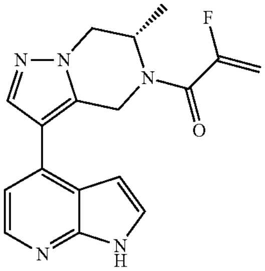
YZ001108
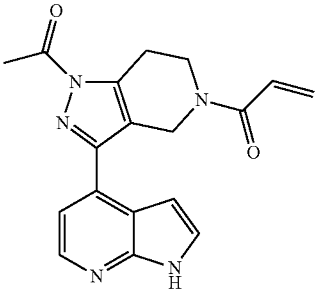
YZ001109
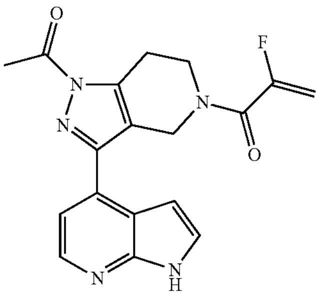
YZ001115
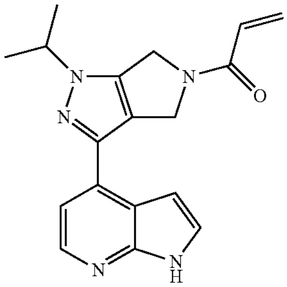
YZ001117
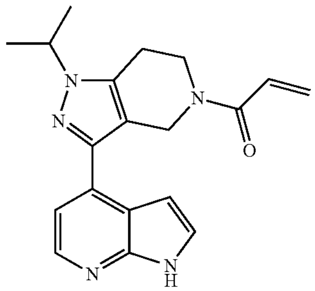

-continued

YZ001118

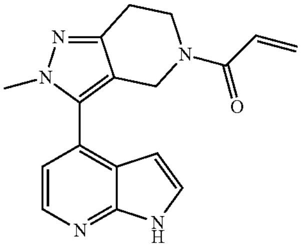

, or an optical isomer thereof, a deuterated compound thereof or a pharmaceutically acceptable salt thereof;

The present invention further provides a pharmaceutical composition including one or more of the aforementioned general formula I, general formula II, or general formulas III-1-III-4, or the aforementioned specific compounds.

Provided is a pharmaceutical formulation including at least one active component and one or more pharmaceutically acceptable carriers or excipients. The active component is selected from one or more of the aforementioned general formula I, general formula II, or general formulas III-1-III-4, or the aforementioned specific compounds, or optical isomers thereof, or deuterated compounds thereof or pharmaceutically acceptable salts thereof. The present invention provides use of the compound of general formula I, or an optical isomer thereof, a deuterated compound thereof or a pharmaceutically acceptable salt thereof in the preparation of a drug for preventing or treating a disease caused by a JAK-STAT signaling pathway abnormality. More preferably, provided is the use in a disease caused by over-activation or over-expression of JAK3 kinase. The disease includes but is not limited to an autoimmune disease and lung injury. The autoimmune disease refers to one or more of alopecia areata, lupus, multiple sclerosis, amyotrophic lateral sclerosis, rheumatic arthritis, type 1 diabetes, autoimmune hemolytic anemia, rheumatoid arthritis, psoriasis, complications caused by organ transplantation, atopic dermatitis, an autoimmune thyroid disease, ulcerative colitis, a Crohn's disease, a Sjogren's syndrome, systemic scleroderma, a mixed connective tissue disease, vitiligo, autoimmune kidney injury, autoimmune liver injury, and a chronic obstructive pulmonary disease.

As a preference, the disease caused by the JAK-STAT signaling pathway abnormality is lung injury, and the lung injury refers to radiation-induced lung injury and acute lung injury.

Definitions and Description: unless otherwise stated, the following terms and phrases used herein are intended to have the following meanings. A particular term or phrase should not be considered uncertain or unclear in the absence of a specific definition, but should be understood in its ordinary meaning. Where a trade name appears herein, it is intended to refer to its corresponding trade name or an active ingredient thereof.

The term "pharmaceutically acceptable" refers to those compounds, materials, compositions and/or dosage forms which, within the scope of sound medical judgment, are suitable for use in contact with the tissues of human and animals, without undue toxicity, irritation, allergic reactions, or other problems or complications, and are commensurate with a reasonable benefit/risk ratio.

The term "pharmaceutically acceptable salt" refers to a salt of the compound of the present invention, which is prepared from the compound having a specific substituent as discovered in the present invention and a relatively non-toxic acid or base. When the compound of the present invention contains a relatively acidic functional group, a base addition salt can be obtained by contacting the neutral form of such compounds with a sufficient amount of a base in a pure solution or a suitable inert solvent. A pharmaceutically acceptable base addition salt includes a sodium, potassium, calcium, ammonium, organic ammonia or magnesium salt, or the like salts. When the compound of the present invention contains a relatively basic functional group, an acid addition salt can be obtained by contacting the neutral form of such compounds with a sufficient amount of an acid in a pure solution or a suitable inert solvent. Examples of a pharmaceutically acceptable acid addition salt include inorganic acid salts, including, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydriodic acid, phosphorous acid, etc.; and organic acid salts, including for example acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid, and the like acids; as well as the salts of amino acids (such as arginine, etc.), and salts of organic acids such as glucuronic acid and the like. Certain specific compounds of the present invention contain both basic and acidic functional groups and thus can be converted into either base or acid addition salts.

The pharmaceutically acceptable salt of the present invention can be synthesized by a conventional chemical method from a parent compound containing an acid or basic group. In general, such a salt is prepared by a method including: reacting the free acid or base form of these compounds with a stoichiometric amount of an appropriate base or acid in water or an organic solvent or a mixture of the two.

The term "isomer" refers to that the compound of the present invention may exist in a specific geometric or stereoisomeric form. It is contemplated in the present invention that all such compounds include cis and trans isomers, (−)- and (+)-enantiomers, (R)- and (S)-enantiomers, diastereomers, (D)-isomers, (L)-isomers, and racemic mixtures thereof and other mixtures, such as enantiomerically or diastereomerically enriched mixtures, all of these mixtures fall within the scope of the present invention. Additional asymmetric carbon atoms may be present in substituents such as an alkyl. All these isomers, and mixtures thereof, are included within the scope of the present invention.

Unless otherwise stated, the term "enantiomers" or "optical isomers" refer to stereoisomers that are mirror images of each other. Unless otherwise stated, the term "cis/trans isomers" or "geometric isomers" are caused by the inability of the double bonds or the single bonds of the ring-forming carbon atoms to rotate freely. Unless otherwise stated, the term "diastereomers" refer to stereoisomers of which the molecules have two or more chiral centers, and there is a non-mirror image relationship between the molecules. Unless otherwise stated, "(D)" or "(+)" represents dextrorotation, "(L)" or "(−)" represents levogyration, and "(DL)" or "(±)" represents being racemic. Unless otherwise stated, the absolute configuration of a stereocenter is represented by a wedge-shaped solid-line bond () and wedge-shaped dashed-line bond ().

"Optional" or "optionally" refers to that the subsequently described events or conditions may but not necessarily occur, and that the description includes instances in which the stated events or conditions occur and instances in which the stated events or conditions do not occur.

The term "substituted" refers to that any one or more hydrogen atoms on a specific atom are replaced with a substituent, which may include deuterium and hydrogen variants, as long as the valence state of the specific atom is normal and the substituted compound is stable. When the substituent is oxygen (i.e., =0), it means that two hydrogen atoms are replaced. Oxygen substitution does not occur on aromatic groups. The term "optionally substituted" refers to that it may or may not be substituted. Unless otherwise specified, the type and number of substituents may be arbitrary on the basis of chemical achievability.

When any variable (e.g., R) occurs more than once in the composition or structure of a compound, its definition in each instance is independent. Thus, for example, if a group is substituted by 0-2 Rs, then the group may optionally be substituted by up to two Rs, and the plural Rs in each case are independent of each other and may be the same or different. Furthermore, combinations of substituents and/or variants thereof are permitted only if such combinations result in stable compounds.

When one of the variables is selected from a bond, it represents that the two groups to which the bond is connected are directly connected. For example, when L in A-L-Z represents a bond, it represents that the structure is actually A-Z.

When it is not specified through which atom the listed substituent is connected to the substituted group, such a substituent can be bonded through any atom thereof. For example, a phenyl group as a substituent can be connected to the substituted group through any carbon atom on the benzene ring.

The term "covalent target head" refers to a chemical group that can form a covalent bond with a nucleophilic reagent, including but not limited to:

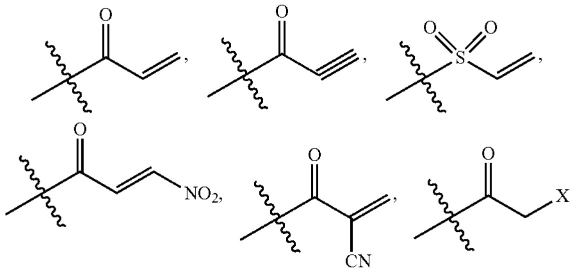

(X is fluorine, chlorine, bromine, or iodine),

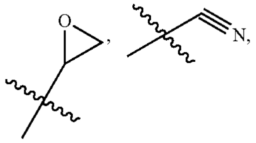

etc.

Unless otherwise specified, the term "alkyl" is used for representing a linear or branched saturated hydrocarbon radical, which may be monosubstituted (e.g., —$CH_2F$) or polysubstituted (e.g., —$CF_3$), and may be monovalent (e.g., methyl) or divalent (e.g., methylene), or multivalent (e.g., methine). Examples of alkyl include methyl (Me), ethyl (Et), propyl (e.g., n-propyl and isopropyl), butyl (e.g., n-butyl, isobutyl, s-butyl, t-butyl), and pentyl (e.g., n-pentyl, isopentyl, neopentyl), etc.

Unless otherwise specified, cycloalkyl includes any stable cyclic or polycyclic hydrocarbon radical in which any carbon atom is saturated, may be mono- or poly-substituted, and may be monovalent, divalent or polyvalent. Examples of these cycloalkyl groups include, but are not limited to, cyclopropyl, norbornyl, [2.2.2]bicyclooctane, [4.4.0]bicyclodecane, and the like.

Unless otherwise specified, the term "halogen" by itself or as part of another substituent represents a fluorine (F), chlorine (Cl), bromine (Br) or iodine (I) atom.

Unless otherwise specified, the term "alkoxy" represents that an alkyl group is connected to the remainder of the molecule through an oxygen atom, wherein the alkyl group has the meaning described in the present invention. Unless otherwise specified, $C_{1-5}$ alkoxy includes $C_1$, $C_2$, $C_3$, $C_4$ and $C_5$ alkoxy. Examples of alkoxy include, but are not limited to: methoxy, ethoxy, n-propoxy, isopropoxy, n-butoxy, sec-butoxy, tert-butoxy, n-pentoxy and S-pentyloxy. The alkoxy group may be optionally substituted with one or more substituents described in the present invention.

Unless otherwise specified, the term "aromatic ring" represents a polyunsaturated aromatic alkane monocyclic ring, which may be mono- or poly-substituted.

Unless otherwise specified, the term "aromatic heterocyclic" represents an aromatic ring containing one to four heteroatoms selected from N, O and S.

In vitro experiments show that the compound provided by the present invention has good JAK3 kinase inhibitory activity and selectivity, and has good application prospects in the field of medicine.

DESCRIPTION OF THE EMBODIMENTS

Figure 1:
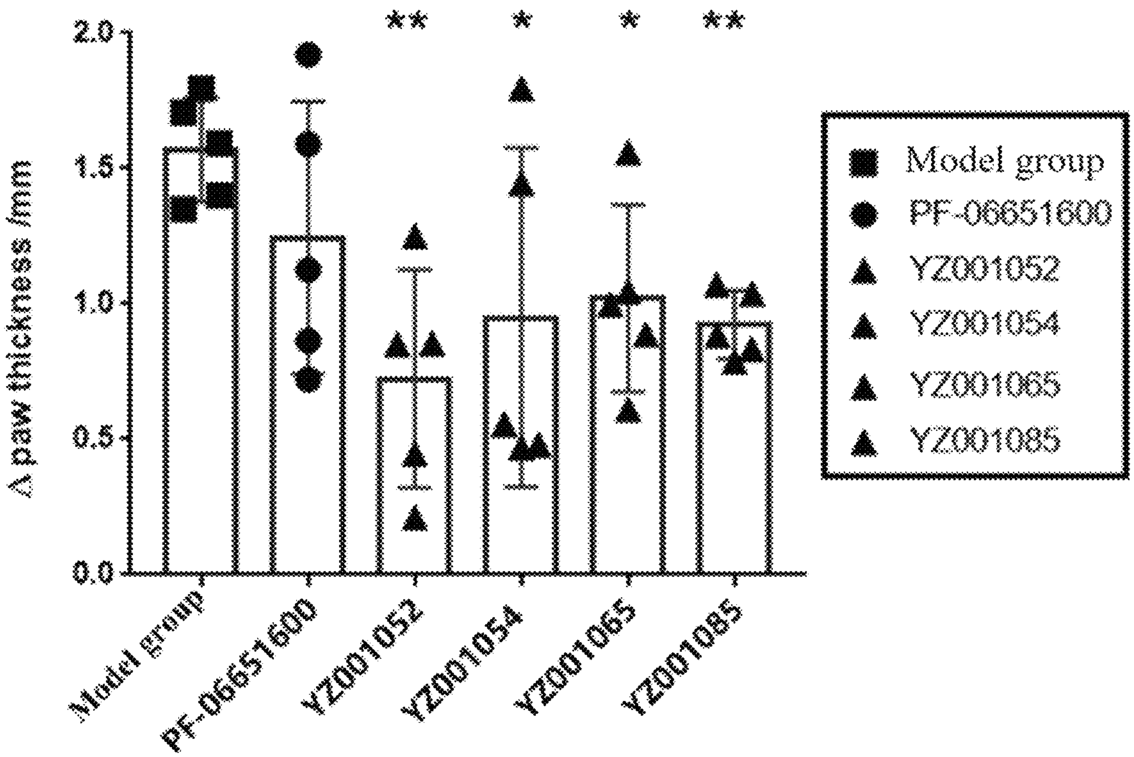
FIG. 1 shows the immunosuppressive activity of a compound on a SRBC mouse model.

The implementability of the present invention will be illustrated hereafter in connection with examples. It should be understood by those skilled in the art that modifications or substitutions can be made to corresponding technical features based on the teachings of the prior art, which will still fall within the claimed scope of the present invention.

Example 1 Synthesis of Intermediate (R)-1e

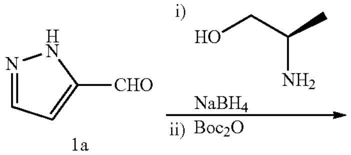

1a

-continued

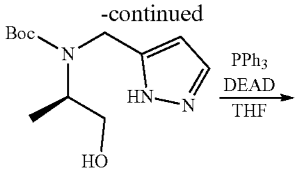

(R)-1b

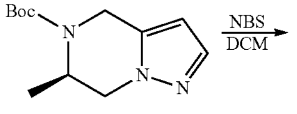

(R)-1c

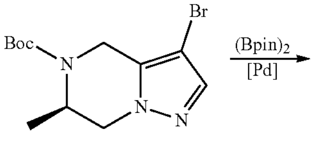

(R)-1d

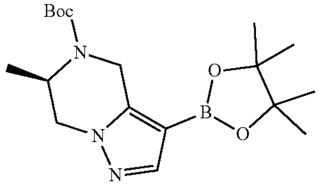

(R)-1e

Step 1: into a 100 ml three-necked flask containing 150 mL of methanol sequentially added were pyrazole-3-formaldehyde 1a (20 g, 208.1 mmol), and (R)-2-aminopropanol (18.7 g, 249.7 mmol) under the protection of nitrogen, and they were reacted at room temperature for 3 hours. It was slowly added with sodium borohydride (19.7 g, 520.4 mmol) in batches, continued to react at room temperature for 2 hours, added with 20 ml of water after the reaction was completed, and slowly added with di-tert-butyl dicarbonate (59.1 g, 270.6 mmol) dropwise in ice bath, and continued to react at room temperature for 24 hours. After the reaction was completed, the reaction solution was poured into 200 ml of water, and extracted with ethyl acetate for 3 times. The organic layers were pooled, dried over anhydrous sodium sulfate, and concentrated under reduced pressure. The obtained crude product was purified with silica gel column chromatography to obtain 40.3 g of an intermediate (R)-1b as colorless oil, with a yield of 75%. ESI$(M+H)^+$=256.

Step 2: the intermediate (R)-1b (40 g, 156.7 mmol) was dissolved in 200 ml of tetrahydrofuran under an ice bath, sequentially added with triphenylphosphine (61.6 g, 235 mmol), diethyl azodicarboxylate (40.9 g, 235 mmol), and reacted at room temperature for 6 hours. After the reaction was completed, the reaction solution was poured into 200 mL of water, and extracted with ethyl acetate for 3 times. The organic layers were pooled, dried over anhydrous sodium sulfate, and concentrated under reduced pressure. The obtained crude product was purified with silica gel column chromatography to obtain 19 g of an intermediate (R)-1c as colorless oil, with a yield of 51%. ESI$(M+H)^+$=238.

Step 3: the intermediate (R)-1c (19 g, 80.1 mmol) was dissolved in 200 ml of dichloromethane, added with N-bromosuccinimide (15.7 g, 88.1 mmol), reacted at room temperature for 1 hour, added with 100 mL of a saturated aqueous solution of sodium bicarbonate after the reaction was completed, and extracted with dichloromethane for 3 times. The organic layers were pooled, dried over anhydrous sodium sulfate, and concentrated under reduced pressure. The obtained crude product was purified with silica gel column chromatography to obtain 23 g of an intermediate (R)-1d as colorless oil, with a yield of 92%. ESI$(M+H)^+$=316.

Step 4: into a 1 L three-necked flask containing 150 mL DMSO sequentially added were the intermediate (R)-1d (23 g, 72.7 mmol), [1,1'-bis(diphenylphosphino) ferrocene]palladium dichloride (5.3 g, 7.3 mmol), bis(pinacolato)diborane ($(Bpin)_2$, 27.7 g, 109.1 mmol) and potassium acetate (28.6 g, 290.9 mmol) under the protection of nitrogen. The reaction system was placed at 95° C. and reacted under stirring well overnight. After the reaction was completed, the reaction solution was cooled to room temperature, poured into 100 mL of water, and extracted with ethyl acetate for 3 times. The organic layers were pooled, washed twice with a saturated sodium chloride solution, dried over anhydrous sodium sulfate, and concentrated under reduced pressure. The obtained crude product was purified by silica gel column chromatography to obtain 13 g of an intermediate (R)-1e as colorless oil, with a yield of 50%. ESI$(M+H)^+$=364.

Example 2 Synthesis of Intermediate(S)-1e

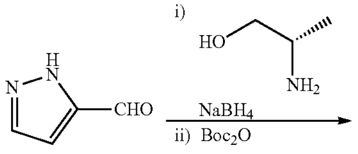

1a

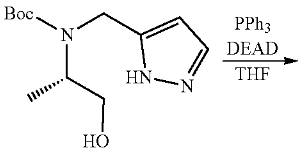

(S)-1b

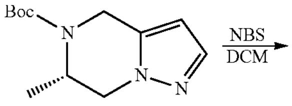

(S)-1c

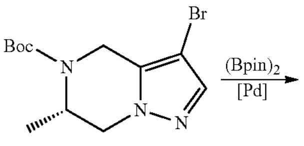

(S)-1d

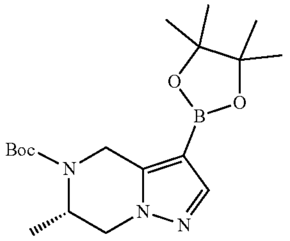

(S)-1e

The (R)-2-aminopropanol in Example 1 was replaced with (S)-2-aminopropanol, and an intermediate(S)-1e was obtained with reference to the synthesis method of Example 1. The yield was 40% (four steps), and ESI(M+H)$^+$=364.

Example 3 Synthesis of Intermediate 2d

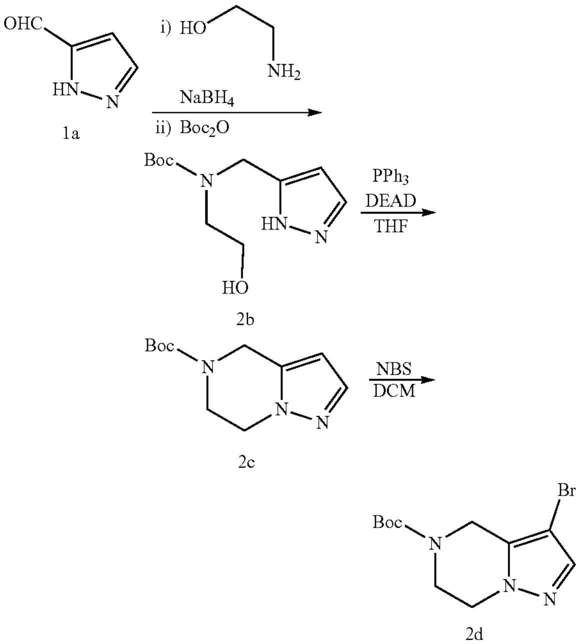

1a 2b 2c 2d

The (R)-2-aminopropanol in Example 1 was replaced with aminoethanol, and an intermediate 2d was obtained with reference to the synthesis method of (R)-1d in Example 1. The yield was 34% (three steps), and ESI(M+H)$^+$=302.

Example 4 Synthesis of Intermediate(S)-3e

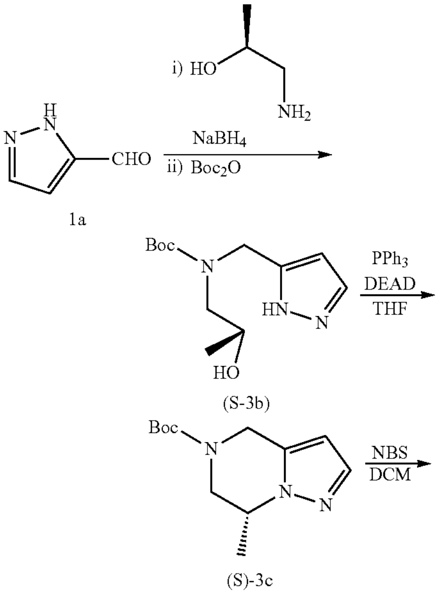

1a (S-3b) (S)-3c

-continued

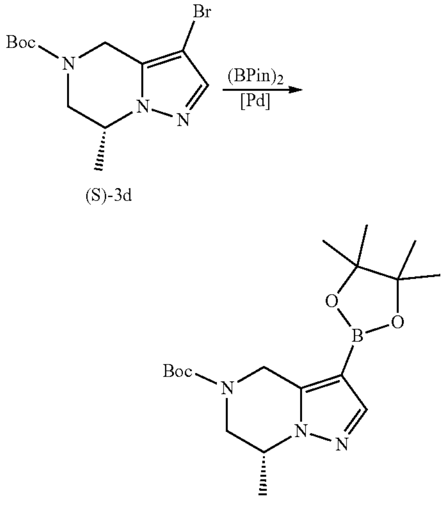

(S)-3d (S)-3e

The (R)-2-aminopropanol in Example 1 was replaced with (R)-1-amino-2-propanol, and an intermediate(S)-3e was obtained with reference to the synthesis method of Example 1. The yield was 45% (four steps), and ESI(M+H)$^+$=364.

Example 5 Synthesis of Intermediate (R)-3e

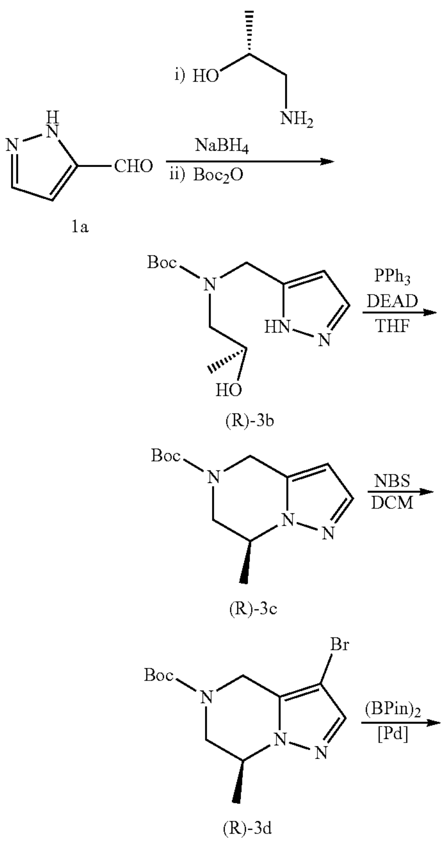

1a (R)-3b (R)-3c (R)-3d

-continued

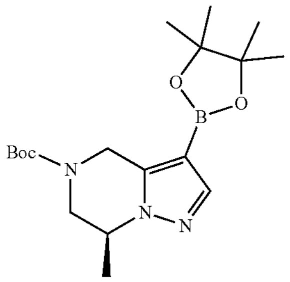

(R)-3e

The (R)-2-aminopropanol in Example 1 was replaced with (S)-1-amino-2-propanol, and an intermediate (R)-3e was obtained with reference to the synthesis method of Example 1. The yield was 39% (four steps), and ESI(M+H)$^+$=364.

Example 6 Synthesis of Intermediate (R)-4e

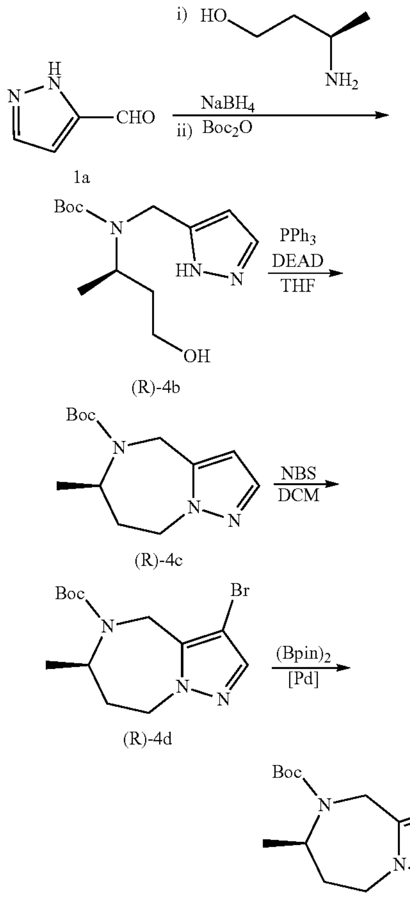

1a
(R)-4b
(R)-4c
(R)-4d
(R)-4e

The (R)-2-aminopropanol in Example 1 was replaced with (R)-3-aminobutanol, and an intermediate (R)-4e was obtained with reference to the synthesis method of Example 1. The yield was 49% (four steps), and ESI(M+H)$^+$=378.

Example 7 Synthesis of Intermediate (R)-5e

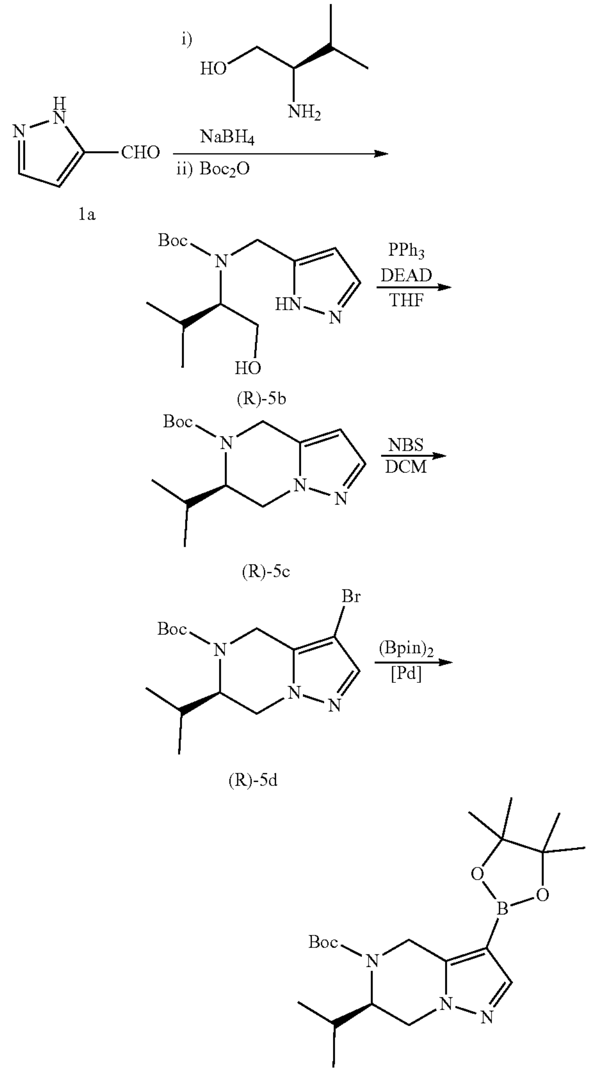

1a
(R)-5b
(R)-5c
(R)-5d
(R)-5e

The (R)-2-aminopropanol in Example 1 was with replaced (R)-(−)-2-amino-3-methyl-1-butanol, and an intermediate (R)-5e was obtained with reference to the synthesis method of Example 1. The yield was 49% (four steps), and ESI(M+H)$^+$=392.

Example 8 Synthesis of Intermediate(S)-5e

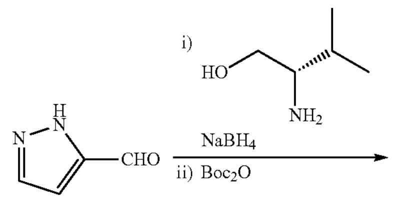

1a

-continued

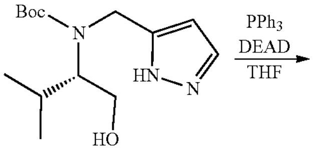

(S)-5b

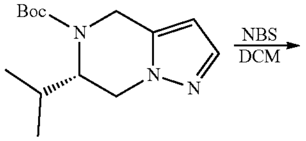

(S)-5c

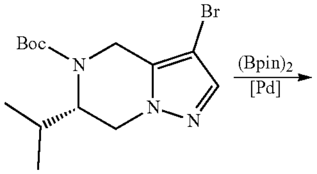

(S)-5d

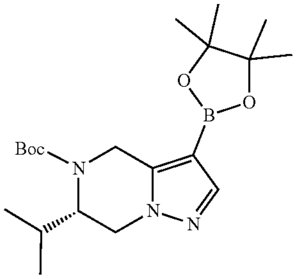

(R)-5e

The (R)-2-aminopropanol in Example 1 was replaced with (S)-(−)-2-amino-3-methyl-1-butanol, and an intermediate(S)-5e was obtained with reference to the synthesis method of Example 1. The yield was 50% (four steps), and ESI$(M+H)^+$=392.

Example 9 Synthesis of Intermediate (S,S)-6d

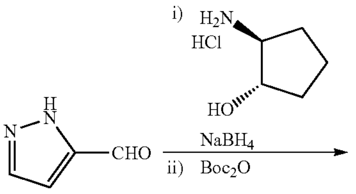

1a

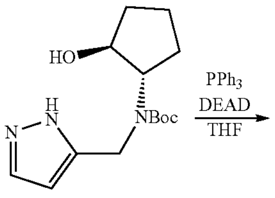

(S,S)-6b

-continued

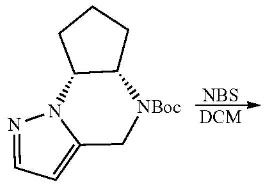

(S,S)-6c

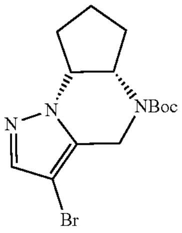

(S,S)-6d

Step 1: into a 100 ml three-necked flask containing 100 mL methanol sequentially added were pyrazole-3-formaldehyde 1a (10 g, 104.1 mmol) and (1S,2S)-2-aminocyclopentanol hydrochloride (17.2 g, 124.8 mmol) under the protection of nitrogen, and they were reacted at room temperature for 3 hours. It was slowly added with sodium borohydride (9.8 g, 260.2 mmol) in batches, continued to react at room temperature for 2 hours, added with 20 ml of water after the reaction was completed, and slowly added with di-tert-butyl dicarbonate (31.8 g, 145.7 mmol) dropwise in ice bath, and continued to react at room temperature for 24 hours. After the reaction was completed, the reaction solution was poured into 200 mL of water, and extracted with ethyl acetate for 3 times. The organic layers were pooled, dried over anhydrous sodium sulfate, and concentrated under reduced pressure. The obtained crude product was purified with silica gel column chromatography to obtain 20 g of an intermediate (S,S)-6b as colorless oil, with a yield of 68%. ESI$(M+H)^+$=282.

Step 2: the intermediate (S,S)-6b (20 g, 71.8 mmol) was dissolved in 200 ml of tetrahydrofuran under an ice bath, sequentially added with triphenylphosphine (27.9 g, 106.6 mmol), diethyl azodicarboxylate (18.6 g, 106.6 mmol), and reacted at room temperature for 6 hours. After the reaction was completed, the reaction solution was poured into 100 ml of water, and extracted with ethyl acetate for 3 times. The organic layers were pooled, dried over anhydrous sodium sulfate, and concentrated under reduced pressure. The obtained crude product was purified with silica gel column chromatography to obtain 12 g of an intermediate (S,S)-6c as colorless oil, with a yield of 66%. ESI$(M+H)^+$=264.

Step 3: the intermediate (S,S)-6c (12 g, 45.5 mmol) was dissolved in 100 ml of dichloromethane, added with N-bromosuccinimide (8.9 g, 50.1 mmol), reacted at room temperature for 1 hour, added with 500 mL of a saturated aqueous solution of sodium bicarbonate after the reaction was completed, and extracted with dichloromethane for 3 times. The organic layers were pooled, dried over anhydrous sodium sulfate, and concentrated under reduced pressure. The obtained crude product was purified with silica gel column chromatography to obtain 10 g of an intermediate (S,S)-6d as colorless oil, with a yield of 92%. ESI$(M+H)^+$=342.

Example 10 Synthesis of Intermediate 7e

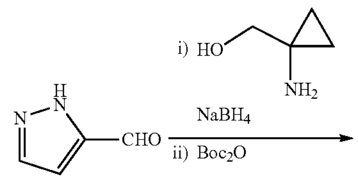

1a

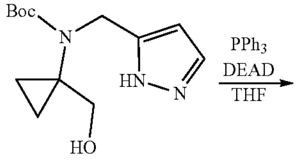

7b

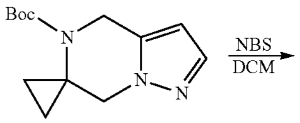

7c

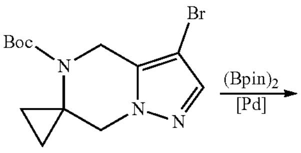

7d

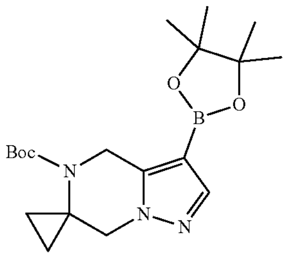

7e

The (R)-2-aminopropanol in Example 1 was replaced with 1-aminocyclopropanemethanol, and an intermediate 7e was obtained with reference to the synthesis method of Example 1. The yield was 54% (four steps), and ESI(M+H)$^+$=376.

Example 11 Synthesis of Intermediate 8f

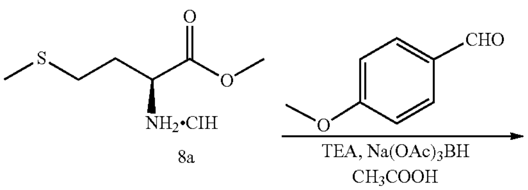

8a

-continued

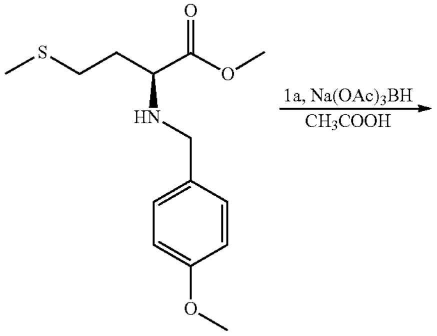

8b

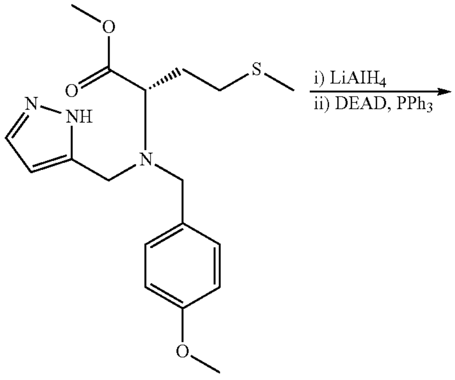

8c

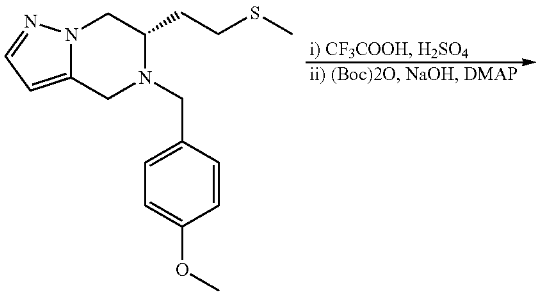

8d

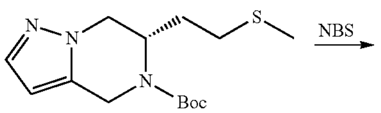

8e

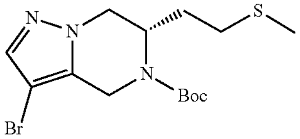

8f

Step 1: a compound 8a (20 g, 100 mmol) was dissolved in 200 ml DCM, and added with triethylamine (14 ml, 100 mmol). The reaction solution was stirred at room temperature for 30 min, then added with acetic acid (5.7 ml, 100 mmol) and p-anisaldehyde (14.3 g, 105 mmol), stirred in an external bath at 40° C. for 1 h, added with $Na(OAc)_3BH$ (29.7 g, 140 mmol), and reacted under stirring in an external bath at 40° C. overnight. After the reaction was completed, the solvent was spin-dried, the solute was added with water (150 ml), and adjusted to the pH of 8-9 with a 3N NaOH solution. The aqueous phase was extracted with EA (50 ml)

for 3 times. The organic phases were pooled, dried over a saturated NaCl solution and anhydrous $Na_2SO_4$, and concentrated under reduced pressure. The obtained crude product was purified by silica gel column chromatography to obtain 22.6 g of 8b, with a yield of 80%. ESI$(M+H)^+$=284.

Step 2: the compound 1a (9.67 g, 101 mmol) was dissolved in 200 ml of DCM, added with acetic acid (3.8 ml, 67 mmol) and a compound 8b (19.1 g, 67 mmol), stirred in an external bath at 40° C. for 1 h, added with $Na(OAc)_3BH$ (19.9 g, 94 mmol), and reacted under stirring in an external bath at 40° C. overnight. After the reaction was completed, the solvent was spin-dried, the solute was added with water (150 ml), and adjusted to the pH of 8-9 with a 3N NaOH solution. The aqueous phase was extracted with EA (50 ml) for 3 times. The organic phases were pooled, dried over a saturated NaCl solution and anhydrous $Na_2SO_4$, and concentrated under reduced pressure. The obtained crude product was purified by silica gel column chromatography to obtain 17.5 g of 8c, with a yield of 72%. ESI$(M+H)^+$=364.

Step 3: into a 500 ml three-necked flask added was lithium aluminum hydride (1.4 g, 38 mmol). A compound 8c (8.8 g, 25 mmol) was dissolved in 150 ml of anhydrous THF and added into a constant-pressure dropping funnel. Under $N_2$ atmosphere, into the three-necked flask injected was 100 ml of anhydrous THF, added with the solution of the compound 8c in THE dropwise under stirring in an ice bath, gradually warmed up to room temperature after the dropwise addition was completed, and reacted under stirring for 3 h. After the reaction was completed, the reaction system was added with sodium sulfate decahydrate in batches until no solid was formed, and filtered. The filter residue was rinsed with DCM for several times. The filtrate was combined, spin-dried, and freeze-dried to obtain a crude product which was directly used in the next step without further purification.

Step 4: the crude product of the reaction of the previous step was dissolved in 200 ml of THF, added with triphenylphosphine (9.8 g, 37.5 mmol), stirred to dissolve, slowly added with DEAD (6.5 g, 37.5 mmol) dropwise at −10° C., slowly warmed up to room temperature after the dropwise addition was completed, and reacted under stirring overnight. After the reaction was completed, the solvent was removed by concentration under reduced pressure, the solute was added with water and extracted with EA for several times. The organic phases were pooled, dried over a saturated NaCl solution and anhydrous $Na_2SO_4$, and concentrated under reduced pressure. The obtained crude product was purified by silica gel column chromatography to obtain 4 g of 8d, with a yield of 51%. ESI$(M+H)^+$=318.

Step 5: a compound 8d (4 g, 12.8 mmol) was dissolved in 6 ml of trifluoroacetic acid, slowly added with 2 ml of concentrated sulfuric acid dropwise, and reacted with stirring under a reflux state for 1 h. After the reaction was completed, the reaction mixture was slowly poured into ice water, and adjusted to the pH of 8-9 with 3N NaOH. The aqueous phase was extracted with EA for several times. The organic phases were pooled, dried over a saturated NaCl solution and anhydrous $Na_2SO_4$, and concentrated under reduced pressure to obtain a crude product which was directly used in the next step without further purification.

Step 6: the crude product from the reaction of the previous step was dissolved in a 1:1 mixed solvent of THF and water, added with Boc anhydride (2.8 g, 32 mmol), NaOH (1.5 g, 38 mmol), and DMAP (159 mg, 1.3 mmol), and reacted under stirring at room temperature overnight. After the reaction was completed, the solvent was removed by concentration under reduced pressure, the solute was added with water and extracted with EA for several times. The organic phases were pooled, dried over a saturated NaCl solution and anhydrous $Na_2SO_4$, and concentrated under reduced pressure. The obtained crude product was purified by silica gel column chromatography to obtain 3.0 g of 8e, with a yield of 78%. ESI$(M+H)^+$=298.

Step 7: a compound 8e (946 mg, 3 mmol) was dissolved in 8 ml of DCM, slowly added with NBS (737 mg, 4 mmol) under an ice bath state, slowly warmed up to room temperature after the addition was completed, and reacted under stirring. After the reaction was completed, the reaction was quenched, added with water, and extracted with DCM for several times. The organic phases were pooled, dried over a saturated NaCl solution and anhydrous $Na_2SO_4$, and concentrated under reduced pressure. The obtained crude product was purified by silica gel column chromatography to obtain 1.0 g of a compound 8f, with a yield of 90%. ESI$(M+H)^+$=376.

Example 12 Synthesis of Intermediate SM1

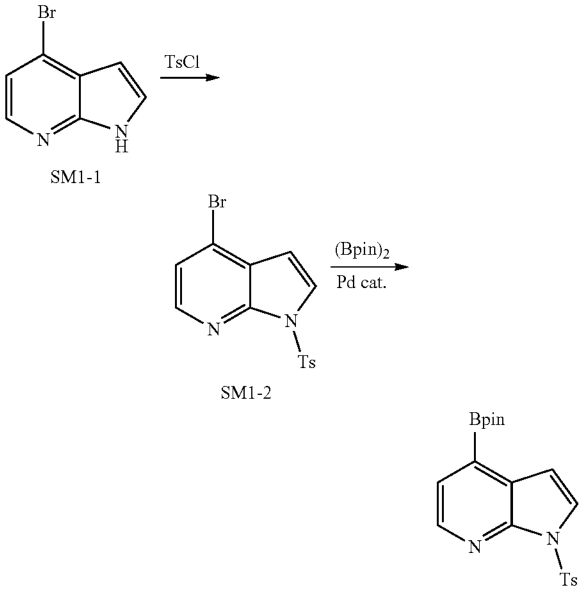

SM1-1

SM1-2

SM1

Step 1: an intermediate SM1-1 (50 g, 253.7 mmol) was dissolved in 300 ml of acetone, then added with sodium hydroxide (20.3 g, 507.5 mmol), slowly added with p-toluenesulfonyl chloride (58.1 g, 304.5 mmol) in batches, and reacted at room temperature for 3 hours. Then the organic solvent was removed under reduced pressure, and the remaining reaction mixture was added with 200 mL of water, and washed and extracted with dichloromethane for 3 times. The organic layers were pooled, dried over anhydrous sodium sulfate, and concentrated under reduced pressure. The obtained crude product was recrystallized with acetonitrile/water and suction-filtered to obtain 75 g of SM1-2 as a white solid, with a yield of 84%, and ESI$(M+H)^+$=351.

Step 2: into a 3 L three-necked flask containing 1 L DMSO sequentially added were the intermediate SM1-2 (75 g, 213.5 mmol), [1,1'-bis(diphenylphosphino) ferrocene] palladium dichloride (15.5 g, 21.3 mmol), bis(pinacolato) diborane (81.3 g, 320.3 mmol) and potassium acetate (83.8 g, 854.2.9 mmol) under the protection of nitrogen. The reaction system was placed at 95° C. and reacted under stirring well overnight. After the reaction was completed, the reaction solution was cooled to room temperature, poured into 1 L of water, and extracted with ethyl acetate for 3 times. The organic layers were pooled, washed twice with a saturated sodium chloride solution, dried over anhydrous sodium sulfate, and concentrated under reduced pressure. The obtained crude product was purified by silica gel column chromatography to obtain 70 g of an intermediate SM1 as a white solid, with a yield of 93%. ESI(M+H)$^+$=399.

Example 13 Synthesis of Intermediate SM2

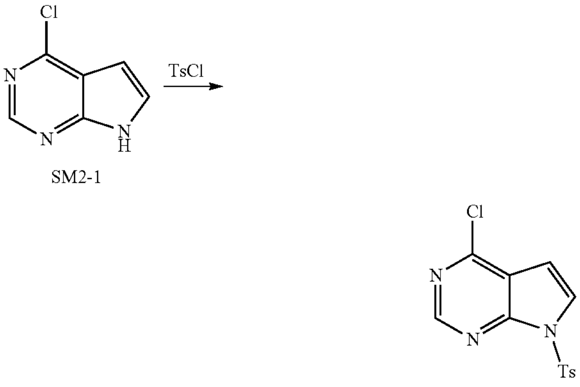

SM2-1

SM2

Step: an intermediate SM2-1 (30 g, 195.2 mmol) was dissolved in 200 ml of acetone, then added with sodium hydroxide (15.6 g, 390.7 mmol), slowly added with p-toluenesulfonyl chloride (40.9 g, 214.8 mmol) in batches, and reacted at room temperature for 3 hours. Then the organic solvent was removed under reduced pressure, and the remaining reaction mixture was added with 100 ml of water, and washed and extracted with dichloromethane for 3 times. The organic layers were pooled, dried over anhydrous sodium sulfate, and concentrated under reduced pressure. The obtained crude product was recrystallized with acetonitrile/water and suction-filtered to obtain 48 g of an intermediate SM2 as a white solid, with a yield of 90%, and ESI(M+H)$^+$=308.

Example 14 Synthesis of Intermediate SM3

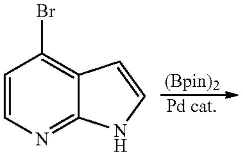

SM1-1

-continued

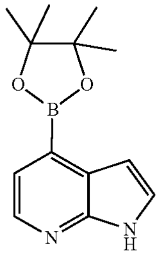

SM3

Step: into a 3 L three-necked flask containing 300 mL DMSO sequentially added were the intermediate SM1-1 (25 g, 126.8 mmol), [1,1'-bis(diphenylphosphino) ferrocene] palladium dichloride (9.3 g, 12.6 mmol), bis(pinacolato) diborane (64.4 g, 253.7 mmol) and potassium acetate (37.3 g, 380.6 mmol) under the protection of nitrogen. The reaction system was placed at 95° C. and reacted under stirring well overnight. After the reaction was completed, the reaction solution was cooled to room temperature, poured into 1 L of water, and extracted with ethyl acetate for 3 times. The organic layers were pooled, washed twice with a saturated sodium chloride solution, dried over anhydrous sodium sulfate, and concentrated under reduced pressure. The obtained crude product was purified by silica gel column chromatography to obtain 20 g of an intermediate SM1 as a white solid, with a yield of 64%. ESI(M+H)$^+$=245.

Example 15 Synthesis of Intermediate (R)-1e-IM3

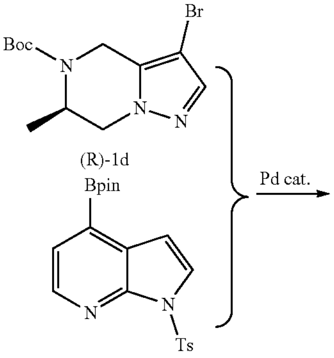

(R)-1d

SM1

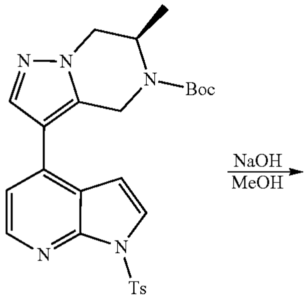

(R)-1e-IM1

-continued

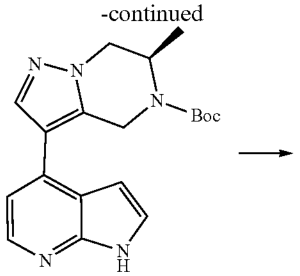

(R)-1e-IM2

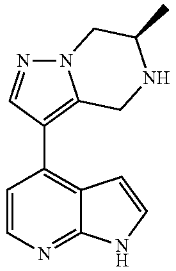

(R)-1e-IM3

Step 1: into a 200 ml three-necked flask containing 100 mL of 1,4-dioxane sequentially added were the intermediate (R)-1d (10 g, 25.1 mmol), tetrakis(triphenylphosphorus) palladium (2.9 g, 2.5 mmol), the intermediate SM1 (10 g, 25.1 mmol) and potassium carbonate (13.8 g, 100.4 mmol) under the protection of nitrogen, and the reaction system was placed at 95° C. and reacted under stirring well overnight. After the reaction was completed, the reaction solution was cooled to room temperature, poured into 50 mL of water, and extracted with ethyl acetate for 3 times. The organic layers were pooled, washed twice with a saturated sodium chloride solution, dried over anhydrous sodium sulfate, and concentrated under reduced pressure. The obtained crude product was purified by silica gel column chromatography to obtain 10 g of an intermediate (R)-1e-IM1 as a light yellow solid, with a yield of 83%, and ESI$(M+H)^+$=508.

Step 2: into a 500 mL three-necked flask containing 200 mL of methanol sequentially added were the intermediate (R)-1e-IM1 (10 g, 19.7 mmol) and sodium hydroxide (1.58 g, 39.4 mmol), and the reaction system was placed at 50° C. and reacted under stirring well for 3 hours. After the reaction was completed, the reaction solution was cooled to room temperature, poured into water, and extracted with dichloromethane for 3 times. The organic layers were pooled, washed twice with a saturated sodium chloride solution, dried over anhydrous sodium sulfate, and concentrated under reduced pressure. The obtained crude product was purified by silica gel column chromatography to obtain 5.5 g of an intermediate (R)-1e-IM2 as a white solid, with a yield of 78%. ESI$(M+H)^+$=354.

Step 3: the intermediate (R)-1e-IM2 (5 g, 14.1 mmol) was dissolved in dichloromethane, added with an equal volume of trifluoroacetic acid, reacted at room temperature overnight, adjusted to the pH of 8-9 after the reaction was completed, and extracted with dichloromethane for 3 times. The organic layers were pooled, washed with a saturated sodium chloride solution twice, dried over anhydrous sodium sulfate, and concentrated under reduced pressure. The obtained crude product was purified by silica gel column chromatography to obtain 3 g of an intermediate (R)-1e-IM3 as a white solid, with a yield of 83%. ESI$(M+H)^+$=254.

(R)-1e-IM3

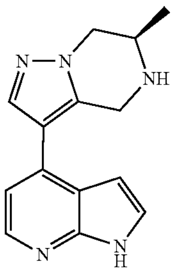

(S)-1e-IM3

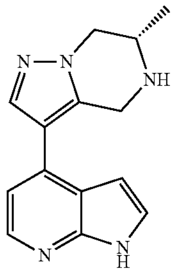

2e-IM3

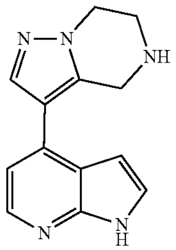

(S)-3e-IM3

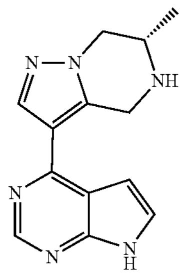

(R)-3e-IM3

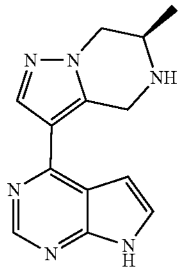

-continued (S)-4e-IM3

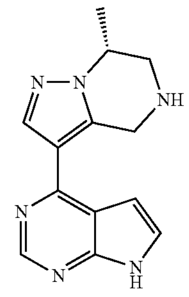

(R)-4e-IM3

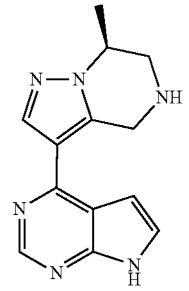

(R)-5e-IM3

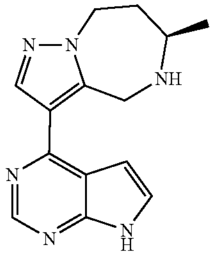

(S)-6e-IM3

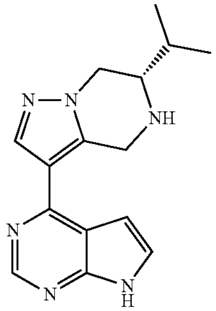

(R)-6e-IM3

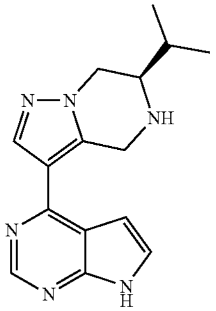

-continued (S,S)-7d-IM3

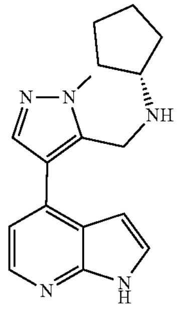

Example 16 Synthesis of Intermediate(S)-1e-IM3

The intermediate (R)-1d in the Example 15 was replaced with an intermediate (S)-1d, and an intermediate(S)-1e-IM3 was obtained with reference to the synthesis method of Example 15, with a yield of 49% (three steps), and $ESI(M+H)^{+}=254$.

Example 17 Synthesis of Intermediate 2e-IM3

The intermediate (R)-1d in the Example 15 was replaced with an intermediate 2d, and an intermediate 2e-IM3 was obtained with reference to the synthesis method of Example 15, with a yield of 50% (three steps), and $ESI(M+H)^{+}=240$.

Example 18 Synthesis of Intermediate(S)-3e-IM3

The intermediate (R)-1d in the Example 15 was replaced with an intermediate (S)-1d, the intermediate SM1 was replaced with an intermediate SM2, and an intermediate(S)-3e-IM3 was obtained with reference to the synthesis method of Example 15, with a yield of 53% (three steps), and $ESI(M+H)^{+}=255$.

Example 19 Synthesis of Intermediate (R)-3e-IM3

The intermediate (R)-1d in the Example 15 was replaced with an intermediate (R)-1e, the intermediate SM1 was replaced with an intermediate SM2, and an intermediate (R)-3e-IM3 was obtained with reference to the synthesis method of Example 15, with a yield of 57% (three steps), and $ESI(M+H)^{+}=255$.

Example 20 Synthesis of Intermediate(S)-4e-IM3

The intermediate (R)-1d in the Example 15 was replaced with an intermediate (S)-3e, the intermediate SM1 was replaced with an intermediate SM2, and an intermediate(S)-4e-IM3 was obtained with reference to the synthesis method of Example 15, with a yield of 65% (three steps), and $ESI(M+H)^{+}=255$.

Example 21 Synthesis of Intermediate (R)-4e-IM3

The intermediate (R)-1d in the Example 15 was replaced with an intermediate (R)-3e, the intermediate SM1 was replaced with an intermediate SM2, and an intermediate (R)-4e-IM3 was obtained with reference to the synthesis method of Example 15, with a yield of 45% (three steps), and $ESI(M+H)^{+}=255$.

Example 22 Synthesis of Intermediate (R)-5e-IM3

The intermediate (R)-1d in the Example 15 was replaced with an intermediate (R)-4e, the intermediate SM1 was replaced with an intermediate SM2, and an intermediate (R)-5e-IM3 was obtained with reference to the synthesis method of Example 15, with a yield of 42% (three steps), and ESI$(M+H)^+$=269.

Example 23 Synthesis of Intermediate(S)-6e-IM3

The intermediate (R)-1d in the Example 15 was replaced with an intermediate(S)-5e, the intermediate SM1 was replaced with an intermediate SM2, and an intermediate(S)-6e-IM3 was obtained with reference to the synthesis method of Example 15, with a yield of 48% (three steps), and ESI$(M+H)^+$=283.

Example 24 Synthesis of Intermediate (R)-6e-IM3

The intermediate (R)-1d in the Example 15 was replaced with an intermediate (R)-5e, the intermediate SM1 was replaced with an intermediate SM2, and an intermediate (R)-6e-IM3 was obtained with reference to the synthesis method of Example 15, with a yield of 42% (three steps), and ESI$(M+H)^+$=283.

Example 25 Synthesis of Intermediate (S,S)-7d-IM3

The intermediate (R)-1d in the Example 15 was replaced with an intermediate (S,S)-6d, the intermediate SM1 was replaced with an intermediate SM2, and an intermediate (S,S)-7d-IM3 was obtained with reference to the synthesis method of Example 15, with a yield of 43% (three steps), and ESI$(M+H)^+$=280.

Example 26 Synthesis of Intermediate 8d-IM5

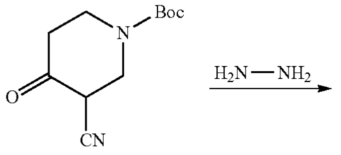

8d-IM1

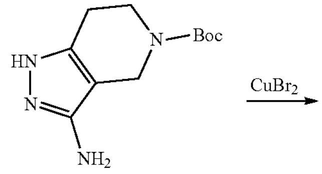

8d-IM2

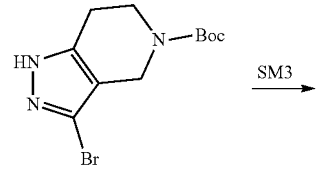

8d-IM3

-continued

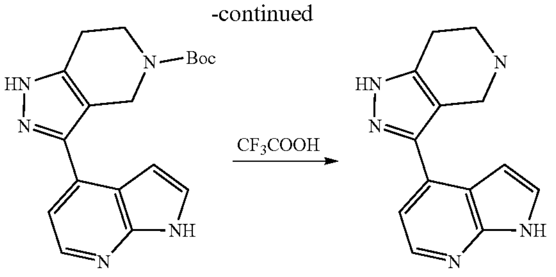

8d-IM4 8d-IM5

Step 1: into a 500 mL three-necked flask containing 200 mL of methanol sequentially added were the intermediate 8d-IM1 (20 g, 89.1 mmol) and hydrazine (4.2 g, 133.7 mmol), and the reaction system was placed at 70° C. and reacted under stirring well for 4 hours. After the reaction was completed, the mixture was cooled to room temperature and concentrated under reduced pressure. The crude product was purified by silica gel column chromatography to obtain 18 g of an intermediate 8d-IM2 as a white solid, with a yield of 85%. ESI$(M+H)^+$=239.

Step 2: into a 500 mL three-necked flask containing 200 mL of acetonitrile sequentially added were the intermediate 8d-IM2 (15 g, 62.9 mmol), copper bromide (14.1 g, 62.9 mmol), and isoamyl nitrite (8.8 g, 75.5 mmol), and the reaction system was placed at 60° C. and reacted under stirring well for 4 hours. After the reaction was completed, the reaction solution was cooled to room temperature, poured into water, and extracted with dichloromethane for 3 times. The organic layers were pooled, washed twice with a saturated sodium chloride solution, dried over anhydrous sodium sulfate, and concentrated under reduced pressure. The obtained crude product was purified by silica gel column chromatography to obtain 10 g of an intermediate 8d-IM3 as a yellow solid, with a yield of 52%. ESI$(M+H)^+$=302.

Step 3: into a 200 ml three-necked flask containing 100 mL of 1,4-dioxane sequentially added were the intermediate 8d-IM3 (10 g, 33.1 mmol), tetrakis(triphenylphosphorus) palladium (3.8 g, 3.3 mmol), the intermediate SM3 (12.1 g, 49.1 mmol) and potassium carbonate (13.8 g, 100.4 mmol) under the protection of nitrogen, and the reaction system was placed at 95° C. and reacted under stirring well overnight. After the reaction was completed, the reaction solution was cooled to room temperature, poured into 100 ml of water, and extracted with ethyl acetate for 3 times. The organic layers were pooled, washed twice with a saturated sodium chloride solution, dried over anhydrous sodium sulfate, and concentrated under reduced pressure. The obtained crude product was purified by silica gel column chromatography to obtain 7 g of an intermediate 8d-IM4 as a light yellow solid, with a yield of 63%, and ESI$(M+H)^+$=340.

Step 4: the intermediate 8d-IM4 (7 g, 20.6 mmol) was dissolved in dichloromethane, added with an equal volume of trifluoroacetic acid, reacted at room temperature overnight, adjusted to the pH of 8-9 after the reaction was completed, and extracted with dichloromethane for 3 times. The organic layers were pooled, washed with a saturated sodium chloride solution twice, dried over anhydrous sodium sulfate, and concentrated under reduced pressure. The obtained crude product was purified by silica gel column chromatography to obtain 5 g of an intermediate 8d-IM5 as a white solid, with a yield of 71%. ESI$(M+H)^+$=240.

Example 27 Synthesis of Intermediate 9f-IM3

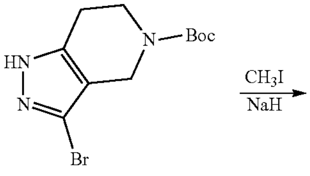

8d-IM3

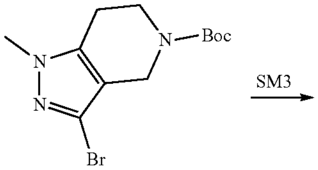

9f-IM1

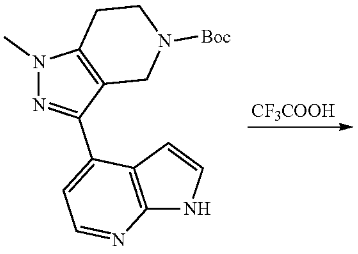

9f-IM2

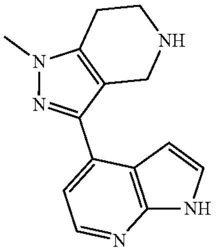

9f-IM3

Step 1: into a 500 mL three-necked flask containing 100 mL of DMF sequentially added were the intermediate 8d-IM3 (20 g, 66.1 mmol), sodium hydrogen (3.2 g, 132.3 mmol), and methyl iodide (11.2 g, 79.4 mmol), and the reaction system was placed at 0° C. and reacted under stirring well for 2 hours. After the reaction was completed, the reaction solution was poured into water, and extracted with dichloromethane for 3 times. The organic layers were pooled, washed twice with a saturated sodium chloride solution, dried over anhydrous sodium sulfate, and concentrated under reduced pressure. The obtained crude product was purified by silica gel column chromatography to obtain 15 g of an intermediate 9f-IM1 as a yellow solid, with a yield of 71%. ESI(M+H)$^+$=316.

Step 2: into a 200 ml three-necked flask containing 100 mL of 1,4-dioxane sequentially added were the intermediate 9f-IM1 (15 g, 47.4 mmol), tetrakis(triphenylphosphorus) palladium (5.4 g, 4.7 mmol), the intermediate SM3 (17.3 g, 71.1 mmol) and potassium carbonate (19.6 g, 142.3 mmol) under the protection of nitrogen, and the reaction system was placed at 95° C. and reacted under stirring well overnight. After the reaction was completed, the reaction solution was cooled to room temperature, poured into 100 ml of water, and extracted with ethyl acetate for 3 times. The organic layers were pooled, washed twice with a saturated sodium chloride solution, dried over anhydrous sodium sulfate, and concentrated under reduced pressure. The obtained crude product was purified by silica gel column chromatography to obtain 12 g of an intermediate 9f-IM2 as a light yellow solid, with a yield of 75%, and ESI(M+H)$^+$=354.

Step 3: the intermediate 9f-IM2 (12 g, 20.6 mmol) was dissolved in dichloromethane, added with an equal volume of trifluoroacetic acid, reacted at room temperature overnight, adjusted to the pH of 8-9 after the reaction was completed, and extracted with dichloromethane for 3 times. The organic layers were pooled, washed with a saturated sodium chloride solution twice, dried over anhydrous sodium sulfate, and concentrated under reduced pressure. The obtained crude product was purified by silica gel column chromatography to obtain 5 g of an intermediate 9f-IM3 as a white solid, with a yield of 58%. ESI(M+H)$^+$ =254.

Example 28 Synthesis of Intermediate 10g-IM3

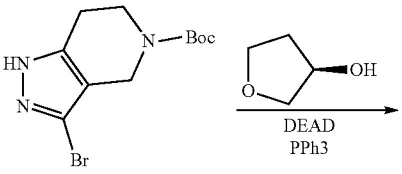

8d-IM3

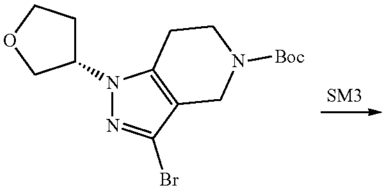

10g-IM1

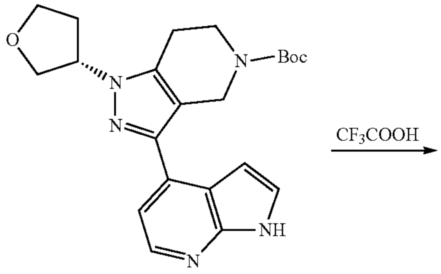

10g-IM2

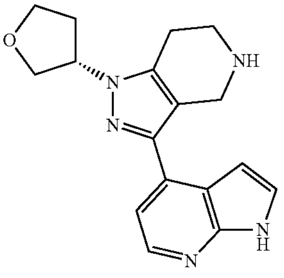

10g-IM3

Step 1: into a 500 mL three-necked flask containing 100 mL of DMF sequentially added were the intermediate 8d-IM3 (20 g, 66.1 mmol), R-3-hydroxytetrahydrofuran (7 g, 79.4 mmol), triphenylphosphine (26 g, 99.2 mmol), diethyl azodicarboxylate (17.2 g, 99.2 mmol), and the reaction system was placed at room temperature and reacted under stirring well for 2 hours. After the reaction was completed, the reaction solution was poured into water, and extracted with ethyl acetate for 3 times. The organic layers were pooled, washed twice with a saturated sodium chloride solution, dried over anhydrous sodium sulfate, and concentrated under reduced pressure. The obtained crude product was purified by silica gel column chromatography to obtain 18 g of an intermediate 10g-IM1 as a yellow solid, with a yield of 75%. ESI(M+H)$^+$=372.

Step 2: into a 500 ml three-necked flask containing 300 mL of 1,4-dioxane sequentially added were the intermediate 10g-IM1 (18 g, 48.4 mmol), tetrakis(triphenylphosphorus) palladium (5.6 g, 4.8 mmol), the intermediate SM3 (17.7 g, 72.5 mmol) and potassium carbonate (20 g, 145 mmol) under the protection of nitrogen, and the reaction system was placed at 95° C. and reacted under stirring well overnight. After the reaction was completed, the reaction solution was cooled to room temperature, poured into 200 ml of water, and extracted with ethyl acetate for 3 times. The organic layers were pooled, washed twice with a saturated sodium chloride solution, dried over anhydrous sodium sulfate, and concentrated under reduced pressure. The obtained crude product was purified by silica gel column chromatography to obtain 14 g of an intermediate 10g-IM2 as a light yellow solid, with a yield of 73%, and ESI(M+H)$^+$=410.

Step 3: the intermediate 10g-IM2 (12 g, 20.6 mmol) was dissolved in dichloromethane, added with an equal volume of trifluoroacetic acid, reacted at room temperature overnight, adjusted to the pH of 8-9 after the reaction was completed, and extracted with dichloromethane for 3 times. The organic layers were pooled, washed with a saturated sodium chloride solution twice, dried over anhydrous sodium sulfate, and concentrated under reduced pressure. The obtained crude product was purified by silica gel column chromatography to obtain 6 g of an intermediate 10g-IM3 as a white solid, with a yield of 57%. ESI(M+H)$^+$=310.

Example 29 Synthesis of Intermediate 11h-IM1

1-1

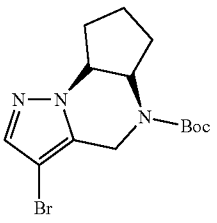

11h-IM1

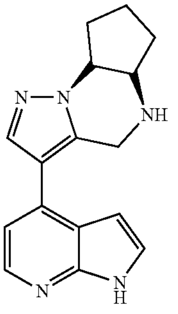

Referring to the synthesis method of intermediate (S,S)-6d in Example 9, the (1S,2S)-2-aminocyclopentanol hydrochloride was replaced with (1R,2R)-2-aminocyclopentanol to obtain an intermediate 1-1, and then referring to the synthesis method of the intermediate (S,S)-7d-IM3 in Example 25, the intermediate (S,S)-6d was replaced with the intermediate 1-1 to obtain 11h-IM1 with a yield 34%, and ESI(M+H)$^+$=280.

Example 30 Synthesis of Intermediate 12I-IM1

1-2

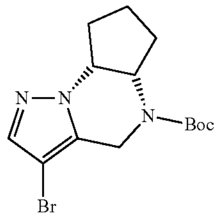

12I-IM1

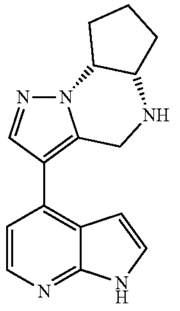

Referring to the synthesis method of intermediate (S,S)-6d in Example 9, the (1S,2S)-2-aminocyclopentanol hydrochloride was replaced with (1R,2R)-2-aminocyclohexanol to obtain an intermediate 1-2, and then referring to the synthesis method of the intermediate (S,S)-7d-IM3 in Example 25, the intermediate (S,S)-6d was replaced with the intermediate 1-2 to obtain 12I-IM1 with a yield of 25%, and ESI(M+H)$^+$=294.

Example 31 Synthesis of Intermediate 13J-IM1

1-3

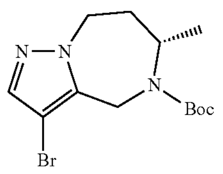

13J-IM1

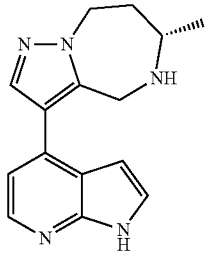

Referring to the synthesis method of intermediate (R)-1d in Example 1, the (R)-2-aminopropanol was replaced with (S)-3-aminobutanol to obtain an intermediate 1-4, and then referring to the synthesis method of the intermediate (R)-1e-IM3 in Example 15, the intermediate R-1d was replaced with the intermediate 1-3 to obtain 13J-IM1 with a yield of 28%, and $ESI(M+H)^+=268$.

Example 32 Synthesis of Intermediate 14K-IM3

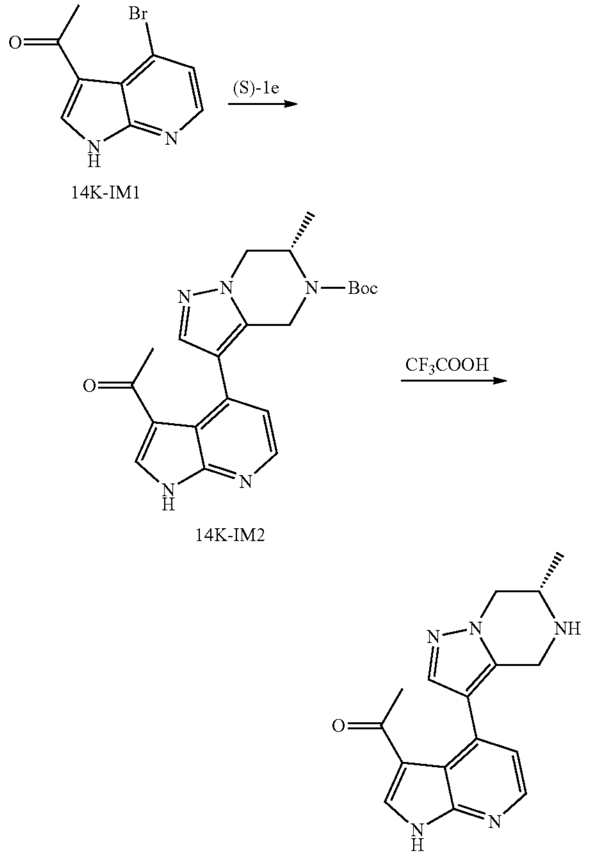

14K-IM1, 14K-IM2, 14K-IM3

Step 1: into a 500 ml three-necked flask containing 200 mL of 1,4-dioxane sequentially added were the intermediate (S)-1e (22.7 g, 62.7 mmol), tetrakis(triphenylphosphorus) palladium (4.8 g, 4.1 mmol), the intermediate 14K-IM1 (10 g, 41.8 mmol) and potassium carbonate (17.3 g, 125.4 mmol) under the protection of nitrogen, and the reaction system was placed at 95° C. and reacted under stirring well overnight. After the reaction was completed, the reaction solution was cooled to room temperature, poured into 100 mL of water, and extracted with ethyl acetate for 3 times. The organic layers were pooled, washed twice with a saturated sodium chloride solution, dried over anhydrous sodium sulfate, and concentrated under reduced pressure. The obtained crude product was purified by silica gel column chromatography to obtain 11 g of an intermediate 14K-IM2 as a light yellow solid, with a yield of 66%, and $ESI(M+H)^+=396$.

Step 2: the intermediate 14K-IM2 (11 g, 20.6 mmol) was dissolved in dichloromethane, added with an equal volume of trifluoroacetic acid, reacted at room temperature overnight, adjusted to the pH of 8-9 after the reaction was completed, and extracted with dichloromethane for 3 times. The organic layers were pooled, washed with a saturated sodium chloride solution twice, dried over anhydrous sodium sulfate, and concentrated under reduced pressure. The obtained crude product was purified by silica gel column chromatography to obtain 6 g of an intermediate 14K-IM3 as a yellow solid, with a yield of 73%. $ESI(M+H)^+=296$.

Example 33 Synthesis of Intermediate 15L-IM4

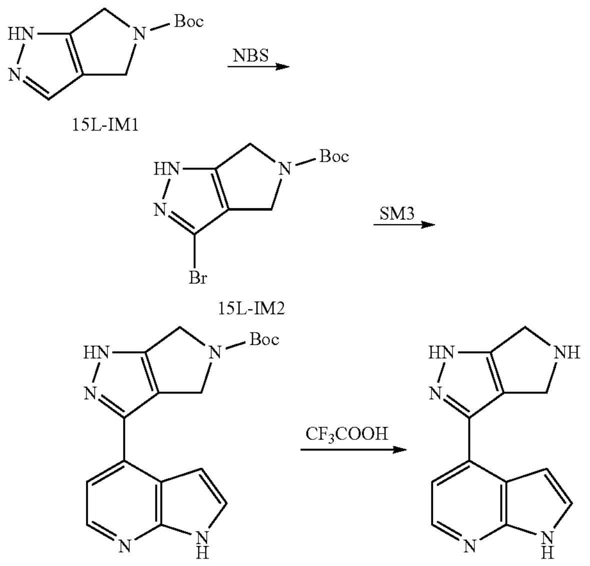

15L-IM1, 15L-IM2, 15L-IM3, 15L-IM4

Step 1: the intermediate 15L-IM1 (20 g, 95.5 mmol) was dissolved in dichloromethane, then added with NBS, reacted at room temperature for 1 hour, and extracted with dichloromethane for 3 times after the reaction was completed. The organic layers were pooled, washed with a saturated sodium chloride solution twice, dried over anhydrous sodium sulfate, and concentrated under reduced pressure. The obtained crude product was purified by silica gel column chromatography to obtain 21 g of an intermediate 15L-IM2 as a yellow solid, with a yield of 77%. $ESI(M+H)^+=288$.

Step 2: into a 500 ml three-necked flask containing 300 mL of 1,4-dioxane sequentially added were the intermediate 15L-IM2 (21 g, 72.8 mmol), tetrakis(triphenylphosphorus) palladium (8.4 g, 7.2 mmol), the intermediate SM3 (26.6 g, 109.3 mmol) and potassium carbonate (30 g, 218.1 mmol) under the protection of nitrogen, and the reaction system was placed at 95° C. and reacted under stirring well overnight. After the reaction was completed, the reaction solution was cooled to room temperature, poured into 100 mL of water, and extracted with ethyl acetate for 3 times. The organic layers were pooled, washed twice with a saturated sodium chloride solution, dried over anhydrous sodium sulfate, and concentrated under reduced pressure. The obtained crude product was purified by silica gel column chromatography to obtain 15 g of an intermediate 15L-IM3 as a light yellow solid, with a yield of 65%, and $ESI(M+H)^+=326$.

Step 3: the intermediate 15L-IM3 (11 g, 20.6 mmol) was dissolved in dichloromethane, added with an equal volume of trifluoroacetic acid, reacted at room temperature overnight, adjusted to the pH of 8-9 after the reaction was completed, and extracted with dichloromethane for 3 times. The organic layers were pooled, washed with a saturated sodium chloride solution twice, dried over anhydrous sodium sulfate, and concentrated under reduced pressure. The obtained crude product was purified by silica gel column chromatography to obtain 5 g of an intermediate 15L-IM3 as a yellow solid, with a yield of 50%. ESI(M+H)$^+$=226.

Example 34 Synthesis of Intermediate 16M-IM1

16M-IM1

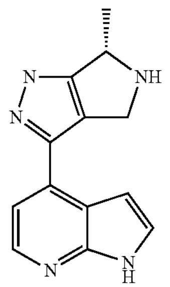

Referring to the synthesis method of the intermediate 15L-IM4 in Example 33, 15L-IM1 was replaced with tert-butyl (S)-6-methyl-4,6-dihydropyrrolo[3,4-c]pyrazole-5(1H)-carboxylate, and 3 g of an intermediate 16M-IM1 was obtained by a three-step reaction, with a yield of 54%. ESI(M+H)$^+$=240.

Example 35 Synthesis of Intermediate 17N-IM3

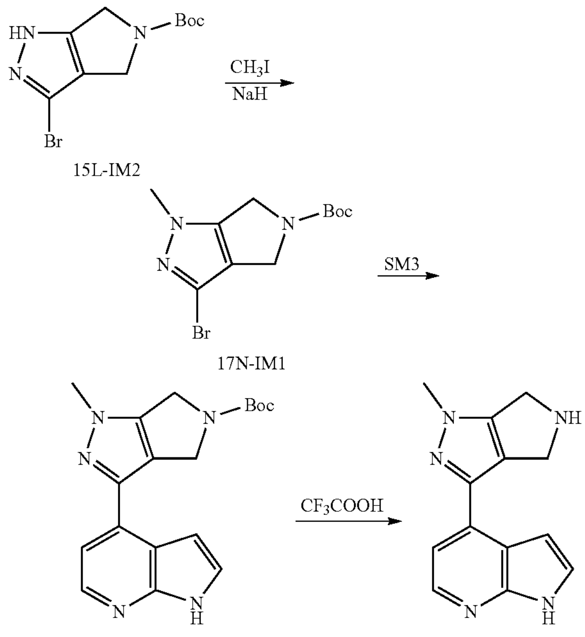

15L-IM2 17N-IM1 17N-IM2 17N-IM3

Step 1: into a 500 mL three-necked flask containing 100 mL of DMF sequentially added were the intermediate 15L-IM2 (15 g, 52 mmol), sodium hydrogen (2.5 g, 104 mmol), and methyl iodide (7.3 g, 52 mmol), and the reaction system was placed at 0° C. and reacted under stirring well for 2 hours. After the reaction was completed, the reaction solution was poured into water, and extracted with dichloromethane for 3 times. The organic layers were pooled, washed twice with a saturated sodium chloride solution, dried over anhydrous sodium sulfate, and concentrated under reduced pressure. The obtained crude product was purified by silica gel column chromatography to obtain 10 g of an intermediate 17N-IM1 as a yellow solid, with a yield of 66%. ESI(M+H)$^+$=302.

Step 2: into a 200 ml three-necked flask containing 100 mL of 1,4-dioxane sequentially added were intermediate 17N-IM1 (10 g, 33 mmol), tetrakis(triphenylphosphorus) palladium (3.8 g, 3.3 mmol), the intermediate SM3 (12.1 g, 49.6 mmol) and potassium carbonate (13.7 g, 99.3 mmol) under the protection of nitrogen, and the reaction system was placed at 95° C. and reacted under stirring well overnight. After the reaction was completed, the reaction solution was cooled to room temperature, poured into 100 mL of water, and extracted with ethyl acetate for 3 times. The organic layers were pooled, washed twice with a saturated sodium chloride solution, dried over anhydrous sodium sulfate, and concentrated under reduced pressure. The obtained crude product was purified by silica gel column chromatography to obtain 5 g of an intermediate 17N-IM2 as a light yellow solid, with a yield of 45%, and ESI(M+H)$^+$=340.

Step 3: the intermediate 17N-IM2 (5 g, 20.6 mmol) was dissolved in dichloromethane, added with an equal volume of trifluoroacetic acid, reacted at room temperature overnight, adjusted to the pH of 8-9 after the reaction was completed, and extracted with dichloromethane for 3 times. The organic layers were pooled, washed with a saturated sodium chloride solution twice, dried over anhydrous sodium sulfate, and concentrated under reduced pressure. The obtained crude product was purified by silica gel column chromatography to obtain 2 g of an intermediate 17N-IM3 as a white solid, with a yield of 57%. ESI(M+H)$^+$=240.

Example 36 Synthesis of Intermediate 18O-IM4

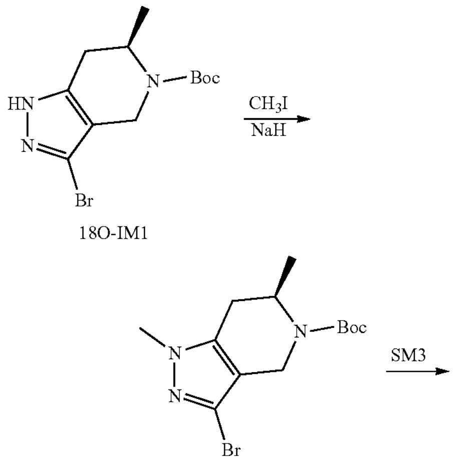

18O-IM1 18O-IM2

-continued

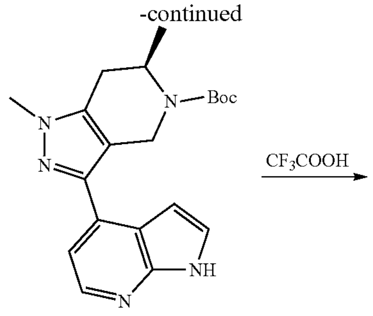

18O-IM3

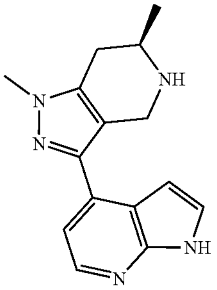

18O-IM4

Step 1: into a 500 mL three-necked flask containing 100 mL of DMF sequentially added were the intermediate 18O-IM1 (20 g, 63.2 mmol), sodium hydrogen (3.0 g, 126 mmol), and methyl iodide (10.7 g, 75.9 mmol), and the reaction system was placed at 0° C. and reacted under stirring well for 2 hours. After the reaction was completed, the reaction solution was poured into water, and extracted with dichloromethane for 3 times. The organic layers were pooled, washed twice with a saturated sodium chloride solution, dried over anhydrous sodium sulfate, and concentrated under reduced pressure. The obtained crude product was purified by silica gel column chromatography to obtain 15 g of an intermediate 180-IM2 as a yellow solid, with a yield of 75%. ESI(M+H)$^+$=330.

Step 2: into a 200 ml three-necked flask containing 100 mL of 1,4-dioxane sequentially added were the intermediate 180-IM2 (15 g, 45.4 mmol), tetrakis(triphenylphosphorus) palladium (5.2 g, 4.5 mmol), the intermediate SM3 (16.6 g, 68.1 mmol) and potassium carbonate (18.8 g, 136.2 mmol) under the protection of nitrogen, and the reaction system was placed at 95° C. and reacted under stirring well overnight. After the reaction was completed, the reaction solution was cooled to room temperature, poured into 100 ml of water, and extracted with ethyl acetate for 3 times. The organic layers were pooled, washed twice with a saturated sodium chloride solution, dried over anhydrous sodium sulfate, and concentrated under reduced pressure. The obtained crude product was purified by silica gel column chromatography to obtain 10 g of an intermediate 180-IM3 as a light yellow solid, with a yield of 60%. ESI(M+H)$^+$=368.

Step 3: the intermediate 180-IM3 (7 g, 20.6 mmol) was dissolved in dichloromethane, added with an equal volume of trifluoroacetic acid, reacted at room temperature overnight, adjusted to the pH of 8-9 after the reaction was completed, and extracted with dichloromethane for 3 times. The organic layers were pooled, washed with a saturated sodium chloride solution twice, dried over anhydrous sodium sulfate, and concentrated under reduced pressure. The obtained crude product was purified by silica gel column chromatography to obtain 5.5 g of an intermediate 180-IM4 as a white solid, with a yield of 76%. ESI(M+H)$^+$=268.

Example 37 Synthesis of Intermediate 19P-IM1

19P-IM1

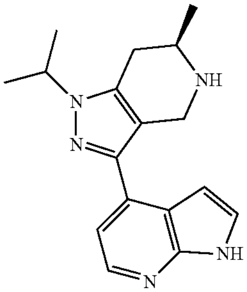

Referring to the synthesis method of the intermediate 180-IM4 in Example 36, the methyl iodide in the step 1 was replaced with 2-iodopropane, and 4 g of an intermediate 19P-IM1 was obtained through a three-step reaction, with a yield of 64%. ESI(M+H)$^+$=296.

Example 38 Synthesis of Intermediate 20Q-IM1

1-4

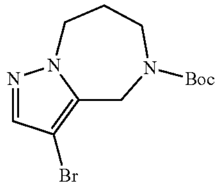

20Q-IM1

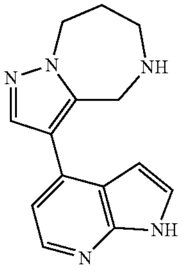

Referring to the synthesis method of the intermediate (R)-1d in Example 1, the (R)-2-aminopropanol was replaced with aminopropanol to obtain the intermediate 1-4, and then referring to the synthesis method of the intermediate (R)-1e-IM3 in Example 15, the (R)-1d was replaced with the intermediate 1-4 to obtain 20Q-IM1, with a yield of 30%, and ESI(M+H)$^+$=254.

Example 39 Synthesis of Intermediate 21R-IM1

1-5

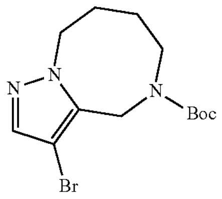

21R-IM1

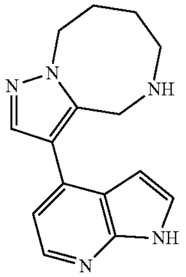

Referring to the synthesis method of intermediate (R)-1d in Example 1, the (R)-2-aminopropanol was replaced with aminobutanol to obtain an intermediate 1-5, and then referring to the synthesis method of the intermediate (R)-1e-IM3 in Example 15, the intermediate (R)-1d was replaced with the intermediate 1-5 to obtain 21R-IM1 with a yield of 34%, and ESI$(M+H)^+$=268.

22S-IM1

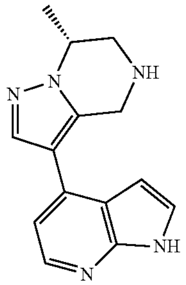

23T-IM1

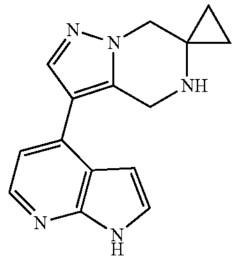

24U-IM1

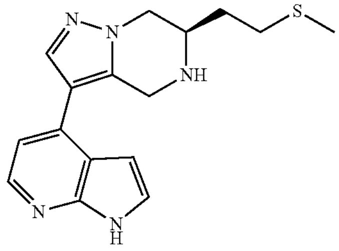

Example 40 Synthesis of Intermediate 22S-IM1

Referring to the synthesis method of intermediate (R)-1d in Example 1, the (R)-2-aminopropanol was replaced with aminobutanol to obtain an intermediate, and then referring to the synthesis method of the intermediate (R)-1e-IM3 in Example 15, the intermediate (R)-1d was replaced with the intermediate(S)-3d to obtain 21R-IM1 with a yield of 34%, and ESI$(M+H)^+$=254.

Example 41 Synthesis of Intermediate 23T-IM1

Referring to the synthesis method of the intermediate (R)-1e-IM3 in Example 15, the intermediate (R)-1d was replaced with 7d to obtain 23T-IM1, with a yield of 24%, and ESI$(M+H)^+$=266.

Example 42 Synthesis of Intermediate 24U-IM1

Referring to the synthesis method of the intermediate (R)-1e-IM3 in Example 15, the intermediate (R)-1d was replaced with 8f to obtain an intermediate 24U-IM1, with a yield of 24%, and ESI$(M+H)^+$=314.

Example 43 Synthesis of Intermediate 25V-IM4

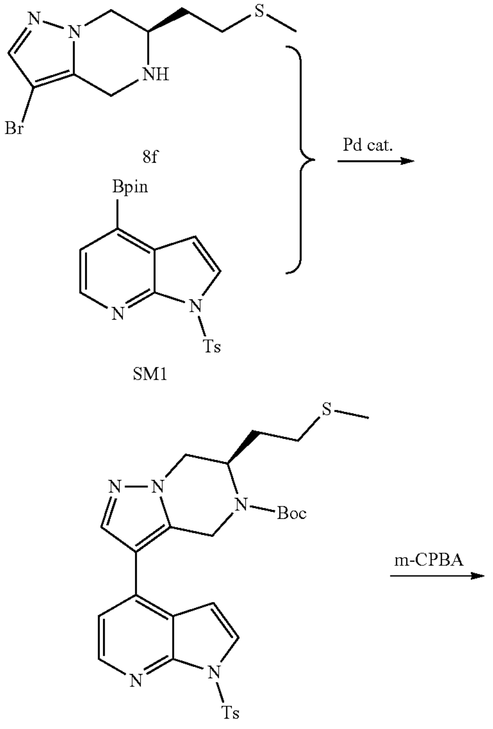

8f

SM1

25V-IM1

-continued

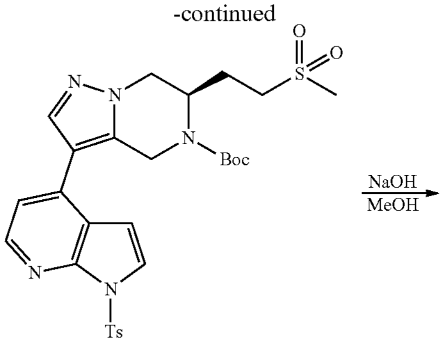

25V-IM2

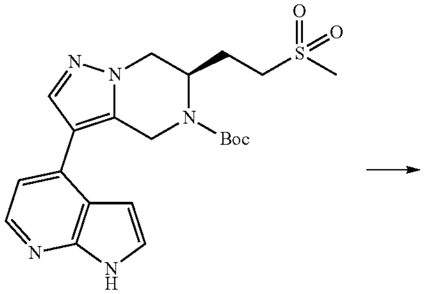

25V-IM3

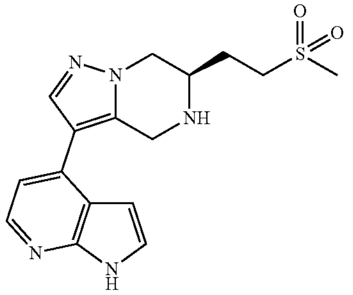

25V-IM4

Step 1: referring to step 1 of Example 15, the intermediate (R)-1d was replaced with the intermediate 8f to obtain an intermediate 25V-IM1, with a yield of 54%, and ESI(M+H)$^+$=568.

Step 2: the intermediate 25V-IM1 (186 mg, 0.33 mmol) was dissolved in DCM, slowly added with m-CPBA (170 mg, 0.98 mmol) under an ice bath, slowly warmed up to room temperature after the addition was completed, and reacted under stirring for 3 h. After the reaction was completed, the reaction was quenched with saturated sodium thiosulfate and sodium bicarbonate solutions, added with water, and extracted with DCM for several times. The organic phases were pooled, dried over a saturated NaCl solution and $Na_2SO_4$, and concentrated under reduced pressure. The obtained crude product was purified by silica gel column chromatography to obtain 158 mg of an intermediate 25V-IM2, with a yield of 82%. ESI(M+H)$^+$=600.

Step 3: referring to step 2 of Example 15, the intermediate (R)-1e-IM1 was replaced with the intermediate 25V-IM2 to obtain an intermediate 25V-IM3, with a yield of 69%, and ESI(M+H)$^+$=446.

Step 4: referring to step 3 of Example 15, the intermediate (R)-1e-IM2 was replaced with the intermediate 25V-IM3 to obtain an intermediate 25V-IM4, with a yield of 73%, and ESI(M+H)$^+$=346.

26W-IM1

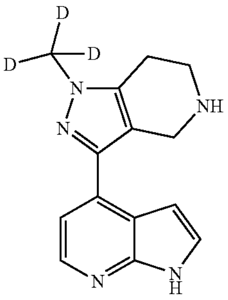

27X-IM1

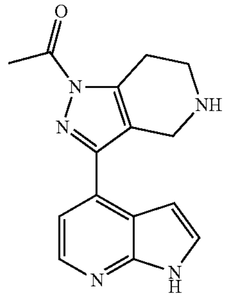

Example 44 Synthesis of Intermediate 26W-IM1

Referring to the synthesis method of the intermediate 9f-IM3 in Example 27, methyl iodide was replaced with deuterated methyl iodide to obtain 26W-IM1, with a yield of 43%, and ESI(M+H)$^+$=257.

Example 45 Synthesis of Intermediate 27X-IM1

Referring to the synthesis method of the intermediate 9f-IM3 in Example 27, methyl iodide was replaced with acetyl chloride to obtain an intermediate 27X-IM1, with a yield of 38%, and ESI(M+H)$^+$=282.

Example 46 Synthesis of Intermediate 28Y-IM3

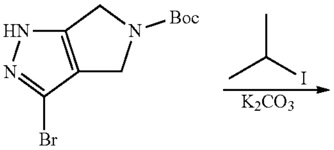

15L-IM2

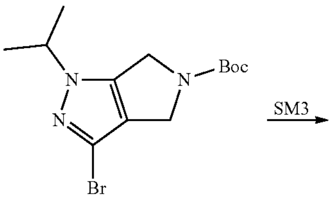

28Y-IM1

-continued

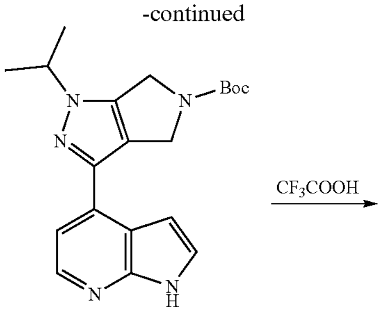

28Y-IM2

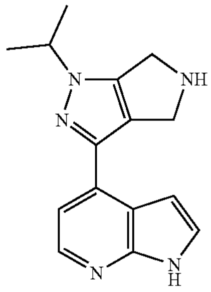

28Y-IM3

Referring to the synthesis method of the intermediate 180-IM4 in Example 36, methyl iodide in step 1 was replaced with 2-iodopropane, and the intermediate 180-IM1 in step 1 was replaced with 15L-IM2. 1.8 g of an intermediate 28Y-IM3 was obtained through a 3-step reaction, with a yield of 24%. ESI(M+H)$^+$=268.

Example 47 Synthesis of Intermediate 29Z-IM3

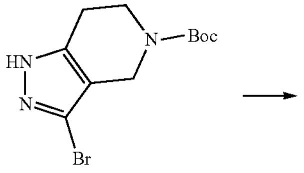

8d-IM3

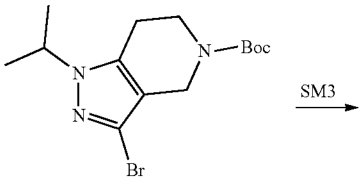

29Z-IM1

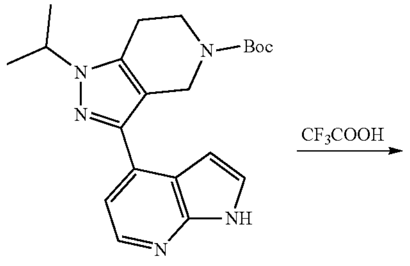

29Z-IM2

-continued

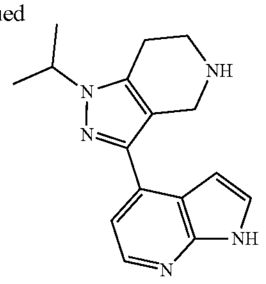

29Z-IM3

Referring to the synthesis method of the intermediate 180-IM4 in Example 36, the intermediate 180-IM1 in step 1 was replaced with 8d-IM3, and 1.3 g of an intermediate 29Z-IM3 was obtained through a 3-step reaction, with a yield of 27%. ESI(M+H)$^+$=282.

Example 48 Synthesis of Intermediate 30A-IM3

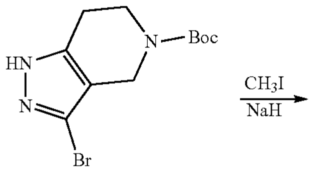

8d-IM3

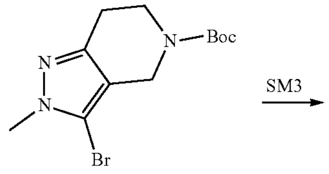

30A-IM1

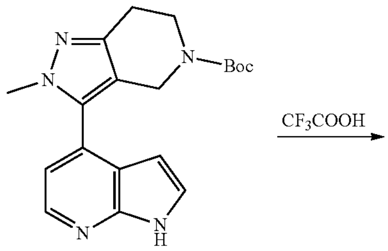

30A-IM2

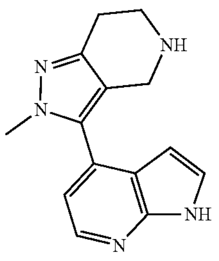

30A-IM3

Step 1: into a 500 mL three-necked flask containing 100 mL of DMF sequentially added were the intermediate 8d-IM3 (10 g, 33.1 mmol), sodium hydrogen (1.59 g, 66.2 mmol), and methyl iodide (9.4 g, 66.2 mmol), and the reaction system was placed at 0° C. and reacted under stirring well for 2 hours. After the reaction was completed, the reaction solution was poured into water, and extracted with dichloromethane for 3 times. The organic layers were pooled, washed twice with a saturated sodium chloride solution, dried over anhydrous sodium sulfate, and concentrated under reduced pressure. The obtained crude product was purified by silica gel column chromatography to obtain 2 g of an intermediate 30A-IM1 as a yellow solid, with a yield of 20%. ESI$(M+H)^+$=316.

Step 2: into a 200 ml three-necked flask containing 100 mL of 1,4-dioxane sequentially added were the intermediate 30A-IM1 (2 g, 6.3 mmol), tetrakis(triphenylphosphorus) palladium (0.7 g, 0.6 mmol), the intermediate SM3 (2.3 g, 9.5 mmol) and potassium carbonate (2.6 g, 18.9 mmol) under the protection of nitrogen, and the reaction system was placed at 95° C. and reacted under stirring well overnight. After the reaction was completed, the reaction solution was cooled to room temperature, poured into 100 mL of water, and extracted with ethyl acetate for 3 times. The organic layers were pooled, washed twice with a saturated sodium chloride solution, dried over anhydrous sodium sulfate, and concentrated under reduced pressure. The obtained crude product was purified by silica gel column chromatography to obtain 1.5 g of an intermediate 30A-IM2 as a light yellow solid, with a yield of 68%, and ESI$(M+H)^+$=354.

Step 3: the intermediate 30A-IM2 (1.5 g, 20.6 mmol) was dissolved in dichloromethane, added with an equal volume of trifluoroacetic acid, reacted at room temperature overnight, adjusted to the pH of 8-9 after the reaction was completed, and extracted with dichloromethane for 3 times. The organic layers were pooled, washed with a saturated sodium chloride solution twice, dried over anhydrous sodium sulfate, and concentrated under reduced pressure. The obtained crude product was purified by silica gel column chromatography to obtain 0.7 g of an intermediate 30A-IM3 as a white solid, with a yield of 70%. ESI$(M+H)^+$=254.

Example 49 Synthesis of Compound YZ001001

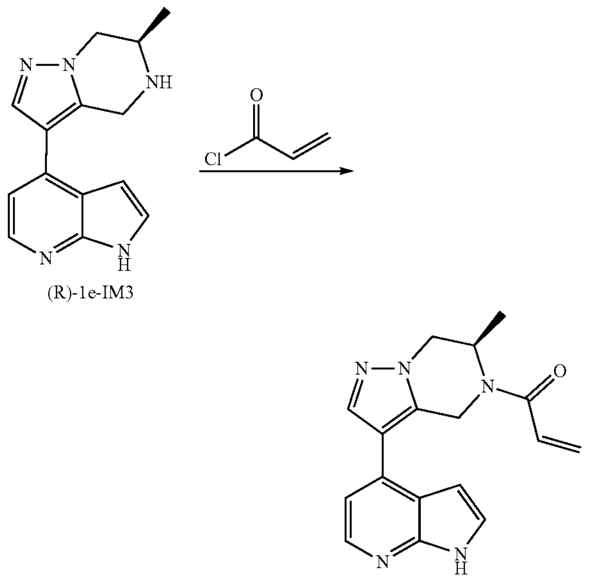

YZ001001

Step: the intermediate (R)-1e-IM3 (100 mg, 0.39 mmol) was dissolved in 20 ml of dichloromethane, then added with triethylamine (119.8 mg, 1.2 mmol), slowly added with acryloyl chloride (42.9 mg, 0.47 mmol) under an ice bath, reacted at room temperature for 3 hours, then added with a saturated aqueous solution of sodium bicarbonate, and washed and extracted with dichloromethane for 3 times. The organic layers were pooled, dried over anhydrous sodium sulfate, and concentrated under reduced pressure. The obtained crude product was purified by silica gel column chromatography to obtain 60 mg of a compound YZ001001 as a white solid, with the yield of 50%. 1H NMR (400 MHz, MeOD) δ 8.22 (d, J=5.1 Hz, 1H), 8.02 (s, 1H), 7.45 (d, J=3.5 Hz, 1H), 7.10 (d, J=5.1 Hz, 1H), 6.87 (s, 1H), 6.64 (d, J=3.5 Hz, 1H), 6.28 (d, J=16.8 Hz, 1H), 5.82 (d, J=10.6 Hz, 1H), 5.40 (s, 1H), 4.87-4.85 (m, 3H), 4.39 (s, 1H), 4.30 (d, J=12.9 Hz, 1H), 1.29 (d, J=6.3 Hz, 3H), ESI$(M+H)^+$=308.

YZ001002

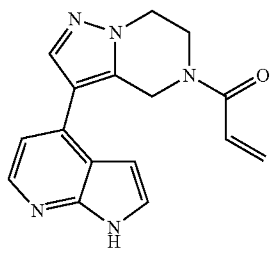

YZ001003

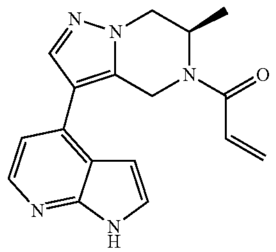

YZ001004

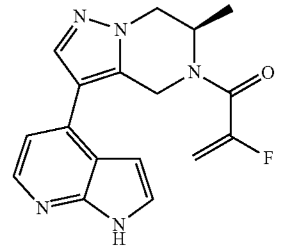

YZ001005

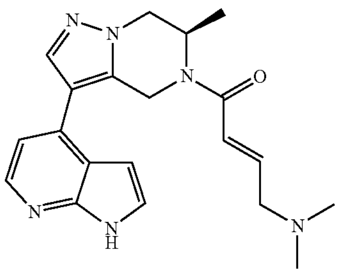

-continued
YZ001006
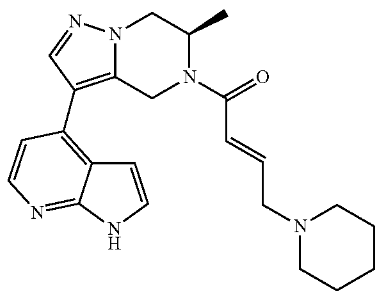
YZ001007
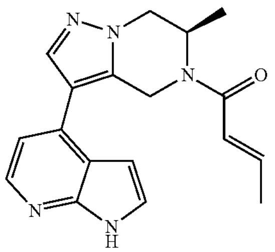
YZ001008
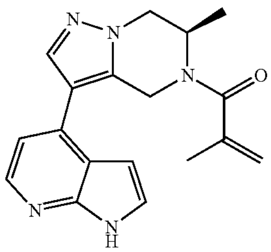
YZ001009
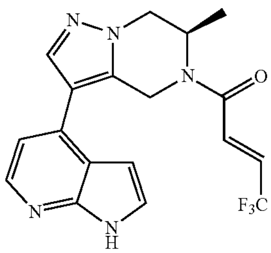
YZ001010
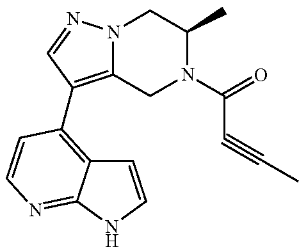
YZ001011
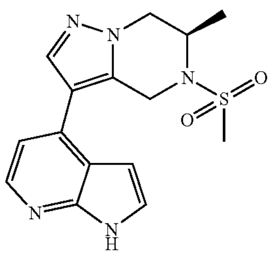
-continued
YZ001012
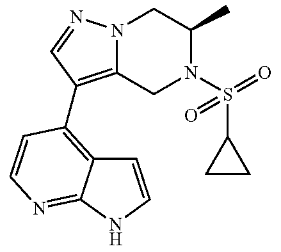
YZ001013
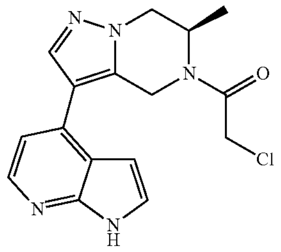
YZ001014
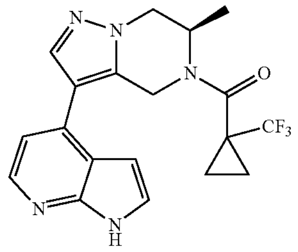
YZ001015
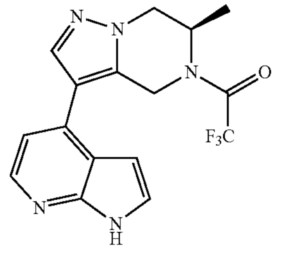
YZ001016
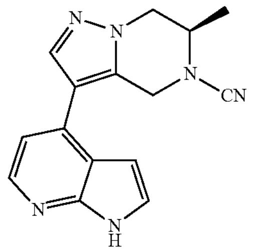
YZ001017
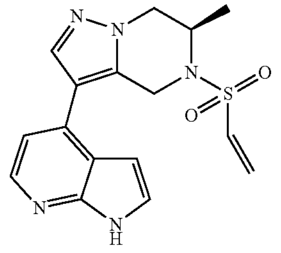

YZ001018
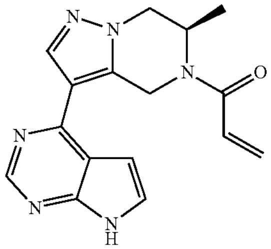
YZ001019
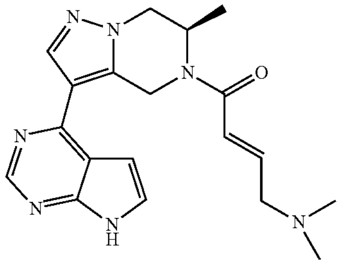
YZ001020
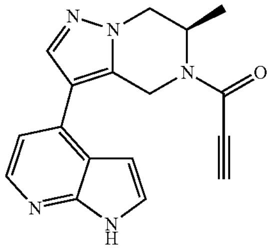
YZ001021
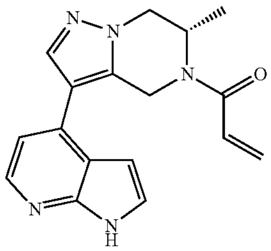
YZ001022
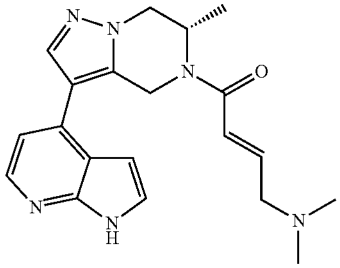
YZ001023
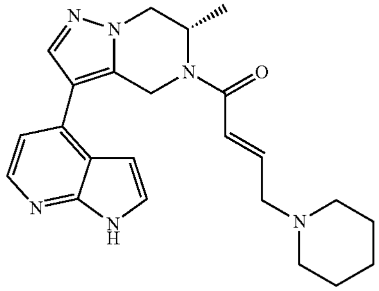
YZ001024
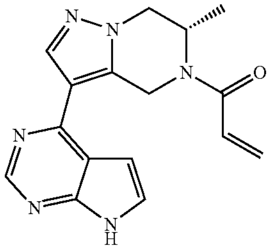
YZ001025
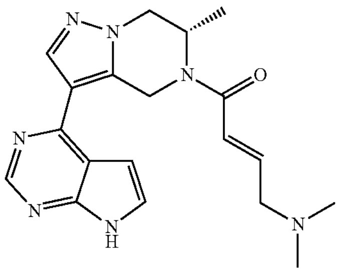
YZ001026
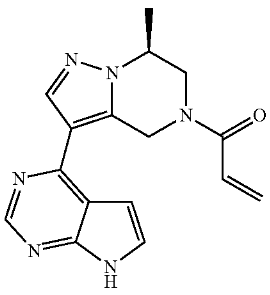
YZ001027
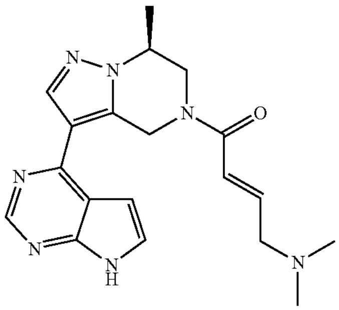
YZ001028
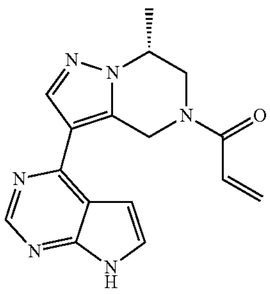

-continued
YZ001029
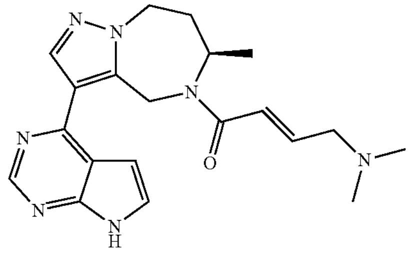
YZ001030
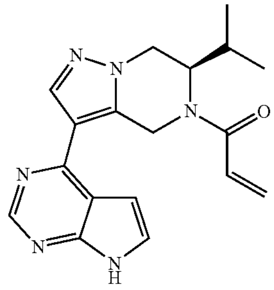
YZ001031
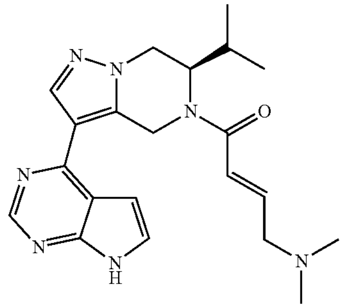
YZ001032
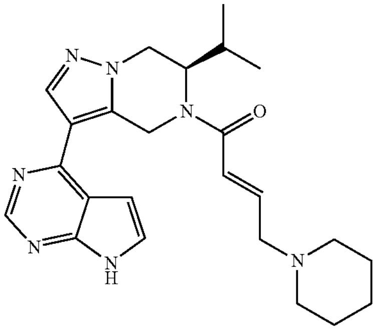
YZ001033
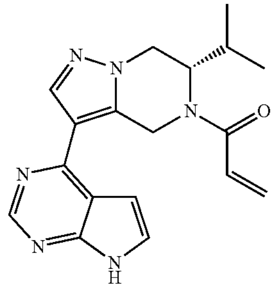
-continued
YZ001034
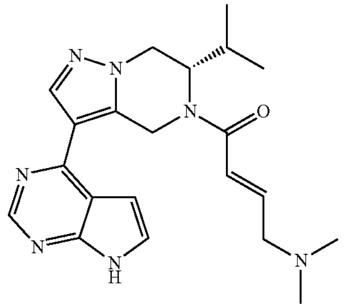
YZ001035
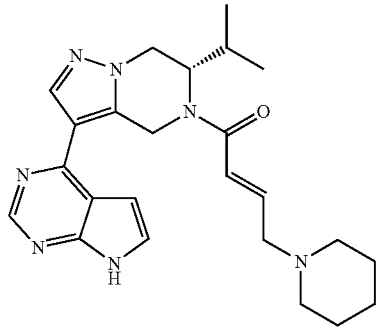
YZ001039
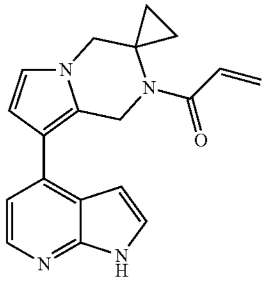
YZ001045
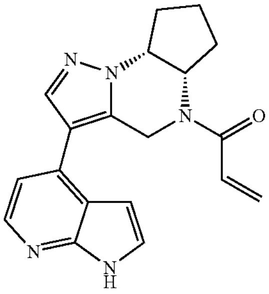
YZ001047
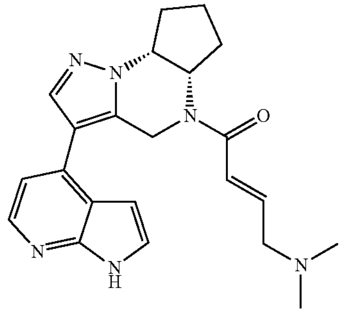

-continued
YZ001048
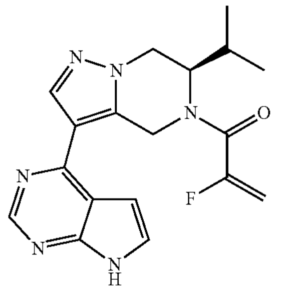
YZ001049
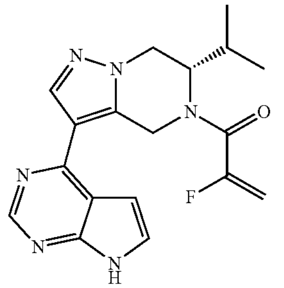
YZ001050
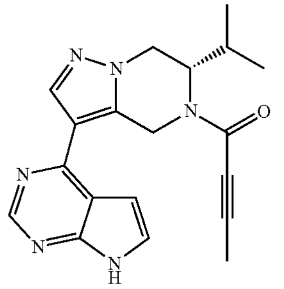
YZ001051
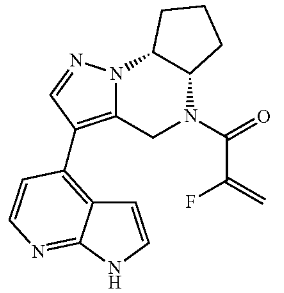
YZ001052
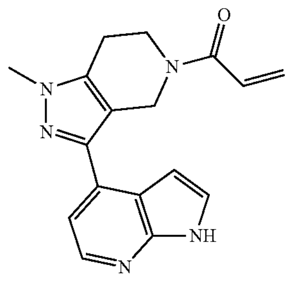
-continued
YZ001053
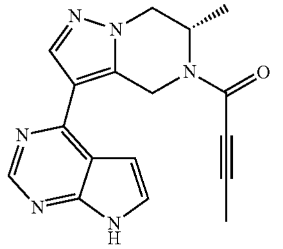
YZ001054
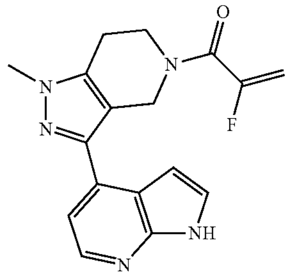
YZ001055
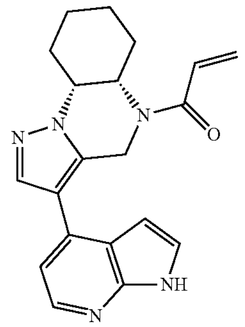
YZ001056
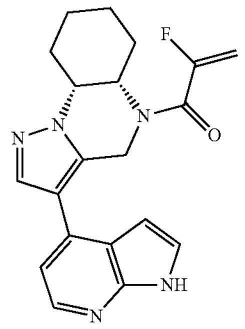
YZ001057
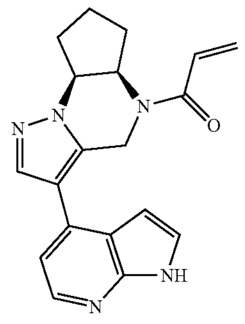

-continued
YZ001058
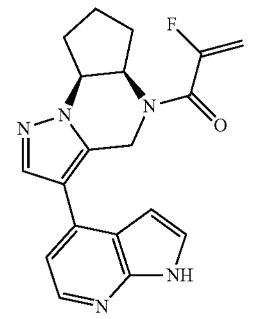
YZ001059
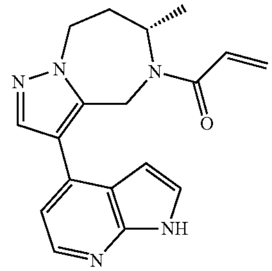
YZ001060
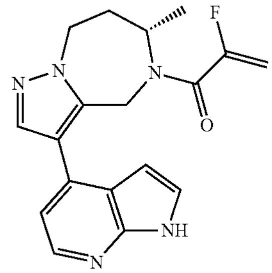
YZ001063
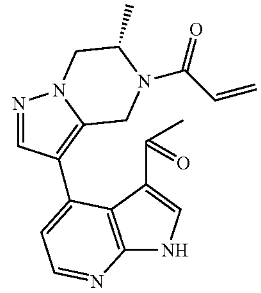
YZ001064
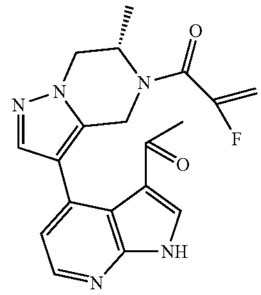
-continued
YZ001065
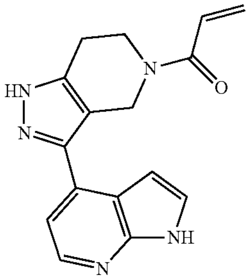
YZ001066
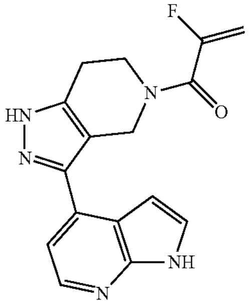
YZ001067
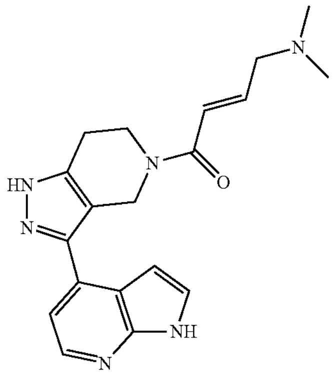
YZ001068
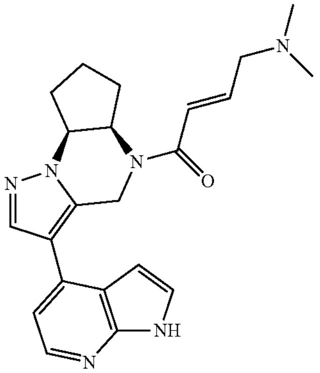
YZ001069
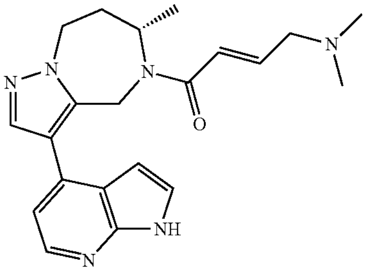

YZ001070
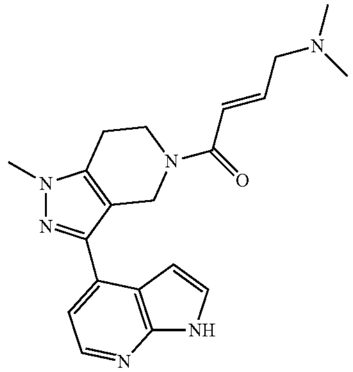
YZ001071
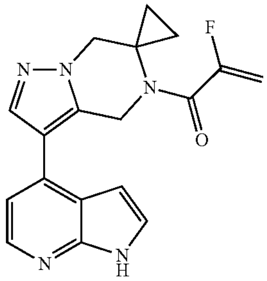
YZ001072
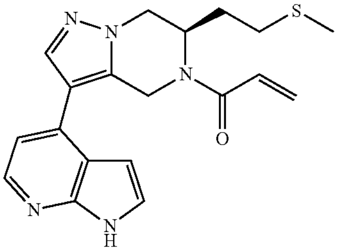
YZ001073
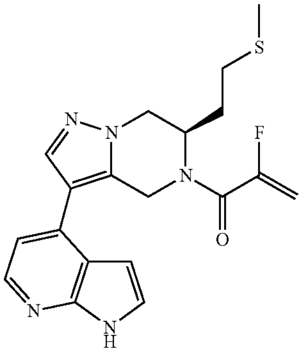
YZ001074
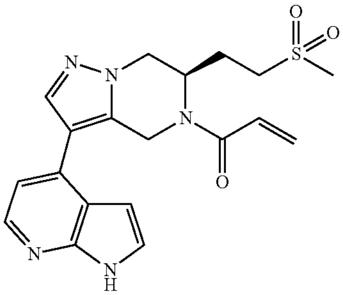
YZ001075
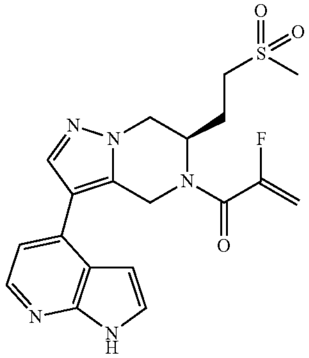
YZ001076
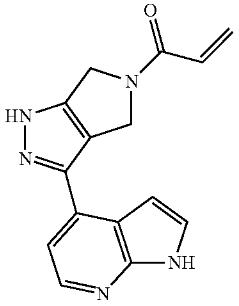
YZ001077
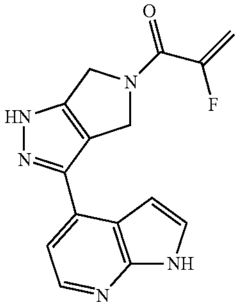
YZ001083
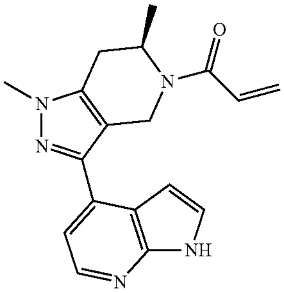
YZ001084
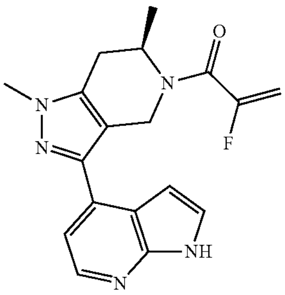

-continued
YZ001085
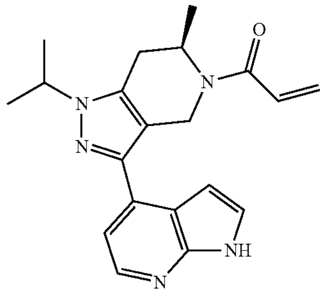
YZ001086
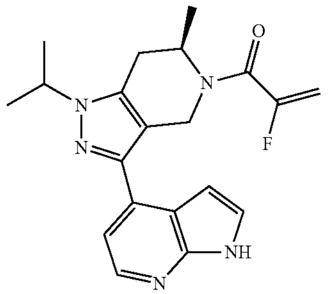
YZ001087
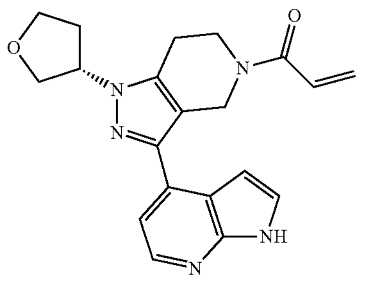
YZ001088
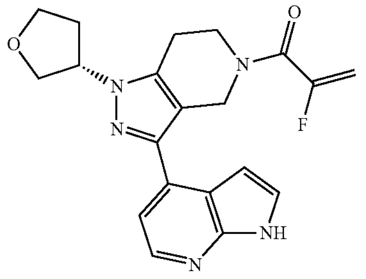
YZ001091
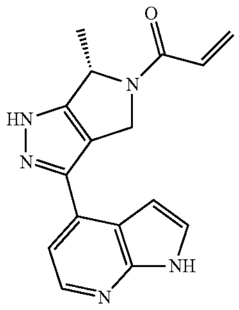
-continued
YZ001093
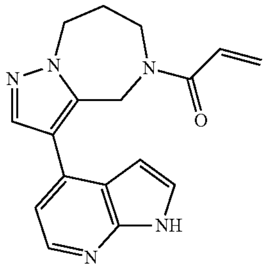
YZ001094
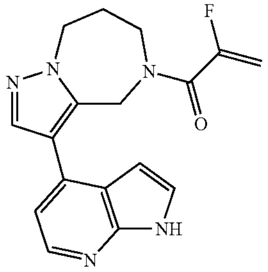
YZ001095
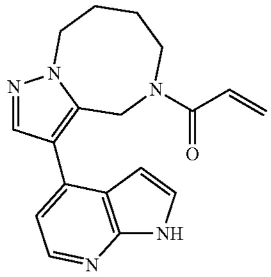
YZ001096
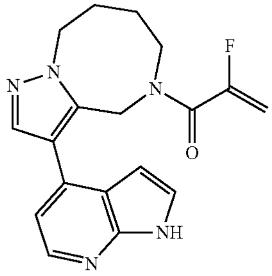
YZ001099
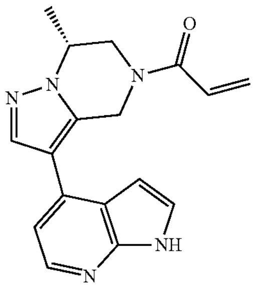

-continued

YZ001100

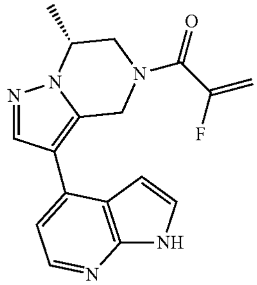

YZ001103

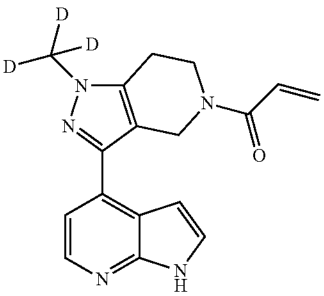

YZ001104

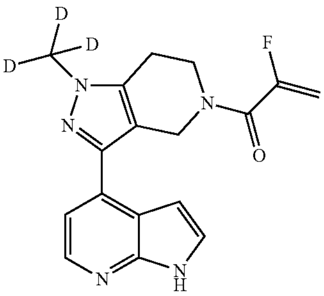

YZ001107

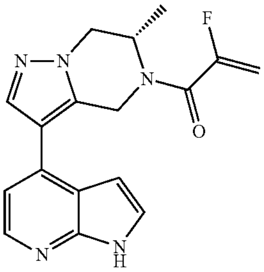

YZ001108

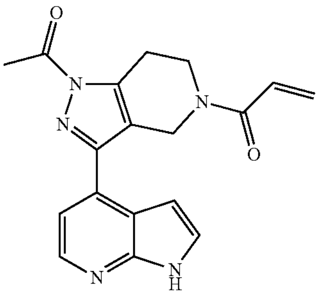

-continued

YZ001109

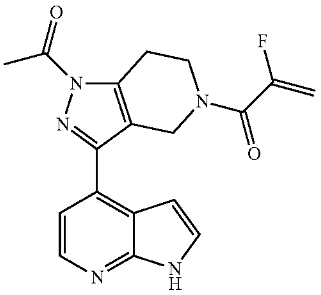

YZ001115

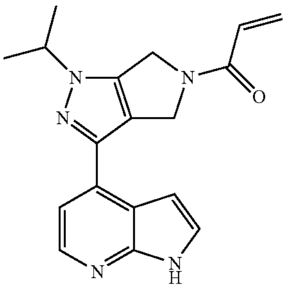

YZ001117

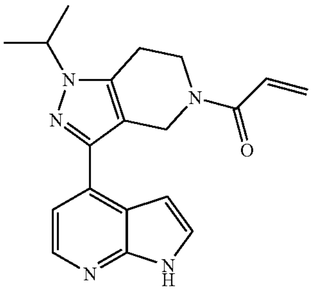

YZ001118

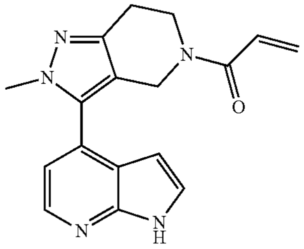

Example 50 Synthesis of Compound YZ001002

Referring to the steps of Example 49, the intermediate (R)-1e-IM3 in Example 49 was replaced with the intermediate 2e-IM3, so as to obtain a compound YZ001002, with a yield of 47%. 1H NMR (400 MHz, MeOD) δ 8.25 (d, J=5.1 Hz, 1H), 8.02 (s, 1H), 7.48 (d, J=3.5 Hz, 1H), 7.09 (d, J=5.0 Hz, 1H), 7.02-6.73 (m, 1H), 6.68 (d, J=2.9 Hz, 1H), 6.39-6.24 (m, 1H), 5.95-5.74 (m, 1H), 5.17-5.06 (m, 2H), 4.43-4.32 (m, 2H), 4.30-4.21 (m, 2H), ESI$(M+H)^+$=294.

Example 51 Synthesis of Compound YZ001003

Referring to the steps of Example 49, the acryloyl chloride in Example 49 was replaced with acetyl chloride to obtain a compound YZ001003, with a yield of 50%. 1H NMR (400 MHz, MeOD) δ 8.24 (d, J=4.5 Hz, 1H), 8.05 (s, 1H), 7.52-7.44 (m, 1H), 7.16-7.07 (m, 1H), 6.67 (d, J=3.5

Hz, 1H), 5.56-4.89 (m, 2H), 4.82-4.73 (m, 1H), 4.55-4.27 (m, 2H), 2.25 (d, J=38.1 Hz, 3H), 1.39-1.26 (m, 3H)., ESI(M+H)$^+$=296.

Example 52 Synthesis of Compound YZ001004

Step: the intermediate (R)-1e-IM3 (100 mg, 0.39 mmol) was dissolved in 20 ml of dichloromethane, then added with N,N-diisopropylethylamine (204.1 mg, 1.6 mmol), 2-(7-azabenzotriazole)-N,N,N',N'-tetramethylurea hexafluorophosphate (195.1 mg, 0.51 mmol), 2-fluoroacrylic acid (46.2 mg, 0.51 mmol), reacted at room temperature for 3 hours, then added with a saturated aqueous solution of sodium bicarbonate, and washed and extracted with dichloromethane for 3 times. The organic layers were pooled, dried over anhydrous sodium sulfate, and concentrated under reduced pressure. The obtained crude product was purified by silica gel column chromatography to obtain 80 mg of a compound YZ001004 as a white solid, with a yield of 66%. 1H NMR (400 MHz, DMSO-d6) δ 11.77 (s, 1H), 8.27 (d, J=4.9 Hz, 1H), 8.07 (s, 1H), 7.55-7.47 (m, 1H), 7.05 (d, J=5.0 Hz, 1H), 6.65 (dd, J=3.4, 1.8 Hz, 1H), 5.42 (s, 1H), 5.34 (dd, J=32.2, 4.2 Hz, 1H), 4.91 (s, 1H), 4.35 (dt, J=38.6, 8.6 Hz, 2H), 2.72 (s, 2H), 1.30 (s, 3H), ESI(M+H)$^+$=326.

Example 53 Synthesis of Compound YZ001005

Referring to the steps of Example 52, 2-fluoroacrylic acid in Example 52 was replaced with trans-4-dimethylamino crotonate hydrochloride to obtain a compound YZ001005, with a yield of 52%. 1H NMR (400 MHz, DMSO-d6) δ 11.76 (s, 1H), 8.26 (d, J=4.9 Hz, 1H), 8.05 (s, 1H), 7.57-7.49 (m, 1H), 7.07 (s, 1H), 6.64 (dd, J=3.4, 1.8 Hz, 1H), 5.31 (d, J=17.0 Hz, 1H), 4.92 (s, 1H), 4.60 (s, 2H), 4.28 (s, 2H), 3.19 (d, J=9.6 Hz, 1H), 3.08 (s, 2H), 2.18 (d, J=1.4 Hz, 6H), 1.23 (s, 3H), ESI(M+H)$^+$=365.

Example 54 Synthesis of Compound YZ001006

Referring to the steps of Example 52, 2-fluoroacrylic acid in Example 52 was replaced with (2E)-4-(1-piperidinyl)-2-butenoic acid to obtain a compound YZ001006, with a yield of 80%. 1H NMR (400 MHz, DMSO-d6) δ 11.75 (s, 1H), 8.26 (d, J=4.9 Hz, 1H), 8.05 (s, 1H), 7.58-7.44 (m, 1H), 7.07 (d, J=4.2 Hz, 1H), 6.74-6.60 (m, 2H), 5.30 (d, J=17.1 Hz, 1H), 4.91 (s, 1H), 4.60 (s, 1H), 4.27 (d, J=12.3 Hz, 2H), 3.14 (s, 2H), 2.36 (d, J=1.9 Hz, 4H), 1.52 (s, 4H), 1.41 (s, 3H), 1.23 (d, J=6.2 Hz, 2H), ESI(M+H)$^+$=405.

Example 55 Synthesis of Compound YZ001007

Referring to the steps of Example 52, 2-fluoroacrylic acid in Example 52 was replaced with (E)-but-2-enoic acid to obtain a compound YZ001007, with a yield of 70%. 1H NMR (400 MHz, DMSO-d6) δ 11.75 (s, 1H), 8.26 (dd, J=4.9, 2.5 Hz, 1H), 8.06 (d, J=4.7 Hz, 1H), 7.55-7.50 (m, 1H), 7.08 (s, 1H), 6.79 (dd, J=14.8, 6.7 Hz, 1H), 6.65 (dd, J=3.4, 1.8 Hz, 2H), 5.41-5.06 (m, 2H), 4.71 (dd, J=12.8, 5.2 Hz, 1H), 4.26 (d, J=12.3 Hz, 2H), 1.89 (d, J=6.2 Hz, 3H), 1.22 (s, 3H), ESI(M+H)$^+$=322.

Example 56 Synthesis of Compound YZ001008

Referring to the steps of Example 52, 2-fluoroacrylic acid in Example 52 was replaced with 2-methacrylic acid to obtain a compound YZ001008, with a yield of 68%. 1H NMR (400 MHz, DMSO-d6) δ 11.75 (s, 1H), 8.25 (d, J=4.9 Hz, 1H), 8.06 (s, 1H), 7.52 (t, J=2.9 Hz, 1H), 7.04 (d, J=4.9 Hz, 1H), 6.64 (dd, J=3.2, 1.7 Hz, 1H), 5.28 (s, 1H), 5.16 (s, 1H), 4.93-4.56 (m, 2H), 4.48-4.36 (m, 1H), 4.28 (dd, J=40.4, 8.4 Hz, 2H), 1.93 (s, 3H), 1.30 (d, J=6.9 Hz, 3H), ESI(M+H)$^+$=322.

Example 57 Synthesis of Compound YZ001009

Referring to the steps of Example 52, 2-fluoroacrylic acid in Example 52 was replaced with 4,4,4-trifluorobutenoic acid to obtain a compound YZ001009, with a yield of 78%. 1H NMR (400 MHz, DMSO-d6) δ 11.76 (s, 1H), 8.27 (d, J=4.6 Hz, 1H), 8.06 (s, 1H), 7.52 (s, 2H), 7.06 (d, J=4.6 Hz, 1H), 6.85 (dd, J=15.4, 7.1 Hz, 1H), 6.64 (dd, J=3.4, 1.8 Hz, 1H), 5.36 (d, J=17.9 Hz, 1H), 4.90 (s, 1H), 4.45 (dt, J=70.9, 15.2 Hz, 2H), 1.27 (d, J=6.4 Hz, 3H), ESI(M+H)$^+$=376.

Example 58 Synthesis of Compound YZ001010

Referring to the steps of Example 52, 2-fluoroacrylic acid in Example 52 was replaced with 2-butynoic acid to obtain a compound YZ001010, with a yield of 58%. 1H NMR (400 MHz, DMSO-d6) δ 11.76 (s, 1H), 8.27 (dd, J=7.4, 5.0 Hz, 1H), 8.07 (s, 1H), 7.53 (dd, J=7.3, 4.4 Hz, 1H), 7.05 (t, J=5.1 Hz, 1H), 6.65 (dd, J=3.2, 1.8 Hz, 1H), 5.34 (dd, J=50.6, 17.3 Hz, 1H), 5.16-5.08 (m, 1H), 4.58 (d, J=17.8 Hz, 1H), 4.46-4.20 (m, 2H), 2.12 (s, 3H), 1.28 (d, J=6.2 Hz, 3H), ESI(M+H)$^+$=320.

Example 59 Synthesis of Compound YZ001011

Referring to the steps of Example 49, the acryloyl chloride in Example 49 was replaced with methanesulfonyl chloride to obtain a compound YZ001011, with a yield of 40%. 1H NMR (400 MHz, DMSO-d6) δ 11.76 (s, 1H), 8.26 (d, J=4.9 Hz, 1H), 8.08 (s, 1H), 7.59-7.43 (m, 1H), 7.05 (d, J=5.0 Hz, 1H), 6.66 (dd, J=3.4, 1.8 Hz, 1H), 4.81 (dd, J=39.0, 16.6 Hz, 2H), 4.57 (s, 1H), 4.42-4.17 (m, 2H), 3.11 (s, 3H), 1.33 (d, J=6.9 Hz, 3H), ESI(M+H)$^+$=332.

Example 60 Synthesis of Compound YZ001012

Referring to the steps of Example 49, the acryloyl chloride in Example 49 was replaced with cyclopropanesulfonyl chloride to obtain a compound YZ001012, with a yield of 46%. 1H NMR (400 MHz, DMSO-d6) δ 11.77 (s, 1H), 8.26 (d, J=4.9 Hz, 1H), 8.08 (s, 1H), 7.57-7.50 (m, 1H), 7.04 (d, J=5.0 Hz, 1H), 6.66 (dd, J=3.4, 1.8 Hz, 1H), 4.83 (s, 2H), 4.57 (dd, J=8.7, 3.4 Hz, 1H), 4.40 (dd, J=13.0, 5.0 Hz, 2H), 2.86-2.77 (m, 1H), 1.39 (d, J=6.9 Hz, 3H), 1.06-0.98 (m, 2H), 0.96-0.86 (m, 2H), ESI(M+H)$^+$=358.

Example 61 Synthesis of Compound YZ001013

Referring to the steps of Example 49, acryloyl chloride in Example 49 was replaced with chloroacetyl chloride to obtain a compound YZ001013, with a yield of 53%. 1H NMR (400 MHz, DMSO-d6) δ 11.76 (s, 1H), 8.26 (d, J=4.6 Hz, 1H), 8.07 (s, 1H), 7.53 (s, 1H), 7.07 (s, 1H), 6.66 (s, 1H), 5.79 (s, 1H), 5.34 (s, 1H), 5.16 (s, 1H), 4.63 (d, J=6.7 Hz, 1H), 4.53 (s, 1H), 4.28 (s, 2H), 1.29 (d, J=24.6 Hz, 3H), ESI(M+H)$^+$=330.

Example 62 Synthesis of Compound YZ001014

Referring to the steps of Example 52, 2-fluoroacrylic acid in Example 52 was replaced with 1-trifluoromethylcyclopropane-1-carboxylic acid to obtain a compound YZ001014, with a yield of 52%. 1H NMR (400 MHz, DMSO-d6) δ 11.77 (s, 1H), 8.26 (d, J=4.9 Hz, 1H), 8.08 (s, 1H), 7.56-7.51 (m, 1H), 7.05 (d, J=5.0 Hz, 1H), 6.65 (dd, J=3.4, 1.8 Hz, 1H), 5.38 (d, J=17.5 Hz, 1H), 5.20-5.06 (m, 1H), 4.68 (s, 1H), 4.36 (d, J=9.1 Hz, 1H), 4.26 (d, J=12.7 Hz, 1H), 1.39 (s, 4H), 1.36 (s, 3H), ESI(M+H)$^+$=390.

Example 63 Synthesis of Compound YZ001015

Referring to the steps of Example 52, 2-fluoroacrylic acid in Example 52 was replaced with trifluoroacetic acid to obtain a compound YZ001015, with a yield of 65%, 1H NMR (400 MHz, DMSO-d6) δ 11.71 (d, J=62.5 Hz, 1H), 8.27 (d, J=4.9 Hz, 1H), 8.08 (d, J=8.3 Hz, 1H), 7.54 (d, J=2.5 Hz, 1H), 7.04 (dd, J=19.1, 4.9 Hz, 1H), 6.64 (d, J=11.8 Hz, 1H), 5.32 (d, J=17.7 Hz, 1H), 5.11 (dd, J=52.8, 16.5 Hz, 1H), 4.77 (d, J=10.0 Hz, 1H), 4.44 (dd, J=13.1, 4.1 Hz, 1H), 4.33 (dd, J=13.1, 6.9 Hz, 1H), 1.32 (t, J=9.4 Hz, 3H), ESI(M+H)$^+$=350.

Example 64 Synthesis of Compound YZ001016

Referring to the steps of Example 52, 2-fluoroacrylic acid in Example 52 was replaced with bromonitrile to obtain a compound YZ001016, with a yield of 75%, 1H NMR (400 MHz, DMSO-$d_6$) δ 11.77 (s, 1H), 8.26 (t, J=11.7 Hz, 1H), 8.08 (s, 1H), 7.56-7.46 (m, 1H), 7.00 (t, J=5.9 Hz, 1H), 6.66 (dd, J=3.3, 1.7 Hz, 1H), 4.91 (dd, J=38.5, 16.2 Hz, 2H), 4.47 (dt, J=9.6, 4.8 Hz, 1H), 4.11-4.00 (m, 1H), 3.94 (ddd, J=15.5, 7.8, 4.6 Hz, 1H), 1.46 (t, J=5.4 Hz, 3H), ESI(M+H)$^+$=279.

Example 65 Synthesis of Compound YZ001017

Referring to the steps of Example 49, acryloyl chloride in Example 49 was replaced with propenesulfonyl chloride to obtain a compound YZ001017, with a yield of 43%. 1H NMR (400 MHz, DMSO-$d_6$) δ 11.70 (d, J=59.9 Hz, 1H), 8.25 (t, J=5.3 Hz, 1H), 8.07 (s, 1H), 7.66 (t, J=6.0 Hz, 1H), 7.63 (s, 1H), 7.61-7.57 (m, 1H), 7.01 (dd, J=12.4, 6.9 Hz, 1H), 6.21-6.16 (m, 1H), 6.11 (d, J=9.9 Hz, 1H), 4.80-4.72 (m, 2H), 4.56-4.47 (m, 1H), 4.35 (dd, J=13.0, 4.9 Hz, 1H), 4.26-4.15 (m, 1H), 1.31 (t, J=8.3 Hz, 3H), ESI(M+H)$^+$=344.

Example 66 Synthesis of Compound YZ001018

Referring to the steps of Example 49, the intermediate (R)-1e-IM3 in Example 49 was replaced with the intermediate (R)-3e-IM3 to obtain a compound YZ001018, with a yield of 59%. 1H NMR (400 MHz, DMSO-$d_6$) δ 12.13 (s, 1H), 8.76 (s, 1H), 8.48 (s, 1H), 7.60-7.56 (m, 1H), 7.03 (dd, J=3.4, 1.6 Hz, 1H), 6.22 (dd, J=16.7, 2.1 Hz, 1H), 5.81 (d, J=10.5 Hz, 2H), 4.95 (s, 1H), 4.73 (d, J=7.5 Hz, 1H), 4.38 (s, 1H), 4.26 (d, J=12.7 Hz, 1H), 1.20 (d, J=5.6 Hz, 3H), ESI(M+H)$^+$=309.

Example 64 Synthesis of Compound YZ001019

Referring to the steps of Example 52, 2-fluoroacrylic acid in Example 52 was replaced with trans-4-dimethylamino crotonate hydrochloride, and (R)-1e-IM3 was replaced with (R)-3e-IM3 to obtain a compound YZ001019, with a yield of 76%. 1H NMR (400 MHz, DMSO-$d_6$) δ 12.13 (s, 1H), 8.75 (s, 1H), 8.47 (s, 1H), 7.60-7.50 (m, 1H), 7.03 (d, J=2.2 Hz, 1H), 6.71 (d, J=5.2 Hz, 2H), 5.70 (s, 1H), 4.92 (s, 1H), 4.79-4.63 (m, 1H), 4.38 (s, 1H), 4.28 (s, 1H), 3.10 (d, J=4.0 Hz, 2H), 2.21 (s, 6H), 1.20 (d, J=6.1 Hz, 3H), ESI(M+H)$^+$=366.

Example 68 Synthesis of Compound YZ001020

Referring to the steps of Example 52, 2-fluoroacrylic acid in Example 52 was replaced with propynoic acid to obtain a compound YZ001020, with a yield of 80%. 1H NMR (400 MHz, $CDCl_3$) δ 11.74 (s, 1H), 8.23 (d, J=3.3 Hz, 1H), 8.04 (s, 1H), 7.56 (dd, J=9.5, 5.3 Hz, 1H), 7.51 (d, J=2.6 Hz, 1H), 7.02 (d, J=4.9 Hz, 1H), 6.62 (s, 1H), 5.24 (d, J=17.8 Hz, 1H), 4.60 (dd, J=38.5, 20.8 Hz, 1H), 4.48-4.20 (m, 2H), 3.14 (s, 1H), 1.30 (s, 3H), ESI(M+H)$^+$=306.

Example 69 Synthesis of Compound YZ001021

Referring to the steps of Example 49, the intermediate (R)-1e-IM3 in Example 49 was replaced with the intermediate(S)-1e-IM3 to obtain a compound YZ001021, with a yield of 78%. 1H NMR (400 MHz, DMSO-$d_6$) δ 11.72 (d, J=34.0 Hz, 1H), 8.27 (d, J=4.9 Hz, 1H), 8.06 (s, 2H), 7.54-7.51 (m, 1H), 7.08 (s, 1H), 6.66 (dd, J=3.2, 1.7 Hz, 1H), 6.19 (dt, J=24.2, 12.1 Hz, 1H), 5.77 (dd, J=17.3, 13.3 Hz, 1H), 5.33 (d, J=17.2 Hz, 1H), 4.98 (dd, J=13.6, 7.1 Hz, 2H), 4.28 (d, J=12.2 Hz, 2H), 1.16 (d, J=6.6 Hz, 3H), ESI(M+H)$^+$=308.

Example 70 Synthesis of Compound YZ001022

Referring to the steps of Example 49, the intermediate (R)-1e-IM3 in Example 49 was replaced with the intermediate(S)-1e-IM3, and acryloyl chloride was replaced with trans-4-dimethylamino crotonate hydrochloride to obtain a compound YZ001022, with a yield of 82%. 1H NMR (400 MHz, DMSO-$d_6$) δ 11.85-11.49 (m, 1H), 8.26 (m, 1H), 8.06 (d, J=6.6 Hz, 1H), 7.56-7.49 (m, 1H), 7.08 (s, 1H), 6.70 (d, J=5.3 Hz, 2H), 6.65 (dd, J=3.4, 1.8 Hz, 1H), 5.32 (d, J=16.8 Hz, 1H), 4.92 (s, 1H), 4.38 (d, J=7.2 Hz, 1H), 4.27 (d, J=12.5 Hz, 1H), 3.07 (s, 2H), 2.24-2.13 (m, 6H), 1.28-1.18 (m, 3H), ESI(M+H)$^+$=365.

Example 71 Synthesis of Compound YZ001023

Referring to the steps of Example 49, the intermediate (R)-1e-IM3 in Example 49 was replaced with the intermediate(S)-1e-IM3, and acryloyl chloride was replaced with (2E)-4-(1-piperidinyl)-2-butenoic acid to obtain a compound YZ001023, with a yield of 86%. 1H NMR (400 MHz, DMSO-$d_6$) δ 11.80-11.64 (m, 1H), 8.26 (d, J=4.9 Hz, 1H), 8.01 (d, J=35.2 Hz, 1H), 7.58-7.48 (m, 1H), 7.06 (d, J=4.2 Hz, 1H), 6.70 (s, 2H), 6.64 (dd, J=3.4, 1.8 Hz, 1H), 5.30 (d, J=17.0 Hz, 1H), 4.90 (s, 1H), 4.52 (d, J=53.5 Hz, 1H), 4.36 (s, 1H), 4.28 (s, 1H), 3.11 (s, 2H), 2.36 (s, 4H), 1.50 (s, 4H), 1.40 (s, 2H), 1.26-1.18 (m, 3H), ESI(M+H)$^+$=405.

Example 72 Synthesis of Compound YZ001024

Referring to the steps of Example 49, the intermediate (R)-1e-IM3 in Example 49 was replaced with the intermediate(S)-3e-IM3 to obtain a compound YZ001024, with the yield of 48%. 1H NMR (400 MHz, DMSO-$d_6$) δ 12.07 (d, J=53.5 Hz, 1H), 8.76 (s, 1H), 8.53 (d, J=36.6 Hz, 1H), 7.63 (d, J=30.5 Hz, 1H), 6.99 (d, J=35.4 Hz, 1H), 6.18 (t, J=30.5 Hz, 1H), 5.80 (d, J=19.6 Hz, 2H), 4.94 (s, 1H), 4.74 (s, 1H), 4.34 (d, J=28.4 Hz, 1H), 4.27 (d, J=11.7 Hz, 1H), 1.22 (d, J=14.8 Hz, 3H), ESI$(M+H)^+$=309.

Example 73 Synthesis of Compound YZ001025

Referring to the steps of Example 52, 2-fluoroacrylic acid in Example 52 was replaced with trans-4-dimethylamino crotonate hydrochloride, and (R)-1e-IM3 was replaced with (S)-3e-IM3 to obtain a compound YZ001025, with a yield of 66%. 1H NMR (400 MHz, DMSO-$d_6$) δ 12.13 (s, 1H), 8.85 (s, 1H), 8.57 (s, 1H), 7.60-7.40 (m, 1H), 7.13 (d, J=2.2 Hz, 1H), 6.61 (d, J=5.2 Hz, 2H), 5.60 (s, 1H), 4.92 (s, 1H), 4.79-4.63 (m, 1H), 4.38 (s, 1H), 4.38 (s, 1H), 3.20 (d, J=4.0 Hz, 2H), 2.31 (s, 6H), 1.40 (d, J=6.3 Hz, 3H), ESI$(M+H)^+$=366.

Example 74 Synthesis of Compound YZ001026

Referring to the steps of Example 49, the intermediate (R)-1e-IM3 in Example 49 was replaced with the intermediate (R)-4e-IM3 to obtain a compound YZ001026, with the yield of 58%. 1H NMR (400 MHz, DMSO-$d_6$) δ 12.21 (s, 1H), 8.76 (s, 1H), 8.45 (s, 1H), 7.63-7.50 (m, 1H), 7.01 (dd, J=3.4, 1.5 Hz, 1H), 6.26 (d, J=16.8 Hz, 1H), 5.82 (dd, J=10.5, 2.1 Hz, 1H), 5.28 (d, J=11.8 Hz, 1H), 4.52 (s, 1H), 4.24 (d, J=10.8 Hz, 1H), 4.11 (d, J=16.0 Hz, 1H), 3.99 (d, J=5.9 Hz, 1H), 1.49 (d, J=6.1 Hz, 3H), ESI$(M+H)^+$=309.

Example 75 Synthesis of Compound YZ001027

Referring to the steps of Example 52, 2-fluoroacrylic acid in Example 52 was replaced with trans-4-dimethylamino crotonate hydrochloride, and (R)-1e-IM3 was replaced with (R)-4e-IM3 to obtain a compound YZ001027, with a yield of 76%. 1H NMR (400 MHz, DMSO-$d_6$) δ 12.15 (s, 1H), 8.76 (s, 1H), 8.45 (s, 1H), 7.59 (s, 1H), 7.02 (d, J=2.7 Hz, 1H), 6.89-6.64 (m, 2H), 5.41-5.21 (m, 2H), 4.52 (s, 1H), 4.23 (d, J=12.4 Hz, 1H), 3.95 (dd, J=14.0, 5.9 Hz, 1H), 3.18 (d, J=4.8 Hz, 2H), 2.25 (s, 6H), 1.50 (d, J=6.0 Hz, 3H), ESI$(M+H)^+$=366.

Example 76 Synthesis of Compound YZ001028

Referring to the steps of Example 49, the intermediate (R)-1e-IM3 in Example 49 was replaced with the intermediate(S)-4e-IM3 to obtain a compound YZ001026, with the yield of 58%. 1H NMR (400 MHz, DMSO-$d_6$) δ 12.21 (s, 1H), 8.76 (s, 1H), 8.45 (s, 1H), 7.64-7.51 (m, 1H), 7.01 (d, J=1.9 Hz, 1H), 6.26 (d, J=16.6 Hz, 1H), 5.82 (dd, J=10.4, 2.1 Hz, 1H), 5.28 (d, J=11.8 Hz, 1H), 4.52 (s, 1H), 4.24 (d, J=11.7 Hz, 1H), 4.11 (d, J=11.4 Hz, 1H), 3.97 (dd, J=14.1, 5.8 Hz, 1H), 3.61 (d, J=4.1 Hz, 1H), 1.49 (d, J=6.2 Hz, 3H), ESI$(M+H)^+$=309.

Example 77 Synthesis of Compound YZ001029

Referring to the steps of Example 52, 2-fluoroacrylic acid in Example 52 was replaced with trans-4-dimethylamino crotonate hydrochloride, and (R)-1e-IM3 was replaced with (R)-5e-IM3 to obtain a compound YZ001027, with a yield of 36%. 1H NMR (400 MHz, DMSO-$d_6$) δ 12.20 (s, 1H), 8.78 (s, 1H), 8.26 (s, 1H), 7.63-7.58 (m, 1H), 6.94 (d, J=2.6 Hz, 1H), 6.52 (s, 2H), 4.82 (d, J=6.1 Hz, 1H), 4.71 (d, J=17.8 Hz, 1H), 4.59 (dd, J=14.5, 6.7 Hz, 1H), 4.39 (d, J=16.8 Hz, 1H), 4.18-4.05 (m, 2H), 3.15 (d, J=5.5 Hz, 1H), 2.23 (s, 2H), 1.84 (s, 6H), 1.25 (s, 3H), ESI$(M+H)^+$=380.

Example 78 Synthesis of Compound YZ001030

Referring to the steps of Example 49, the intermediate (R)-1e-IM3 in Example 49 was replaced with the intermediate (R)-6e-IM3 to obtain a compound YZ001030, with a yield of 59%. 1H NMR (400 MHz, $CDCl_3$) δ 11.15 (s, 1H), 8.85 (s, 1H), 8.25 (s, 1H), 7.41 (s, 1H), 6.83 (s, 1H), 6.80-6.73 (m, 1H), 6.43 (d, J=16.2 Hz, 1H), 5.85 (d, J=10.5 Hz, 1H), 4.97 (dd, J=12.6, 4.7 Hz, 2H), 4.74-4.50 (m, 2H), 4.23 (dd, J=13.5, 4.2 Hz, 1H), 1.89-1.78 (m, 1H), 1.07 (s, 3H), 0.97 (s, 3H), ESI$(M+H)^+$=337.

Example 79 Synthesis of Compound YZ001031

Referring to the steps of Example 52, 2-fluoroacrylic acid in Example 52 was replaced with trans-4-dimethylamino crotonate hydrochloride, and (R)-1e-IM3 was replaced with (R)-6e-IM3 to obtain a compound YZ001031, with a yield of 78%. $^1$H NMR (400 MHz, CDCl3) δ 11.14 (s, 1H), 8.85 (s, 1H), 8.25 (s, 1H), 7.41 (s, 1H), 6.83 (s, 1H), 6.81-6.74 (m, 1H), 6.45 (d, J=16.2 Hz, 1H), 4.98 (dd, J=12.6, 4.7 Hz, 2H), 4.74-4.50 (m, 2H), 4.23 (dd, J=13.5, 4.2 Hz, 1H), 2.86 (d, J=4.0 Hz, 2H), 1.99 (s, 6H), 1.89-1.78 (m, 1H), 0.97 (s, 6H), ESI$(M+H)^+$=394.

Example 80 Synthesis of Compound YZ001032

Referring to the steps of Example 52, the intermediate (R)-1e-IM3 in Example 52 was replaced with the intermediate (R)-6e-IM3, and 2-fluoroacrylic acid was replaced with (2E)-4-(1-piperidinyl)-2-butenoic acid to obtain a compound YZ001032, with a yield of 87%. ESI(M+H)+=434.

Example 81 Synthesis of Compound YZ001033

Referring to the steps of Example 49, the intermediate (R)-1e-IM3 in Example 49 was replaced with the intermediate(S)-6e-IM3 to obtain a compound YZ001033, with a yield of 60%. 1H NMR (400 MHz, CDCl3) δ 11.13 (s, 1H), 8.84 (s, 1H), 8.25 (s, 1H), 7.40 (s, 1H), 6.83 (s, 1H), 6.80-6.73 (m, 1H), 6.43 (d, J=16.2 Hz, 1H), 5.85 (d, J=10.5 Hz, 1H), 4.97 (dd, J=12.6, 4.7 Hz, 2H), 4.74-4.50 (m, 2H), 4.23 (dd, J=13.5, 4.2 Hz, 1H), 1.89-1.78 (m, 1H), 1.05 (s, 3H), 0.93 (s, 3H), ESI$(M+H)^+$=337.

Example 82 Synthesis of Compound YZ001034

Referring to the steps of Example 52, 2-fluoroacrylic acid in Example 52 was replaced with trans-4-dimethylamino crotonate hydrochloride, and (R)-1e-IM3 was replaced with (S)-6e-IM3 to obtain a compound YZ001034, with a yield of 80%. 1H NMR (400 MHz, CDCl3) δ 11.13 (s, 1H), 8.85 (s, 1H), 8.23 (s, 1H), 7.41 (s, 1H), 6.83 (s, 1H), 6.82-6.74 (m, 1H), 6.45 (d, J=16.2 Hz, 1H), 4.98 (dd, J=12.6, 4.7 Hz, 2H), 4.74-4.50 (m, 2H), 4.23 (dd, J=13.5, 4.2 Hz, 1H), 2.86 (d, J=4.0 Hz, 2H), 1.99 (s, 6H), 1.89-1.78 (m, 1H), 0.97 (s, 6H), ESI$(M+H)^+$=394.

Example 83 Synthesis of Compound YZ001035

Referring to the steps of Example 52, the intermediate (R)-1e-IM3 in Example 52 was replaced with the intermediate(S)-6e-IM3, and 2-fluoroacrylic acid was replaced with (2E)-4-(1-piperidinyl)-2-butenoic acid to obtain a compound YZ001035, with a yield of 83%. ESI(M+H)+=434.

Example 84 Synthesis of Compound YZ001039

Referring to the steps of Example 49, the intermediate (R)-1e-IM3 in Example 49 was replaced with the intermediate 23T-IM1 to obtain a compound YZ001039, with a yield of 41%. 1H NMR (400 MHz, CDCl3) δ 10.19 (s, 1H), 8.35 (d, J=2.8 Hz, 1H), 8.09-7.92 (m, 1H), 7.45 (d, J=0.4 Hz, 1H), 7.06 (d, J=2.9 Hz, 1H), 6.96-6.81 (m, 1H), 6.73 (d, J=0.6 Hz, 1H), 6.49 (d, J=16.9 Hz, 1H), 5.86 (d, J=7.2 Hz, 1H), 4.53-3.98 (m, 2H), 3.07-2.61 (m, 2H), 1.26-1.06 (m, 2H), 1.02-0.48 (m, 2H). ESI(M+H)$^+$=320.

Example 85 Synthesis of Compound YZ001045

Referring to the steps of Example 49, the intermediate (R)-1e-IM3 in Example 49 was replaced with the intermediate (S,S)-7d-IM3 to obtain a compound YZ001045, with the yield of 48%. 1H NMR (400 MHz, DMSO-$d_6$) δ 11.75 (s, 1H), 8.27 (d, J=4.9 Hz, 1H), 8.06 (s, 1H), 7.74-7.67 (m, 1H), 7.61-7.57 (m, 1H), 7.53 (d, J=2.6 Hz, 1H), 7.05 (d, J=4.7 Hz, 1H), 6.65 (s, 1H), 6.18 (d, J=16.8 Hz, 1H), 5.44 (s, 1H), 5.08 (s, 1H), 4.66 (s, 2H), 2.27-2.16 (m, 2H), 2.02 (s, 1H), 1.96-1.89 (m, 1H), 1.71 (dd, J=13.6, 5.8 Hz, 2H), ESI(M+H)$^+$=334.

Example 86 Synthesis of Compound YZ001047

Referring to the steps of Example 52, 2-fluoroacrylic acid in Example 52 was replaced with trans-4-dimethylamino crotonate hydrochloride, and (R)-1e-IM3 was replaced with (S,S)-7d-IM3 to obtain a compound YZ001047, with a yield of 86%. 1H NMR (400 MHz, DMSO-$d_6$) δ 11.75 (s, 1H), 8.26 (d, J=4.9 Hz, 1H), 8.05 (s, 1H), 7.73-7.62 (m, 1H), 7.58 (d, J=7.5 Hz, 1H), 7.54-7.49 (m, 1H), 7.04 (d, J=4.9 Hz, 1H), 6.64 (d, J=1.6 Hz, 1H), 5.45 (d, J=17.2 Hz, 1H), 5.06 (s, 1H), 4.70 (s, 1H), 4.56 (d, J=18.0 Hz, 1H), 3.16 (s, 2H), 2.35 (s, 2H), 2.24 (s, 6H), 2.01 (s, 2H), 1.81-1.68 (m, 2H), ESI(M+H)$^+$=391.

Example 87 Synthesis of Compound YZ001048

Referring to the steps of Example 52, the intermediate (R)-1e-IM3 in Example 52 was replaced with the intermediate (R)-6e-IM3 to obtain the compound YZ0010048, with a yield of 70%. 1H NMR (400 MHz, CDCl3) δ 11.15 (s, 1H), 8.84 (s, 1H), 8.23 (s, 1H), 7.41 (s, 1H), 6.83 (s, 1H), 5.32 (t, J=4 Hz, 0.5H), 5.20 (d, J=4 Hz, 0.5H), 5.13 (d, J=16 Hz, 1H), 4.97 (dd, J=12.6, 4.7 Hz, 2H), 4.74-4.50 (m, 2H), 4.23 (dd, J=13.5, 4.2 Hz, 1H), 1.89-1.78 (m, 1H), 1.07 (s, 3H), 0.97 (s, 3H), ESI(M+H)$^+$=355.

Example 88 Synthesis of Compound YZ001049

Referring to the steps of Example 52, the intermediate (R)-1e-IM3 in Example 52 was replaced with the intermediate(S)-6e-IM3 to obtain a compound YZ0010049, with a yield of 68%. 1H NMR (400 MHz, $CDCl_3$) δ 11.13 (s, 1H), 8.81 (s, 1H), 8.25 (s, 1H), 7.40 (s, 1H), 6.83 (s, 1H), 5.30 (t, J=4 Hz, 0.5H), 5.24 (d, J=4 Hz, 0.5H), 5.16 (d, J=16 Hz, 1H), 4.97 (dd, J=12.6, 4.7 Hz, 2H), 4.71-4.45 (m, 2H), 4.23 (dd, J=13.5, 4.2 Hz, 1H), 1.84-1.73 (m, 1H), 1.05 (s, 3H), 0.93 (s, 3H), ESI(M+H)$^+$=355.

Example 89 Synthesis of Compound YZ001050

Referring to the steps of Example 52, the intermediate (R)-1e-IM3 in Example 52 was replaced with the intermediate(S)-6e-IM3, and 2-fluoroacrylic acid was replaced with 2-butynoic acid to obtain a compound YZ0010050, with a yield of 67%. 1H NMR (400 MHz, CDCl3) δ 11.12 (s, 1H), 8.84 (s, 1H), 8.25 (s, 1H), 7.40 (s, 1H), 6.83 (s, 1H), 4.97 (dd, J=12.6, 4.7 Hz, 2H), 4.74-4.50 (m, 2H), 4.23 (dd, J=13.5, 4.2 Hz, 1H), 2.03 (d, J=48 Hz, 3H), 1.89-1.78 (m, 1H), 1.05 (s, 3H), 0.93 (s, 3H), ESI(M+H)$^+$=349.

Example 90 Synthesis of Compound YZ001051

Referring to the steps of Example 52, the intermediate (R)-1e-IM3 in Example 52 was replaced with the intermediate (S,S)-7d-IM3 to obtain a compound YZ001051, with the yield of 86%. 1H NMR (400 MHz, DMSO-$d_6$) δ 11.77 (s, 1H), 8.26 (d, J=4.9 Hz, 1H), 8.07 (s, 1H), 7.75-7.67 (m, 1H), 7.57 (dd, J=9.6, 4.7 Hz, 1H), 7.52 (s, 1H), 7.02 (d, J=4.9 Hz, 1H), 6.64 (dd, J=3.2, 1.6 Hz, 1H), 5.39 (d, J=6.3 Hz, 2H), 5.25 (d, J=4.2 Hz, 1H), 4.73 (s, 1H), 2.30 (s, 1H), 2.04 (d, J=6.5 Hz, 2H), 1.76-1.57 (m, 2H), ESI(M+H)$^+$=352.

Example 91 Synthesis of Compound YZ001052

Referring to the steps of Example 49, the intermediate (R)-1e-IM3 in Example 49 was replaced with the intermediate 9f-IM5 to obtain a compound YZ001052, with a yield of 76%. 1H NMR (400 MHz, DMSO-$d_6$) δ 11.69 (s, 1H), 8.30 (d, J=4.9 Hz, 1H), 7.49 (s, 1H), 7.13-7.07 (m, 1H), 7.02 (d, J=4.8 Hz, 1H), 6.98-6.89 (m, 1H), 6.16 (d, J=15.2 Hz, 1H), 5.76 (d, J=12.0 Hz, 1H), 4.83 (d, J=13.9 Hz, 2H), 3.93 (d, J=5.6 Hz, 2H), 3.86 (s, 3H), 2.86 (s, 2H), ESI(M+H)$^+$=308.

Example 92 Synthesis of Compound YZ001053

Referring to the steps of Example 52, the intermediate 2-fluoroacrylic acid in Example 52 was replaced with the intermediate 2-butynoic acid, and (R)-1e-IM3 was replaced with(S)-3e-IM3 to obtain a compound YZ001053, with a yield of 76%. 1H NMR (400 MHz, DMSO-$d_6$) δ 12.16 (s, 1H), 8.76 (s, 1H), 8.51 (s, 1H), 7.60 (d, J=2.4 Hz, 1H), 7.05 (s, 1H), 5.15 (d, J=5.2 Hz, 1H), 4.68 (d, J=19.5 Hz, 1H), 4.32 (d, J=13.1 Hz, 1H), 2.92 (s, 1H), 2.76 (s, 1H), 2.13 (s, 3H), 1.27 (s, 3H), ESI(M+H)$^+$=321.

Example 93 Synthesis of Compound YZ001054

Referring to the steps of Example 52, the intermediate (R)-1e-IM3 in Example 52 was replaced with the intermediate 9f-IM5 to obtain a compound YZ001054, with a yield of 45%, 1H NMR (400 MHz, DMSO-$d_6$) δ 11.71 (s, 1H), 8.30 (d, J=4.9 Hz, 1H), 7.98 (s, 1H), 7.52-7.44 (m, 1H), 7.00 (s, 1H), 5.36 (s, 2H), 4.80 (s, 2H), 3.87 (s, 2H), 2.92 (s, 2H), 2.72 (s, 3H), ESI(M+H)$^+$=326.

Example 94 Synthesis of Compound YZ001055

Referring to the steps of Example 49, the intermediate (R)-1e-IM3 in Example 49 was replaced with the intermediate 12I-IM1 to obtain a compound YZ001055, with a yield of 32%. 1H NMR (400 MHz, DMSO-$d_6$) δ 11.77 (s, 1H), 8.26 (d, J=4.7 Hz, 1H), 8.10 (s, 1H), 7.54-7.49 (m, 1H), 7.07 (s, 2H), 6.65 (s, 1H), 6.22 (d, J=16.7 Hz, 1H), 5.31 (d, J=17.9 Hz, 1H), 4.71-4.38 (m, 2H), 3.71-3.58 (m, 1H), 3.20-3.09 (m, 1H), 1.65 (d, J=24.2 Hz, 2H), 1.52 (d, J=12.4 Hz, 2H), 1.32 (d, J=6.6 Hz, 4H). ESI(M+H)$^+$=348.

Example 95 Synthesis of Compound YZ001056

Referring to the steps of Example 52, the intermediate (R)-1e-IM3 in Example 52 was replaced with the intermediate 12I-IM1 to obtain compound YZ001054, with a yield of 65%, 1H NMR (400 MHz, DMSO-$d_6$) δ 11.77 (s, 1H), 8.26 (d, J=4.9 Hz, 1H), 8.12 (s, 1H), 7.56-7.49 (m, 1H), 7.07 (d, J=4.7 Hz, 1H), 6.65 (dd, J=3.3, 1.7 Hz, 1H), 5.42 (s, 1H), 5.34 (dd, J=30.3, 4.1 Hz, 1H), 4.69-4.32 (m, 2H), 3.01-2.86 (m, 1H), 2.71 (s, 1H), 1.86 (s, 2H), 1.62 (dd, J=79.8, 11.7 Hz, 6H), ESI$(M+H)^+$=366.

Example 96 Synthesis of Compound YZ001057

Referring to the steps of Example 49, the intermediate (R)-1e-IM3 in Example 49 was replaced with the intermediate 11h-IM1 to obtain a compound YZ001057, with a yield of 45%, 1H NMR (400 MHz, DMSO-$d_6$) δ 11.75 (s, 1H), 8.27 (d, J=4.9 Hz, 1H), 8.06 (s, 1H), 7.73-7.63 (m, 1H), 7.60-7.55 (m, 1H), 7.54-7.49 (m, 1H), 7.05 (d, J=4.8 Hz, 1H), 6.68-6.57 (m, 1H), 6.18 (d, J=16.6 Hz, 1H), 5.45 (d, J=16.6 Hz, 1H), 5.08 (s, 1H), 4.60 (dd, J=42.7, 24.3 Hz, 2H), 2.25 (dd, J=34.5, 28.5 Hz, 2H), 2.01 (s, 2H), 1.78-1.55 (m, 2H), ESI$(M+H)^+$=334.

Example 97 Synthesis of Compound YZ001058

Referring to the steps of Example 52, the intermediate (R)-1e-IM3 in Example 52 was replaced with the intermediate 11h-IM1 to obtain a compound YZ001058, with a yield of 55%, 1H NMR (400 MHz, DMSO-$d_6$) δ 11.77 (s, 1H), 8.27 (d, J=4.9 Hz, 1H), 8.07 (s, 1H), 7.63-7.40 (m, 1H), 7.03 (d, J=4.9 Hz, 1H), 6.65 (dd, J=3.2, 1.7 Hz, 1H), 5.39 (s, 1H), 5.26 (d, J=4.2 Hz, 1H), 3.65 (d, J=3.9 Hz, 1H), 3.17 (dd, J=7.4, 4.3 Hz, 1H), 2.72 (s, 2H), 2.39-2.18 (m, 2H), 2.05 (d, J=5.9 Hz, 2H), 1.76-1.54 (m, 2H). ESI$(M+H)^+$=352.

Example 98 Synthesis of Compound YZ001059

Referring to the steps of Example 49, the intermediate (R)-1e-IM3 in Example 49 was replaced with the intermediate 13J-IM1 to obtain a compound YZ001059, with a yield of 60%. 1H NMR (400 MHz, DMSO-$d_6$) δ 11.89-11.55 (m, 1H), 8.24 (t, J=10.8 Hz, 1H), 7.78 (d, J=9.6 Hz, 1H), 7.50 (s, 1H), 7.23 (d, J=4.4 Hz, 1H), 7.05-6.76 (m, 1H), 6.61 (s, 1H), 6.10 (d, J=16.0 Hz, 1H), 5.26 (dd, J=33.6, 16.6 Hz, 1H), 4.51 (dd, J=37.0, 13.5 Hz, 2H), 4.13 (d, J=11.3 Hz, 1H), 2.33 (s, 2H), 1.32 (d, J=5.9 Hz, 2H), 1.26 (s, 3H), ESI$(M+H)^+$=322.

Example 99 Synthesis of Compound YZ001060

Referring to the steps of Example 52, the intermediate (R)-1e-IM3 in Example 52 was replaced with the intermediate 13J-IM1 to obtain a compound YZ001058, with a yield of 53%. 1H NMR (400 MHz, DMSO-$d_6$) δ 11.73 (s, 1H), 8.24 (d, J=4.9 Hz, 1H), 7.78 (s, 1H), 7.54-7.42 (m, 1H), 7.17 (s, 1H), 6.62 (s, 1H), 5.31 (d, J=22.4 Hz, 1H), 5.05 (d, J=14.7 Hz, 1H), 4.61-4.47 (m, 2H), 3.64 (dd, J=6.6, 2.6 Hz, 1H), 2.71 (s, 2H), 2.33 (s, 2H), 1.38 (s, 3H). ESI$(M+H)^+$=340.

Example 100 Synthesis of Compound YZ001063

Referring to the steps of Example 49, the intermediate (R)-1e-IM3 in Example 49 was replaced with the intermediate 14K-IM3 to obtain a compound YZ001063, with a yield of 45%, 1H NMR (400 MHz, DMSO-$d_6$) δ 12.61 (s, 1H), 8.53 (s, 1H), 8.34 (d, J=4.9 Hz, 1H), 7.56 (s, 1H), 7.13 (d, J=4.9 Hz, 1H), 6.15 (d, J=16.7 Hz, 1H), 5.74 (s, 1H), 4.97 (d, J=6.2 Hz, 1H), 4.77 (d, J=17.1 Hz, 2H), 4.26-4.17 (m, 2H), 2.41 (d, J=2.4 Hz, 3H), 1.26 (s, 3H). ESI$(M+H)^+$=350.

Example 101 Synthesis of Compound YZ001064

Referring to the steps of Example 52, the intermediate (R)-1e-IM3 in Example 52 was replaced with the intermediate 14K-IM3 to obtain compound YZ001064, with a yield of 34%. 1H NMR (400 MHz, DMSO-$d_6$) δ 12.65 (s, 1H), 8.56 (d, J=2.5 Hz, 1H), 8.34 (d, J=4.9 Hz, 1H), 7.57 (s, 1H), 7.13 (d, J=4.9 Hz, 1H), 5.39-5.30 (m, 2H), 5.23 (d, J=4.1 Hz, 1H), 4.72 (d, J=17.1 Hz, 2H), 4.26 (t, J=14.9 Hz, 2H), 2.42 (s, 3H), 1.32 (d, J=6.7 Hz, 3H). ESI$(M+H)^+$=368.

Example 102 Synthesis of Compound YZ001065

Referring to the steps of Example 49, the intermediate (R)-1e-IM3 in Example 49 was replaced with the intermediate 8d-IM5 to obtain a compound YZ001065, with a yield of 55%, 1H NMR (400 MHz, DMSO-$d_6$) δ 13.03 (s, 1H), 11.68 (s, 1H), 8.31 (s, 1H), 7.50 (s, 1H), 7.18-7.07 (m, 1H), 6.96 (dd, J=16.7, 10.6 Hz, 1H), 6.16 (d, J=16.3 Hz, 1H), 5.87-5.70 (m, 1H), 4.85 (d, J=17.4 Hz, 1H), 3.92 (s, 2H), 2.86 (s, 2H), 2.80 (s, 2H). ESI$(M+H)^+$=294.

Example 103 Synthesis of Compound YZ001066

Referring to the steps of Example 52, the intermediate (R)-1e-IM3 in Example 52 was replaced with the intermediate 8d-IM5 to obtain compound YZ001066, with a yield of 43%. 1H NMR (400 MHz, DMSO-$d_6$) δ 11.77 (s, 1H), 8.32 (d, J=4.7 Hz, 1H), 7.53 (s, 1H), 7.09 (s, 1H), 6.95 (d, J=7.8 Hz, 1H), 5.36 (s, 1H), 4.79 (s, 1H), 3.88 (d, J=5.4 Hz, 2H), 3.44 (s, 2H), 2.90 (s, 2H). ESI$(M+H)^+$=312.

Example 104 Synthesis of Compound YZ001067

Referring to the steps of Example 52, the intermediate (R)-1e-IM3 in Example 52 was replaced with the intermediate 8d-IM5, and 2-fluoroacrylic acid was replaced with trans-4-dimethylamino crotonate hydrochloride to obtain a compound YZ001067, with a yield of 38%. 1H NMR (400 MHz, DMSO-$d_6$) δ 11.74 (s, 1H), 8.48 (d, J=3.1 Hz, 1H), 8.31 (d, J=1.2 Hz, 1H), 8.29 (d, J=1.2 Hz, 1H), 7.52 (s, 1H), 7.31 (dd, J=8.4, 4.3 Hz, 1H), 7.10 (d, J=4.8 Hz, 1H), 4.80 (s, 2H), 3.91 (s, 2H), 3.28 (dd, J=11.2, 5.7 Hz, 2H), 3.06 (s, 2H), 2.34 (s, 6H). ESI$(M+H)^+$=351.

Example 105 Synthesis of Compound YZ001068

Referring to the steps of Example 52, the intermediate (R)-1e-IM3 in Example 52 was replaced with the intermediate 11h-IM1, and 2-fluoroacrylic acid was replaced with trans-4-dimethylamino crotonate hydrochloride to obtain a compound YZ001068, with a yield of 48%. 1H NMR (400 MHz, DMSO-$d_6$) δ 11.76 (s, 1H), 8.26 (d, J=4.9 Hz, 1H), 8.06 (s, 1H), 7.77-7.59 (m, 1H), 7.53-7.49 (m, 1H), 7.04 (d, J=4.9 Hz, 1H), 6.81 (d, J=14.6 Hz, 1H), 6.67-6.61 (m, 1H), 5.46 (d, J=17.6 Hz, 1H), 5.07 (s, 1H), 4.76-4.48 (m, 2H), 3.07 (dd, J=8.8, 4.2 Hz, 2H), 2.35 (d, J=1.8 Hz, 2H), 2.19 (s, 6H), 2.04-1.91 (m, 2H), 1.71 (m, 2H). ESI$(M+H)^+$=391.

Example 106 Synthesis of Compound YZ001069

Referring to the steps of Example 52, the intermediate (R)-1e-IM3 in Example 52 was replaced with the intermediate 13J-IM1, and 2-fluoroacrylic acid was replaced with trans-4-dimethylamino crotonate hydrochloride to obtain a compound YZ001069, with a yield of 38%. 1H NMR (400 MHz, DMSO-$d_6$) δ 11.76 (d, J=26.3 Hz, 1H), 8.27 (dd, J=13.4, 4.9 Hz, 1H), 7.78 (d, J=9.5 Hz, 1H), 7.56-7.47 (m, 1H), 7.23 (d, J=4.9 Hz, 1H), 6.98 (d, J=4.9 Hz, 1H), 6.62 (d, J=10.9 Hz, 2H), 5.53-5.21 (m, 1H), 4.83 (s, 1H), 4.65 (d, J=17.4 Hz, 2H), 4.12 (d, J=12.7 Hz, 1H), 3.11 (d, J=5.3 Hz, 2H), 2.33 (d, J=5.9 Hz, 2H), 2.21 (d, J=5.9 Hz, 6H), 1.69 (s, 3H). ESI(M+H)$^+$=379.

Example 107 Synthesis of Compound YZ001070

Referring to the steps of Example 52, the intermediate (R)-1e-IM3 in Example 52 was replaced with the intermediate 9f-IM5, and 2-fluoroacrylic acid was replaced with trans-4-dimethylamino crotonate hydrochloride to obtain a compound YZ001070, with a yield of 48%. 1H NMR (400 MHz, DMSO-$d_6$) δ 11.69 (s, 1H), 8.30 (d, J=4.7 Hz, 1H), 7.66-7.42 (m, 1H), 7.08 (d, J=4.9 Hz, 1H), 7.01 (dd, J=3.3, 2.0 Hz, 1H), 6.83 (d, J=15.1 Hz, 1H), 6.71-6.58 (m, 1H), 4.81 (s, 2H), 3.93 (s, 2H), 3.86 (s, 3H), 3.26 (d, J=6.3 Hz, 2H), 2.87 (s, 2H), 2.32 (s, 6H). ESI(M+H)$^+$=365.

Example 108 Synthesis of Compound YZ001071

Referring to the steps of Example 52, (R)-1e-IM3 in Example 52 was replaced with 23T-IM1 to obtain a compound YZ001071, with a yield of 57%. 1H NMR (400 MHz, CDCl3) δ 10.39 (s, 1H), 8.29 (d, J=2.8 Hz, 1H), 8.08-7.94 (m, 1H), 7.46 (d, J=0.4 Hz, 1H), 7.09 (d, J=2.6 Hz, 1H), 6.96-6.81 (m, 1H), 6.78 (d, J=0.6 Hz, 1H), 6.52 (t, J=4 Hz, 0.5H), 5.78 (d, J=16 Hz, 1H), 4.56-3.99 (m, 2H), 3.08-2.63 (m, 2H), 1.27-1.05 (m, 2H), 1.01-0.49 (m, 2H), ESI(M+H)$^+$ =338.

Example 109 Synthesis of Compound YZ001072

Referring to the steps of Example 49, the intermediate (R)-1e-IM3 in Example 49 was replaced with the intermediate 24U-IM1 to obtain a compound YZ001072, with a yield of 32%. 1H NMR (400 MHz, $CDCl_3$) δ 8.47 (d, J=3.8 Hz, 1H), 7.88 (d, J=7.6 Hz, 1H), 7.77 (d, J=4.0 Hz, 1H), 7.32 (s, 1H), 6.71 (d, J=0.6 Hz, 1H), 6.63 (d, J=4.0 Hz, 1H), 6.45 (d, J=16.8 Hz, 1H), 5.84 (d, J=7.2 Hz, 1H), 1.70 (s, 3H), 1.51-1.43 (m, 1H), 1.37 (d, J=6.4 Hz, 2H), 1.33 (s, 2H), 1.26-1.23 (m, 1H), 0.92 (t, J=6.6 Hz, 2H), 0.90-0.85 (m, 1H), ESI(M+H)$^+$=368.

Example 110 Synthesis of Compound YZ001073

Referring to the steps of Example 52, the intermediate (R)-1e-IM3 in Example 52 was replaced with the intermediate 24U-IM1 to obtain compound YZ001073, with a yield of 56%. 1H NMR (400 MHz, $CDCl_3$) δ 8.26 (s, 1H), 7.91 (d, J=8.0 Hz, 1H), 7.54 (d, J=3.9 Hz, 1H), 7.37 (s, 1H), 6.71 (d, J=0.6 Hz, 1H), 6.49 (t, J=3.8 Hz, 0.5H), 5.89 (d, J=4 Hz, 0.5H), 5.78 (d, J=16 Hz, 1H), 1.70 (s, 3H), 1.51-1.43 (m, 1H), 1.37 (d, J=6.6 Hz, 2H), 1.33 (s, 2H), 1.26-1.23 (m, 1H), 0.92 (t, J=6.8 Hz, 2H), 0.90-0.85 (m, 1H), ESI(M+H)$^+$=386.

Example 111 Synthesis of Compound YZ001074

Referring to the steps of Example 49, the intermediate (R)-1e-IM3 in Example 49 was replaced with the intermediate 25V-IM4 to obtain a compound YZ001074, with a yield of 39%. 1H NMR (400 MHz, $CDCl_3$) δ 8.50 (d, J=3.8 Hz, 1H), 7.85 (d, J=7.6 Hz, 1H), 7.79 (d, J=4.0 Hz, 1H), 7.31 (s, 1H), 6.69 (d, J=0.6 Hz, 1H), 6.60 (d, J=4.0 Hz, 1H), 6.47 (d, J=16.4 Hz, 1H), 5.83 (d, J=7.0 Hz, 1H), 2.53 (s, 3H), 2.31 (d, J=6.4 Hz, 2H), 1.51-1.43 (m, 1H), 1.31 (s, 2H), 1.21-1.19 (m, 1H), 1.15 (t, J=6.6 Hz, 2H), 0.92-0.86 (m, 1H), ESI(M+H)$^+$=400.

Example 112 Synthesis of Compound YZ001075

Referring to the steps of Example 52, the intermediate (R)-1e-IM3 in Example 52 was replaced with the intermediate 25V-IM4 to obtain a compound YZ001075, with a yield of 61%. 1H NMR (400 MHz, $CDCl_3$) δ 8.26 (d, J=4.0 Hz, 1H), 7.78 (d, J=8.0 Hz, 1H), 7.68 (d, J=3.8 Hz, 1H), 7.28 (s, 1H), 6.57 (s, 1H), 6.36 (t, J=3.8 Hz, 0.5H), 5.85 (d, J=4 Hz, 0.5H), 5.76 (d, J=14 Hz, 1H), 2.56 (s, 3H), 2.34 (d, J=6.4 Hz, 2H), 1.53-1.44 (m, 1H), 1.32 (s, 2H), 1.23-1.19 (m, 1H), 1.15 (t, J=6.6 Hz, 2H), 0.90-0.84 (m, 1H), ESI(M+H)$^+$=418.

Example 113 Synthesis of Compound YZ001076

Referring to the steps of Example 49, the intermediate (R)-1e-IM3 in Example 49 was replaced with the intermediate 15L-IM4 to obtain a compound YZ001076, with a yield of 45%, 1H NMR (400 MHz, DMSO-$d_6$) δ 13.31 (d, J=43.4 Hz, 1H), 11.85 (d, J=85.5 Hz, 1H), 8.31 (s, 1H), 7.65 (s, 1H), 7.25 (s, 1H), 6.81 (d, J=21.5 Hz, 2H), 6.39-6.23 (m, 1H), 5.81 (dd, J=10.3, 2.3 Hz, 1H), 5.05 (s, 1H), 4.87 (s, 1H), 4.78 (s, 1H), 4.61 (s, 1H), ESI(M+H)$^+$=280.

Example 114 Synthesis of Compound YZ001077

Referring to the steps of Example 52, the intermediate (R)-1e-IM3 in Example 52 was replaced with the intermediate 15L-IM4 to obtain compound YZ001077, with a yield of 52%. 1H NMR (400 MHz, DMSO-$d_6$) δ 13.43 (s, 1H), 12.00 (s, 1H), 9.10-8.63 (m, 1H), 8.31 (s, 1H), 7.64 (s, 1H), 7.28 (s, 1H), 5.43 (dd, J=17.4, 3.6 Hz, 1H), 5.09 (s, 1H), 2.92 (s, 2H), 2.75 (s, 2H), ESI(M+H)$^+$=298.

Example 115 Synthesis of Compound YZ001083

Referring to the steps of Example 49, the intermediate (R)-1e-IM3 in Example 49 was replaced with the intermediate 180-IM4 to obtain compound YZ001083, with a yield of 44%. 1H NMR (400 MHz, DMSO-$d_6$) δ 11.71 (s, 1H), 8.30 (s, 1H), 7.53-7.37 (m, 1H), 7.15 (s, 1H), 7.05 (s, 1H), 6.94 (d, J=10.7 Hz, 1H), 6.13 (dd, J=16.7, 2.1 Hz, 1H), 5.72 (s, 1H), 5.39 (d, J=16.4 Hz, 1H), 4.85 (s, 1H), 4.22 (d, J=16.3 Hz, 1H), 3.87 (s, 3H), 2.96 (dd, J=37.6, 16.3 Hz, 1H), 2.79 (d, J=15.1 Hz, 1H), 1.26 (d, J=2.5 Hz, 3H), ESI(M+H)$^+$ =322.

Example 116 Synthesis of Compound YZ001084

Referring to the steps of Example 52, the intermediate (R)-1e-IM3 in Example 52 was replaced with the intermediate 180-IM4 to obtain a compound YZ001084, with a yield of 46%. 1H NMR (400 MHz, DMSO-$d_6$) δ 11.73 (s, 1H), 8.30 (d, J=4.9 Hz, 1H), 7.59-7.40 (m, 1H), 7.11 (s, 1H), 7.02 (s, 1H), 5.39-5.10 (m, 2H), 3.87 (s, 3H), 3.01 (t, J=23.0 Hz, 1H), 2.92 (s, 1H), 2.82 (d, J=16.0 Hz, 1H), 2.72 (s, 2H), 1.30 (d, J=6.6 Hz, 3H), ESI(M+H)$^+$=340.

Example 117 Synthesis of Compound YZ001085

Referring to the steps of Example 49, the intermediate (R)-1e-IM3 in Example 49 was replaced with the intermediate 19P-IM1 to obtain a compound YZ001083, with a yield of 44%. 1H NMR (400 MHz, DMSO-$d_6$) δ 11.69 (s, 1H), 8.31 (s, 1H), 7.50 (d, J=2.5 Hz, 1H), 7.13 (s, 1H), 7.07 (s, 1H), 6.96 (dd, J=16.7, 10.6 Hz, 1H), 6.13 (dd, J=16.7, 2.1 Hz, 1H), 5.73 (d, J=10.5 Hz, 1H), 5.38 (d, J=16.4 Hz, 1H), 4.83 (s, 1H), 4.58-4.51 (m, 1H), 3.01 (s, 1H), 2.81 (d, J=14.8 Hz, 1H), 1.49 (t, J=6.9 Hz, 6H), 1.25 (s, 3H), $ESI(M+H)^+$ =350.

Example 118 Synthesis of Compound YZ001086

Referring to the steps of Example 52, the intermediate (R)-1e-IM3 in Example 52 was replaced with the intermediate 19P-IM1 to obtain a compound YZ001086, with a yield of 56%. 1H NMR (400 MHz, DMSO-$d_6$) δ 11.89 (s, 1H), 8.37 (s, 1H), 7.57 (d, J=2.3 Hz, 1H), 7.19 (s, 1H), 7.11 (s, 1H), 5.41-5.30 (m, 2H), 5.22 (d, J=4.1 Hz, 1H), 4.61-4.51 (m, 1H), 4.41 (s, 1H), 3.06 (s, 1H), 2.87 (d, J=16.1 Hz, 1H), 1.51 (d, J=6.5 Hz, 6H), 1.31 (d, J=6.7 Hz, 3H), $ESI(M+H)^+$ =368.

Example 119 Synthesis of Compound YZ001087

Referring to the steps of Example 49, the intermediate (R)-1e-IM3 in Example 49 was replaced with the intermediate 10g-IM3 to obtain a compound YZ001087, with a yield of 32%. $^1$H NMR (400 MHz, DMSO-$d_6$) δ 12.03 (s, 1H), 8.39 (d, J=4.1 Hz, 1H), 7.65 (s, 1H), 7.10 (d, J=15.5 Hz, 1H), 6.94 (dd, J=16.6, 10.5 Hz, 1H), 6.34 (d, J=16.3 Hz, 1H), 6.13 (dd, J=16.7, 1.9 Hz, 1H), 5.76-5.69 (m, 1H), 4.88 (s, 1H), 4.44 (d, J=32.8 Hz, 2H), 3.91 (d, J=6.5 Hz, 4H), 3.78 (d, J=5.2 Hz, 2H), 2.83 (s, 2H), 2.27-2.12 (m, 2H), $ESI(M+H)^+$=364.

Example 120 Synthesis of Compound YZ001088

Referring to the steps of Example 52, the intermediate (R)-1e-IM3 in Example 52 was replaced with the intermediate 10g-IM3 to obtain a compound YZ001088, with a yield of 45%, 1H NMR (400 MHz, DMSO-$d_6$) δ 12.05 (s, 1H), 8.39 (d, J=3.9 Hz, 1H), 7.65 (s, 1H), 7.11 (dd, J=19.4, 4.7 Hz, 1H), 6.32 (d, J=16.9 Hz, 1H), 5.32 (s, 2H), 4.87 (s, 1H), 4.42 (d, J=19.5 Hz, 2H), 3.90 (s, 4H), 3.78 (d, J=5.2 Hz, 2H), 2.88 (s, 2H), 2.22 (d, J=4.7 Hz, 2H), $ESI(M+H)^+$=382.

Example 121 Synthesis of Compound YZ001091

Referring to the steps of Example 49, the intermediate (R)-1e-IM3 in Example 49 was replaced with the intermediate 16M-IM1 to obtain a compound YZ001091, with a yield of 65%, 1H NMR (400 MHz, DMSO-$d_6$) δ 13.26 (s, 1H), 11.80 (s, 1H), 9.11 (s, 1H), 8.46-8.06 (m, 1H), 7.56 (s, 1H), 7.17 (s, 1H), 6.79 (td, J=15.9, 10.3 Hz, 1H), 6.36-6.21 (m, 1H), 5.78 (s, 1H), 5.00 (s, 1H), 3.63 (s, 2H), 1.59-1.48 (m, 3H). $ESI(M+H)^+$=294.

Example 122 Synthesis of Compound YZ001093

Referring to the steps of Example 49, the intermediate (R)-1e-IM3 in Example 49 was replaced with the intermediate 20Q-IM1 to obtain a compound YZ001093, with a yield of 44%. 1H NMR (400 MHz, DMSO-$d_6$) δ 11.71 (s, 1H), 8.26 (d, J=4.9 Hz, 1H), 7.70 (d, J=6.9 Hz, 1H), 7.57-7.47 (m, 2H), 6.99-6.79 (m, 1H), 6.53-6.45 (m, 1H), 6.10 (dd, J=16.6, 2.2 Hz, 1H), 5.76-5.67 (m, 1H), 4.92 (s, 2H), 4.56 (s, 2H), 3.96 (d, J=4.8 Hz, 2H), 1.99 (s, 2H). $ESI(M+H)^+$=308.

Example 123 Synthesis of Compound YZ001094

Referring to the steps of Example 52, the intermediate (R)-1e-IM3 in Example 52 was replaced with the intermediate 20Q-IM1 to obtain a compound YZ001094, with a yield of 35%, 1H NMR (400 MHz, DMSO-$d_6$) δ 11.73 (s, 1H), 8.25 (d, J=4.9 Hz, 1H), 7.73 (s, 1H), 7.60-7.43 (m, 1H), 7.38 (s, 1H), 6.50 (s, 1H), 5.36-5.21 (m, 1H), 4.95 (s, 2H), 4.64-4.46 (m, 2H), 3.90 (s, 2H), 2.06 (s, 2H). $ESI(M+H)^+$ =326.

Example 124 Synthesis of Compound YZ001095

Referring to the steps of Example 49, the intermediate (R)-1e-IM3 in Example 49 was replaced with the intermediate 21R-IM1 to obtain a compound YZ001095, with a yield of 64%. 1H NMR (400 MHz, DMSO-$d_6$) δ 11.75 (s, 1H), 8.89 (s, 1H), 8.22 (t, J=5.1 Hz, 1H), 7.87 (d, J=11.0 Hz, 1H), 7.51 (dd, J=5.5, 2.7 Hz, 1H), 6.96 (t, J=5.6 Hz, 1H), 6.54-6.47 (m, 1H), 6.18 (dd, J=16.7, 2.3 Hz, 1H), 5.74 (dd, J=10.4, 2.3 Hz, 1H), 4.86 (s, 2H), 3.68-3.56 (m, 4H), 3.15 (dd, J=7.4, 4.2 Hz, 4H).

$ESI(M+H)^+$=322.

Example 125 Synthesis of Compound YZ001096

Referring to the steps of Example 52, the intermediate (R)-1e-IM3 in Example 52 was replaced with the intermediate 21R-IM1 to obtain a compound YZ001096, with a yield of 55%, 1H NMR (400 MHz, DMSO-$d_6$) δ 11.74 (s, 1H), 8.20 (d, J=4.9 Hz, 1H), 7.88 (d, J=8.8 Hz, 1H), 7.53-7.40 (m, 1H), 6.87 (d, J=4.9 Hz, 1H), 6.55-6.34 (m, 1H), 5.29 (s, 1H), 4.96 (s, 1H), 4.89 (s, 2H), 4.46 (s, 2H), 3.42 (d, J=4.8 Hz, 2H), 1.86 (d, J=3.5 Hz, 2H), 1.76 (s, 2H). $ESI(M+H)^+$=340.

Example 126 Synthesis of Compound YZ001099

Referring to the steps of Example 49, the intermediate (R)-1e-IM3 in Example 49 was replaced with the intermediate 22S-IM1 to obtain a compound YZ001099, with a yield of 54%. 1H NMR (400 MHz, DMSO-$d_6$) δ 11.77 (s, 1H), 8.27 (d, J=4.8 Hz, 1H), 8.04 (s, 1H), 7.63-7.43 (m, 1H), 7.00 (dd, J=11.2, 5.2 Hz, 2H), 6.65 (dd, J=3.3, 1.6 Hz, 1H), 6.23 (d, J=16.9 Hz, 1H), 5.82 (d, J=10.6 Hz, 1H), 5.01 (d, J=4.6 Hz, 2H), 4.49 (d, J=4.4 Hz, 2H), 3.94 (dd, J=14.1, 6.5 Hz, 1H), 1.51 (d, J=6.3 Hz, 3H). $ESI(M+H)^+$=308.

Example 127 Synthesis of Compound YZ001100

Referring to the steps of Example 52, the intermediate (R)-1e-IM3 in Example 52 was replaced with the intermediate 22S-IM1 to obtain a compound YZ001100, with a yield of 35%, 1H NMR (400 MHz, DMSO-$d_6$) δ 11.78 (s, 1H), 8.27 (d, J=4.9 Hz, 1H), 8.02 (d, J=31.4 Hz, 1H), 7.69-7.45 (m, 1H), 6.97 (d, J=4.8 Hz, 1H), 6.69-6.49 (m, 1H), 5.02 (s, 2H), 4.62-4.43 (m, 1H), 4.36-4.15 (m, 1H), 3.88 (dd, J=13.9, 6.6 Hz, 1H), 2.91 (s, 1H), 2.76 (s, 1H), 1.53 (d, J=6.5 Hz, 3H). $ESI(M+H)^+$=326.

Example 128 Synthesis of Compound YZ001103

Referring to the steps of Example 49, the intermediate (R)-1e-IM3 in Example 49 was replaced with the intermediate 26W-IM1 to obtain a compound YZ001103, with a yield of 80%. 1H NMR (400 MHz, DMSO-d6) δ 11.67 (s, 1H), 8.27 (d, J=5.1 Hz, 1H), 7.46 (d, J=2.9 Hz, 1H), 7.05 (d, J=5.0 Hz, 1H), 7.00-6.96 (m, 1H), 6.14 (dd, J=16.5, 2.3 Hz, 1H), 5.76 (s, 1H), 5.75-5.64 (m, 1H), 4.79 (s, 2H), 3.90 (d, J=6.1 Hz, 2H), 2.83 (s, 2H). $ESI(M+H)^+$=311.

Example 129 Synthesis of Compound YZ001104

Referring to the steps of Example 52, the intermediate (R)-1e-IM3 in Example 52 was replaced with the intermediate 26W-IM1 to obtain a compound YZ001104, with a yield of 53%. $^{1}$H NMR (400 MHz, DMSO-d6) δ 11.69 (s, 1H), 8.27 (d, J=5.0 Hz, 1H), 7.48 (dd, J=3.4, 2.5 Hz, 1H), 7.06-6.95 (m, 2H), 5.26 (dd, J=49.9, 4.1 Hz, 2H), 4.76 (s, 2H), 3.87 (t, J=6.0 Hz, 2H), 2.89 (s, 2H). ESI(M+H)$^+$=329.

Example 130 Synthesis of Compound YZ001107

Referring to the steps of Example 52, the intermediate (R)-1e-IM3 in Example 52 was replaced with the intermediate(S)-1e-IM3 to obtain a compound YZ001107, with a yield of 45%, 1H NMR (400 MHz, DMSO-d6) δ 11.75 (s, 1H), 8.23 (s, 1H), 8.05 (s, 1H), 7.51 (dd, J=3.5, 2.5 Hz, 1H), 7.03 (s, 1H), 6.62 (s, 1H), 5.39 (s, 1H), 5.31 (dd, J=32.1, 4.1 Hz, 1H), 5.22 (d, J=17.4 Hz, 1H), 4.84 (d, J=35.8 Hz, 2H), 4.39-4.23 (m, 2H), 1.28 (d, J=6.9 Hz, 3H). ESI(M+H)$^+$=326

Example 131 Synthesis of Compound YZ001108

Referring to the steps of Example 49, the intermediate (R)-1e-IM3 in Example 49 was replaced with the intermediate 27X-IM1 to obtain a compound YZ001108, with a yield of 45%, $^{1}$H NMR (400 MHz, DMSO-d6) δ 11.84 (s, 1H), 8.34 (s, 1H), 7.55 (s, 1H), 7.19 (s, 1H), 6.98 (s, 1H), 6.94-6.86 (m, 1H), 6.13-6.06 (m, 1H), 5.74-5.65 (m, 1H), 4.79 (s, 2H), 3.84 (s, 2H), 3.12 (s, 2H), 2.71 (s, 3H). ESI(M+H)$^+$=336

Example 132 Synthesis of Compound YZ001109

Referring to the steps of Example 52, the intermediate (R)-1e-IM3 in Example 52 was replaced with the intermediate 27X-IM1 to obtain a compound YZ001109, with a yield of 53%. 1H NMR (400 MHz, DMSO-d6) δ 11.89 (s, 1H), 8.37 (d, J=4.9 Hz, 1H), 7.60 (t, J=3.0 Hz, 1H), 7.24-7.14 (m, 1H), 7.00 (dd, J=3.4, 1.9 Hz, 1H), 5.42-5.20 (m, 2H), 4.81 (s, 2H), 3.86 (s, 2H), 3.19 (s, 2H), 2.69 (s, 3H). ESI(M+H)$^+$=354

Example 133 Synthesis of Compound YZ001115

Referring to the steps of Example 49, the intermediate (R)-1e-IM3 in Example 49 was replaced with the intermediate 28Y-IM3 to obtain a compound YZ001115, with a yield of 58%. 1H NMR (400 MHz, DMSO-$d_6$) δ 11.99 (s, 1H), 8.34 (dd, J=4.8, 1.1 Hz, 1H), 7.61 (d, J=1.2 Hz, 1H), 7.13 (dd, J=4.8, 1.0 Hz, 1H), 6.65 (ddd, J=36.7, 16.7, 10.3 Hz, 1H), 6.36 (ddd, J=14.6, 3.4, 1.8 Hz, 1H), 6.21 (ddd, J=16.7, 8.8, 2.4 Hz, 1H), 5.84-5.57 (m, 1H), 4.76 (d, J=52.0 Hz, 2H), 4.51 (d, J=48.8 Hz, 3H), 1.37 (d, J=6.5 Hz, 6H). ESI(M+H)$^+$=322.

Example 134 Synthesis of Compound YZ001117

Referring to the steps of Example 49, the intermediate (R)-1e-IM3 in Example 49 was replaced with the intermediate 29Z-IM3 to obtain a compound YZ001117, with a yield of 60%. 1H NMR (400 MHz, DMSO-$d_6$) δ 11.96 (s, 1H), 8.31 (d, J=4.8 Hz, 1H), 7.57 (s, 1H), 7.01 (d, J=4.8 Hz, 1H), 6.86 (dd, J=16.6, 10.5 Hz, 1H), 6.41-6.18 (m, 1H), 6.06 (dd, J=16.7, 2.4 Hz, 1H), 5.66 (dd, J=10.5, 2.4 Hz, 1H), 4.66-4.18 (m, 3H), 3.84 (d, J=6.8 Hz, 2H), 2.76 (s, 2H), 1.28 (d, J=6.6 Hz, 5H). ESI(M+H)$^+$=336.

Example 135 Synthesis of Compound YZ001118

Referring to the steps of Example 49, the intermediate (R)-1e-IM3 in Example 49 was replaced by the intermediate 30A-IM3 to obtain a compound YZ001118, with a yield of 41%. 1H NMR (400 MHz, DMSO-$d_6$) δ 11.95 (s, 1H), 8.31 (d, J=4.9 Hz, 1H), 7.58 (s, 1H), 7.07 (d, J=4.9 Hz, 1H), 6.87 (dd, J=16.7, 10.5 Hz, 1H), 6.31 (dd, J=3.5, 1.8 Hz, 1H), 6.07 (dd, J=16.7, 2.3 Hz, 1H), 5.66 (dd, J=10.5, 2.3 Hz, 1H), 4.43 (d, J=17.3 Hz, 2H), 3.85 (s, 2H), 3.68 (s, 3H), 2.73 (s, 2H). ESI(M+H)$^+$=336.

Example 136 JAK3 Kinase Inhibitory Activity of the Compound Disclosed in the Present Invention (the Experiment was Entrusted to be Conducted by BioDuro-Sundia (Shanghai) Co., Ltd.)

Objective of Experiment

A Mobility shift assay was adopted to detect compounds to be tested (see list below) for in vitro inhibitory activity on the enzyme activity of JAK3 kinase. Cerdulatinib (Supplier: selleckchem; Cat. No.: S7634) was used as a positive control compound.

Experimental Method

Formulation of Compound

The compound was dissolved in 100% DMSO to formulate a 10 mM stock solution, which was stored in a −20° C. refrigerator with protection from light.

2. Kinase Reaction Process (1) a 1× Kinase buffer was formulated.

(2) formulation of compound concentration gradient: the compounds to be tested (including the example compound and PF-06651600) have a test concentration of 10,000 nM, and were diluted by 10 times to obtain 10 concentrations, and were detected in single wells. The compounds were diluted with gradients into solutions with a final concentration of 100 times in a 384-well plate. Then 250 nL was transferred to a 384 reaction plate with Echo550 for later use. 250 nL of 100% DMSO was added into the negative control well and the positive control well respectively.

(3) A kinase solution with a final concentration of 2.5 times was formulated with the 1× Kinase buffer.

(4) The compound wells and the positive control wells were added with 10 μL of the kinase solution with the final concentration of 2.5 times respectively; the negative control wells were added with 10 μL of the 1× Kinase buffer.

(5) The wells were centrifuged at 1,000 rpm for 30 seconds, mixed well by shaking, and then incubated at room temperature for 10 minutes.

(6) A mixed solution of ATP and Kinase substrate 22 with a final concentration of 25/15 times was formulated with a 1× Kinase buffer.

(7) The compound wells, positive control wells and negative control wells of the 384 reaction plate were respectively added with 15 μL of a mixed solution of ATP and the substrate at the final concentration of 25/15 times to start the reaction.

(8) The 384-well plate was centrifuged at 1,000 rpm for 30 seconds, mixed well by shaking, and then incubated at room temperature for 30 minutes.

(9) 30 μL of a detection termination solution was added to stop the kinase reaction, centrifuged at 1,000 rpm for 30 seconds, and mixed well by shaking.

(10) The conversion rate was read with Caliper EZ Reader.

3. Data Analysis (1) Calculation Equation

% Inhibition=(Conversion %_max−Conversion %_sample)/(Conversion %_max−Conversion %_min)×100

Among them: Conversion %_sample was the conversion rate reading of the sample; Conversion %_min was the mean value of the negative control wells, representing the conversion rate reading of the wells without enzyme activity; Conversion % max was the mean value of the positive control wells, representing the conversion rate reading of the wells without compound inhibition; and % Inhibition represented the percentage inhibition rate.

(2) Fitting of Dose-Response Curve by taking the log value of concentration as the X axis and taking the percent inhibition rate as the Y axis, a dose-response curve is fitted by adopting the log (inhibitor) vs. response-Variable slope of the analysis software GraphPad Prism 5, so as to obtain the IC50 value of each compound on the enzyme activity. The calculation equation was Y=Bottom+(Top−Bottom)/(1+10^((Log IC50−X)*HillSlope)).

Experimental Results

| Compound number | JAK3 IC50 (nM) | Compound number | JAK3 IC50 (nM) | Compound number | JAK3 IC50 (nM) |
|---|---|---|---|---|---|
| YZ001001 | 0.72 | YZ001028 | 0.19 | YZ001076 | 0.28 |
| YZ001002 | 0.14 | YZ001030 | 2.4 | YZ001077 | 7.1 |
| YZ001003 (Comparative Example) | >10000 | YZ001033 | 0.12 | YZ001078 | 0.22 |
| YZ001004 | 3.6 | YZ001039 | 1.5 | YZ001083 | 1.5 |
| YZ001011 (Comparative Example) | >10000 | YZ001045 | 0.19 | YZ001085 | 0.53 |
| YZ001012 (Comparative Example) | 491 | YZ001047 | 4.5 | YZ001091 | 5.1 |
| YZ001013 | 8.1 | YZ001052 | 0.25 | YZ001093 | 1.4 |
| YZ001017 | 1.6 | YZ001053 | 2.5 | YZ001095 | 7 |
| YZ001018 | 0.48 | YZ001054 | 4.4 | YZ001099 | 0.2 |
| YZ001020 | 0.93 | YZ001055 | 0.11 | YZ001100 | 3.8 |
| YZ001021 | 0.079 | YZ001056 | 4.2 | YZ001103 | 0.29 |
| YZ001022 | 0.87 | YZ001057 | 0.31 | YZ001104 | 4.3 |
| YZ001023 | 0.58 | YZ001063 | 1.4 | YZ001107 | 1.5 |
| YZ001024 | 0.15 | YZ001065 | 0.7 | YZ001108 | 0.35 |
| YZ001025 | 1.2 | YZ001066 | 5.8 | YZ001109 | 5.2 |
| YZ001026 | 0.43 | YZ001074 | 0.57 | YZ001117 | 6.93 |
| YZ001027 | 7.8 | YZ001075 | 1.2 | PF-06651600 | 18 |
| Cerdulatinib | 0.65 | / | / | / | / |

Compared with the positive control PF-06651600, the compound applied for by the present invention had a different parent nucleus structure, and the structural distinguishing characteristics were very significant. The data in the above table showed that most of the compounds applied for by the present invention had better in vitro JAK3 kinase inhibitory activity compared with PF-06651600. The inhibitory activity of partial compounds against JAK3 kinase was more than 10 times that of PF-06651600, and thus they had obvious technical effect on kinase inhibitory activity. By comparing the examples YZ001003 and YZ001001, it had been found that the two had the same molecular skeleton, except that a covalent target head was connected on the NH group of YZ001001, while a non-covalent target head was connected on the NH group of YZ001003. The former had good JAK3 Kinase inhibitory activity, while the latter had basically no inhibitory activity. By comparing the examples YZ001011, YZ001012 and YZ001017, it had been found that the two had the same molecular skeleton, except that a covalent target head was connected on the NH group of YZ001017, while a non-covalent target head was connected on the NH group of YZ001011 and YZ001012, and the JAK3 inhibitory activity of YZ001017 was significantly better than those of YZ001011 and YZ001012. The above comparison showed that the covalent target head of the compound applied for by the present invention was very critical for the inhibitory activity against JAK3 kinase. The applicant speculated that the covalent target head could form a covalent action with the Cys909 amino acid of the JAK3 kinase.

Example 137 Kinase Selectivity Experiment

Objective of Experiment

A Mobility shift assay was adopted to detect the compounds to be tested (see list below) for in vitro inhibitory activity against the enzyme activity of other subtypes of the JAK kinase family (JAK1, JAK2, TYK2) to examine the kinase selectivity of the compounds. PF-06651600 was taken as a positive control compound.

Experimental Method the same as that for JAK3 kinase inhibitory activity experiment.

Experimental Results

| Compound number | JAK1 IC50 (nM) | JAK2 IC50 (nM) | TYK2 IC50 (nM) | JAK3 IC50 (nM) |
|---|---|---|---|---|
| YZ001001 | >10000 | >10000 | >10000 | 0.72 |
| YZ001005 | >10000 | >10000 | >10000 | 16 |
| PF-06651600 | >10000 | >10000 | >10000 | 18 |

The data in the table above showed that our compounds had good selectivity for other subtypes of the same JAK family.

Example 138 Cell Viability Experiment

Objective of Experiment

Based on the mechanism of the JAK-STAT pathway, the cytokine IL-15 was adopted to stimulate hPBMC cells, and the downstream STAT5 phosphorylation level was taken as a detection indicator to evaluate the effect of the compound on the JAK-STAT pathway.

Experimental Method

1. Seeding plate for PBMC cell counting: 90 μL of PBMCs were seeded in a 96-well plate (PBMC cell density: 80,000/well).
2. Treatment of compound to be tested: after the cells were seeded on the plate, administration treatment was performed immediately. The drug to be tested was 5 μL/well (with final concentration of 1, 0.5, 0.1, 0.05, 0.01, and 0.005 μM), and the plate was incubated in a 37° C. incubator for 45 min.
3. Stimulation with cytokine IL-15: the cells were stimulated with 5 μL of IL-15 and incubated at 37° C. for 30 min.
4. Protein sample collection: the cells were collected in a centrifuge tube and centrifuged for 5 min. The supernatant was discarded after the centrifuging, and the cells were lysed with 1× Cell Extraction Buffer PTR.
5. p-STAT5 detection: detection was conducted according to the requirements of a ELISA kit.

Experimental results: $IC_{50}$ values of compounds on p-STAT5 under stimulation with IL-15 in PBMCs

| Compound number | IC50 (nM) |
|---|---|
| YZ001052 | 10.74 |
| YZ001065 | 26.27 |
| YZ001075 | 31.73 |
| PF-06651600 | 85.02 |

The data in the table above showed that our compounds had a good inhibitory effect on the JAK3-STATs signaling pathway at a cellular level, and partial compounds showed comparable or lower $IC_{50}$ than positive drugs.

Example 139 In Vivo Exposure Detection in Animals

Objective of Experiment

IG: the exposure level of YZ001054 in the plasma of SD Rats SD tested at an administration dose of 20 mg/kg.

Experimental Method

Preparation and processing of standard curves and quality control samples: the compound stock solution was taken and diluted with 50% methanol and water into standard working solutions containing respective compounds at concentrations of 20, 40, 100, 200, 400, 1,000, 2,000, 4,000, and 10,000 ng/mL respectively and quality control working solutions at concentrations of 60, 600 and 8,000 ng/mL respectively. Each 47.5 μL of blank rat plasma was taken and added with 2.50 μL of a standard curve working solution and a quality control working solution respectively to prepare standard curve samples containing respective compounds at concentrations of 1.00, 2.00, 5.00, 10.00, 20.00, 50.00, 100.00, 200.00 and 500.00 ng/mL and quality control samples with concentrations of 3.00, 30.00 and 400.00 ng/mL. The samples were respectively added with 200 μL of acetonitrile (containing 2 ng/mL of verapamil as an internal standard), vortexed with shaking for 3 min, and then centrifuged at 20,000 rcf and 4° C. for 10 min, and the supernatant was taken for LC-MS/MS analysis.

Preparation and processing of plasma sample to be tested: 50 μL of the plasma sample was taken, added with 200 μL of acetonitrile (containing 2 ng/ml of verapamil as an internal standard), vortexed with shaking for 3 min, and then centrifuged at 20,000 rcf and 4° C. for 10 min, and the was taken for LC-MS/MS analysis.

| Pharmacokinetic parameters | Unit | Average Value |
|---|---|---|
| HL_Lambda_z | hr | 1.4162 |
| Tmax | hr | 4.5 |
| Cmax | ng/mL | 1357.78 |
| AUClast | hr*ng/mL | 1877.52 |
| AUClast_D | hr*kg*ng/mL/mg | 93.88 |
| AUCINF_obs | hr*ng/mL | 1897.55 |
| Vz_F_obs | mL/kg | 34359.46 |
| Cl_F_obs | mL/hr/kg | 14108.42 |
| MRTINF_obs | hr | 1.9469 |

Experimental Results

From the data in the table above, it could be seen that our compounds had a certain level of exposure in vivo and could be developed for oral administration.

Example 140 Immunosuppressive Effect of Compounds on Delayed Type Hypersensitivity (DTH) in Mice Objective of Experiment The immunosuppressive activity of YZ001052, YZ001054, YZ001065, and YZ001085 in a SRBC mouse model was tested. PF-06651600 was used as a positive control compound.

Experimental Method

Drug preparation: the compound was weighed and added with a 0.5% CMC-Na solution to prepare a drug suspension (with an administration dose of 10 mg/mL).

Induction of delayed type hypersensitivity (DTH) and administration: 30 male Balb/c mice were weighed and randomly divided into 6 groups according to body weight, with 5 mice in each group. The experimental period lasted for 7 days in total. On day 0, the mice were subcutaneously injected with sheep red blood cells (SRBCs) for sensitization. From day 0, the mice were administrated with 100 mg/kg by gavage (once a day) until day 6. On day 6, SRBCs were injected into the right hind foot pad of the mice for excitation. On day 7 of the experiment, measurements were conducted, photographs were taken, and the experiment was ended.

Pharmacodynamic detection indicators of disease models: the detection and observation indicators were the degree of redness and swelling and detected thicknesses of paw pads of the mice in the model group as induced by SRBC. The thickness of the right paw was measured as the baseline before the SRBC injection excitation on day 6. At the end of the experiment 0, the thickness of the right paw was measured again, and the difference in thickness of the paw before and after the second injection was calculated.

Statistical processing: experimental data was expressed as mean±standard deviation (Mean±SD). All data was statistically analyzed using a T-test. $P<0.05$ was considered to be statistically different. The results were shown in FIG. 1.

Experimental Results

It could be seen from FIG. 1 that, the thicknesses of the right paws of the mice after SRBC induction (the model group) was increased significantly, and the thicknesses of the right paws of the mice after treatment with drugs (including the compounds YZ001052, YZ001054, YZ001065, and YZ001085) were improved to varying degrees, indicating that the compounds YZ001052, YZ001054, YZ001065 and YZ001085 had significant immunosuppressive effects on SRBC-induced delayed type hypersensitivity in the mice, and their effects were non-inferior to that of PF-06651600.

Example 142: Immunosuppressive Effect of Compounds on Collagen-Induced Mouse Arthritis Model 1. Construction of Collagen-Induced Mouse Arthritis Model (mCIA)

Objective of Experiment: to test the immunosuppressive activity of YZ001052 in a mCIA model. PF-06651600 was used as a positive control compound.

Experimental method: 32 female DBA/1J mice were randomly divided into 4 groups, which were set as a blank control group, a model group, a model+YZ001052 administration group, and a model+PF-06651600 administration group. After successful arthritis modeling, YZ001052 or PF-06651600 was given once a day at 50 mg/kg for drug intervention. Complete and incomplete Freund's adjuvants were mixed with a chicken type II collagen solution in equal proportions to form an emulsifier. Except for the blank control group, on Day 0, a mixture of a complete Freund's adjuvant and the chicken type II collagen solution was subcutaneously injected into the tail roots and thigh roots of the mice, with 100 μL being injected subcutaneously at the tail root of each mouse; and 50 μL being injected subcutaneously at each of the two thigh roots of each mouse (primary immunization). On day 21, the mice were subcutaneously injected with 200 μL of a mixture of an incomplete Freund's adjuvant and the chicken type II collagen solution as a booster injection (second immunization). Arthritis was judged to have occurred if at least one limb had a clinical score of >2 points. Measurement of paw thickness: the thicknesses of the left and right hind feet of the mice were measured with a vernier caliper to serve as the paw swelling degree and recorded, and the detection frequency was once every 3 days.

Figure 2:
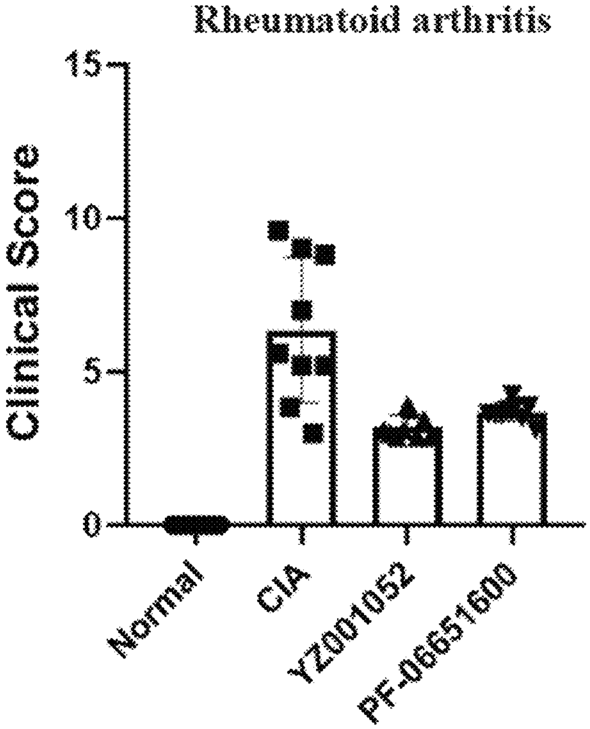
FIG. 2 shows the immunosuppressive effect of the compound on a collagen-induced mouse arthritis model.

Experimental results: it could be seen from FIG. 2 that after the second immunization, the inflammation in the paws of the mice in the model group continued to exacerbate, the swelling gradually spread to the entire paw, and the arthritis scores increased significantly on day 16. After treatment with YZ001052 or PF-06651600, the swelling of the paws of the CIA mice was improved to varying degrees, and the arthritis scores were significantly reduced (compared to the model group).

Consistent with the arthritis scores, the mice in the model group showed significant swelling in their paws, and after treatment with YZ001052 or PF-06651600, the swelling of the paws of the mice was improved to varying degrees. The aforementioned results indicated that YZ001052 or PF-06651600 could improve the symptoms of rheumatoid arthritis.

Example 143: The Immunosuppressive Effect of the Compound on a Dextran Sulfate Sodium (DSS)-Induced Mouse Inflammatory Bowel Disease Model Objective of Experiment: to test the immunosuppressive activity of YZ001052 in a DSS-induced mouse inflammatory bowel disease model. PF-06651600 was used as a positive control compound.

Experimental method: 32 female C57BL/6 mice were randomly divided into 4 groups, namely a blank control group, a model group, a model+YZ001052 administration group, and a model+PF-06651600 administration group. When administered simultaneously at the beginning of modeling, the administration dosage of YZ001052 and PF-06651600 was 50 mg/kg once a day. 50 g of DSS was weighed, added with 1,000 mL of sterile water, formulated into a 5% DSS solution, and filtered with a 0.22 μm filter membrane. From day 0, the blank group was given drinking water without DSS, and the other experimental groups were given drinking water containing 5% DSS. All mice were sacrificed on day 8. After the experiment was ended, the colorectum was collected, and photographed, and its length was measured for statistical analysis.

Figure 3:
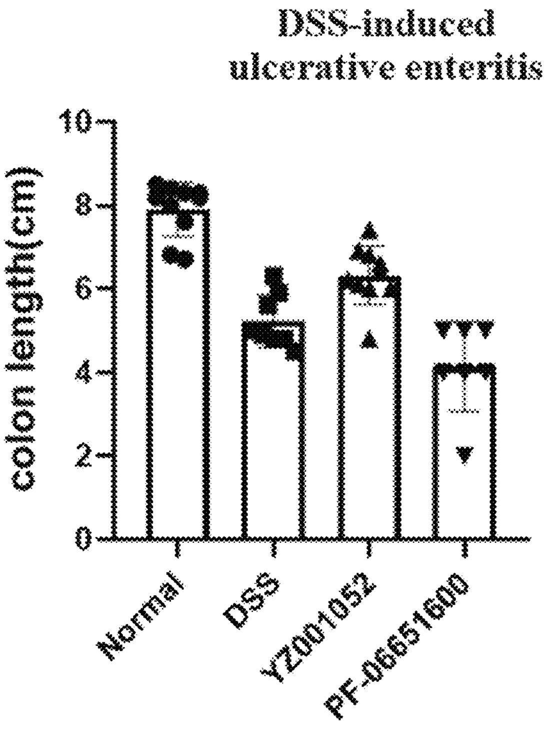
FIG. 3 shows the immunosuppressive effect of the compound on a dextran sulfate sodium (DSS)-induced mouse inflammatory bowel disease model.

Experimental results: as shown in FIG. 3, compared with the normal control group, the length of the colorectum of the mice in the model group was significantly shortened, indicating that the colorectum of the mice with inflammatory bowel disease was severely injured. Compared with the mice in the model group, the length of the colorectum of the mice in the group treated with YZ001052 was significantly increased, indicating that treatment with YZ001052 could alleviate colorectal injury in the mice with inflammatory bowel disease, and the result was better than that of PF-06651600.

Example 144 Immunosuppressive Effect of Compound on Radiation-Induced Lung Injury Mouse Model 1. Construction of Mouse Model of Acute Radiation-Induced Lung Injury (1) Grouping of Animals and Administration 18 female C57BL/6 mice were randomly divided into 3 groups, namely a blank control group, a group treated with irradiation alone, and a group intervened with irradiation+ drug YZ001052 (30 mg/kg q.d), with 6 mice in each group.

(2) Modeling Method

The mice were anesthetized by intraperitoneal injection of 1% pentobarbital sodium, and were subjected to a single whole lung irradiation at 22.5 Gy, with 220 KV of X-rays by using a small animal radiation research platform (SARRP). After the irradiation was completed, the mice were fed routinely.

2. Indicator Detection 3 weeks after modeling, the mice were anesthetized and dissected. The lung tissue was exposed, the left lung was ligated, an open tracheotomy was performed, the lung was lavaged with cold PBS, and the bronchoalveolar lavage fluid (BALF) was collected and subjected to refrigerated centrifugation at 4° C.

Figure 4:
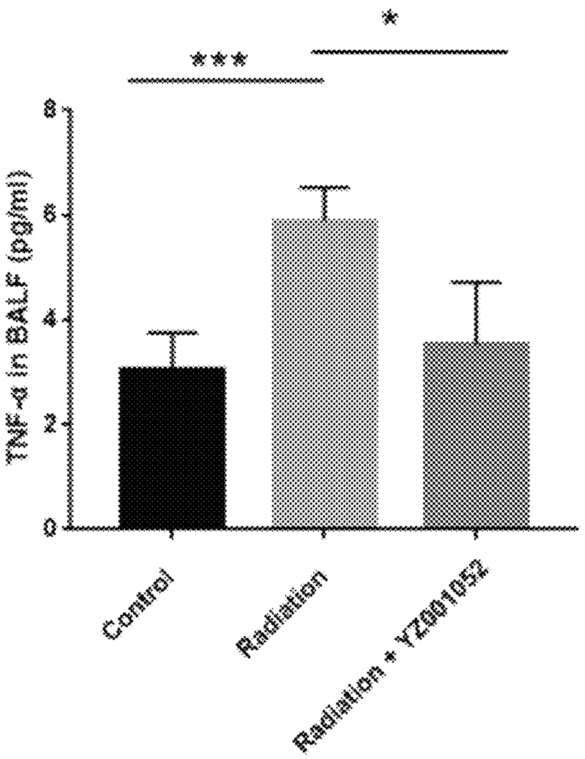
FIG. 4 shows the inhibitory effect of the compound on the TNF-α level in mice with acute radiation-induced lung injury.

The supernatant was collected, and detected for the content of the inflammatory factor TNF-α by ELISA. As shown in FIG. 4, after induction with irradiation, the TNF-α level in the alveolar lavage fluid of the mice in the model group was increased significantly. The drug YZ001052 had a good inhibitory effect on the TNF-α level.

Figure 5:
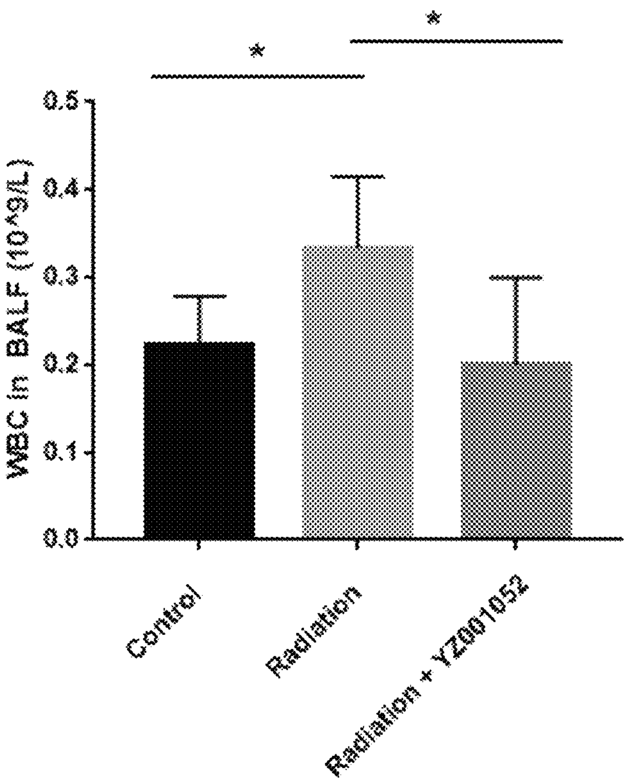
FIG. 5 shows that the compound reduces the number of inflammatory cell infiltrates in the lungs of mice with acute radiation-induced lung injury.

The cell pellet of the alveolar lavage fluid was resuspended in 200 μL PBS and used for counting of white blood cells (WBCs). As shown in FIG. 5, after induction with irradiation, the number of white blood cells in the alveolar lavage fluid of the mice in the model group was increased significantly. The drug YZ001052 could significantly reduce the number of inflammatory cell infiltrates in the lungs of mice caused by radiation.

What is claimed is:

1. An aromatic heterocyclic compound having a structure of general formula II, or an optical isomer thereof, a deuterated compound thereof or a pharmaceutically acceptable salt thereof:

II

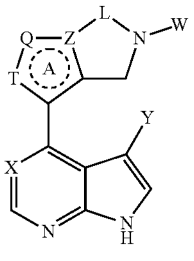

wherein:

the ring A is a five-membered heterocyclic ring containing 2 double bonds; Z is N or C, Q is N or $NR_7$, T is CH or N or $NR_8$, and when Z and T are N at the same time, Q is N; wherein $R_7$ and $R_8$ are independently hydrogen, deuterated methyl, $C_1$-$C_4$ alkanoyl, $C_1$-$C_4$ alkyl or $C_4$-$C_6$ heterocycloalkyl respectively, wherein the $C_4$-$C_6$ heterocycloalkyl contains 1 heteroatom, and the heteroatom is an oxygen atom;

L is selected from

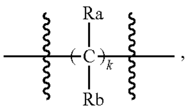,
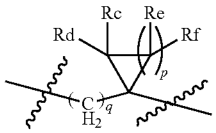
or
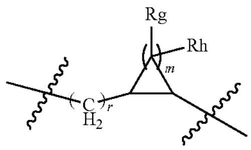, wherein $R_a$, $R_b$, $R_c$, $R_d$, $R_e$, $R_f$, $R_g$, and $R_h$ are each independently selected from hydrogen, $C_1$-$C_4$ alkyl, and monosubstituted $C_1$-$C_4$ alkyl, the substituent in the "monosubstituted $C_1$-$C_4$ alkyl" is selected from $C_1$-$C_3$ alkylthio, $C_1$-$C_3$ alkanesulfonyl, and cyano; k is an integer of 1-4, q is an integer of 0-3, r is an integer of 0-2, p is 1 or 2, and m is 3 or 4;

W is selected from

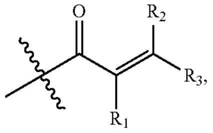
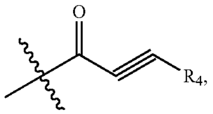
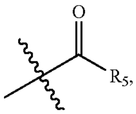
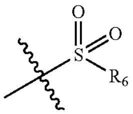

or a nitrile group; wherein $R_1$ and $R_2$ are each independently selected from hydrogen, deuterium, halogen, cyano, $C_1$-$C_4$ alkyl, $R_3$ is selected from hydrogen, deuterium, halogen, cyano, $C_1$-$C_4$alkyl, halomethyl,

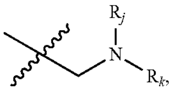
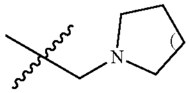
or
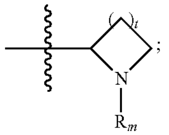;

n and t are each independently selected from an integer of 1-3; $R_j$, $R_k$ and $R_m$ are each independently selected from hydrogen, methyl or ethyl; $R_4$ is selected from hydrogen or methyl; $R_5$ is halomethyl; and $R_6$ represents vinyl;

X is selected from N or CH; and Y is selected from hydrogen or $C_1$-$C_4$ alkanoyl.

2. The aromatic heterocyclic compound according to claim 1, wherein the compound has a structure of general formula III-1, III-2, III-3 or III-4, or an optical isomer thereof, a deuterated compound thereof or a pharmaceutically acceptable salt thereof:

III-1

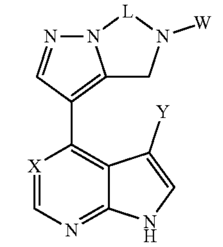

III-2

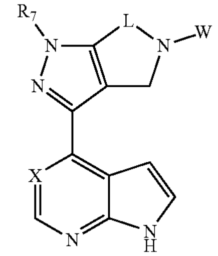

III-3

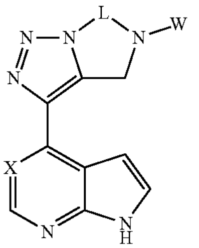

III-4

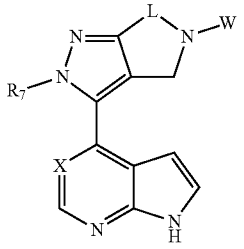

L is selected from

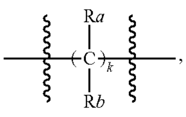

,

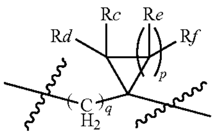

or

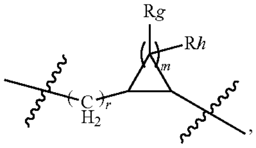

, wherein $R_a$, $R_b$, $R_c$, $R_d$, $R_e$, $R_f$, $R_g$, and Rn are each independently selected from hydrogen, $C_1$-$C_4$ alkyl, and monosubstituted $C_1$-$C_4$ alkyl, the substituent in the monosubstituted $C_1$-$C_4$ alkyl is selected from methylthio, methanesulfonyl, and cyano; k is an integer of 1-4, q is an integer of 0-3, r is an integer of 0-2, p is 1, and m is 3 or 4;

W is selected from

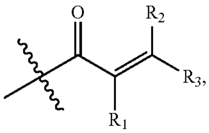

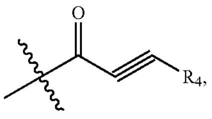

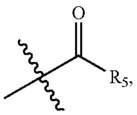

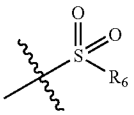

or a nitrile group; wherein $R_1$ is hydrogen, deuterium, halogen, cyano, or methyl, $R_2$ is hydrogen, deuterium, cyano or methyl, $R_3$ is hydrogen, deuterium, halogen, cyano, methyl, trifluoromethyl,

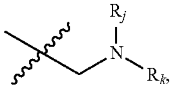

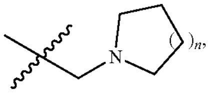

or

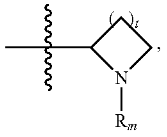

n and t are 2, $R_j$, $R_k$, and $R_m$ are methyl; $R_4$ is selected from hydrogen or methyl; $R_5$ is halomethyl; and $R_6$ represents vinyl;

X is selected from N or CH; and Y is selected from hydrogen or acetyl.

3. The aromatic heterocyclic compound according to claim 2, wherein: in the general formula, L is selected from

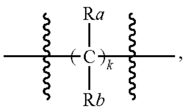

,

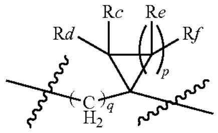

or

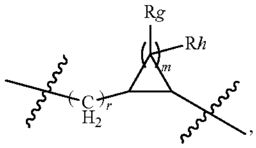

, wherein: $R_a$ and $R_b$ are each independently selected from H, methyl, isopropyl, methylthio-substituted ethyl, and methanesulfonylethyl; $R_c$, $R_d$, $R_e$, and $R_f$ are each independently selected from H and methyl; $R_g$ and $R_h$ are each independently selected from H and methyl; k is 1, 2, 3, or 4, q is 1, r is 0, p is 1, and m is 3 or 4;

$R_7$ and $R_8$ are independently hydrogen, methyl, isopropyl, acetyl, deuterated methyl, $C_4$-$C_6$ heterocycloalkyl respectively, wherein the $C_4$-$C_6$ heterocycloalkyl contains 1 heteroatom, and the heteroatom is an oxygen atom.

4. The aromatic heterocyclic compound according to claim 1, wherein the compound is selected from the following compounds:

YZ001001
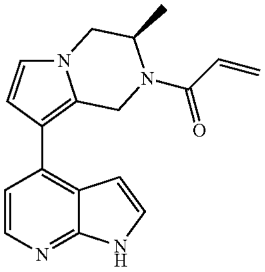
YZ001002
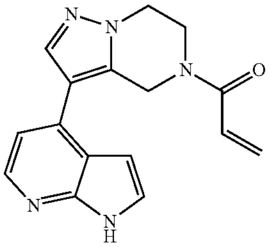
YZ001004
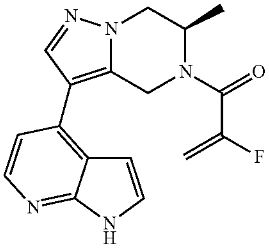
YZ001005
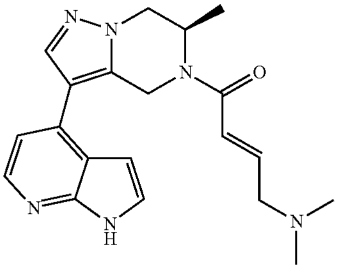
YZ001006
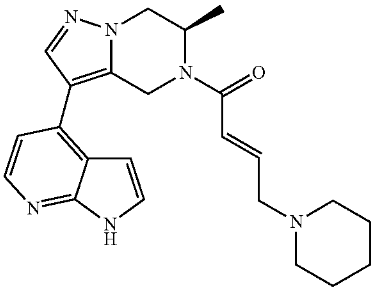
YZ001007
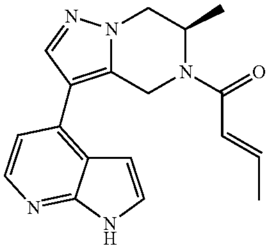
-continued
YZ001008
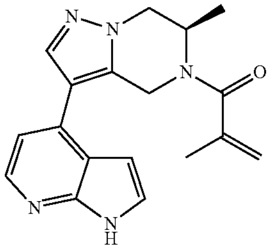
YZ001009
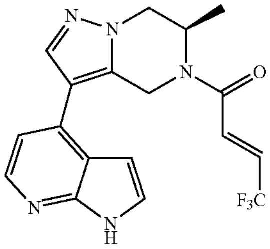
YZ001010
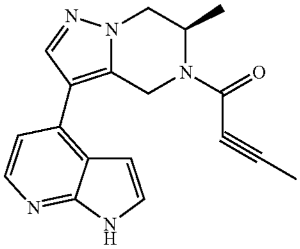
YZ001013
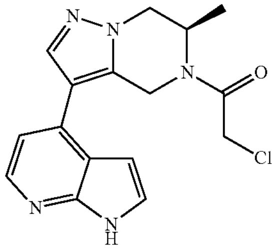
YZ001016
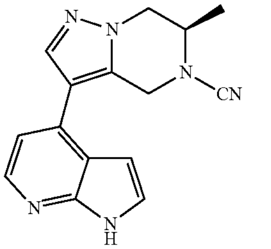
YZ001017
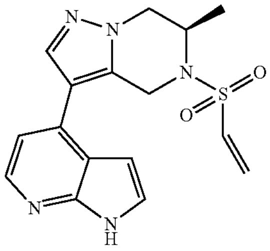

-continued
YZ001018
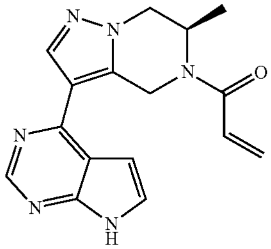
YZ001019
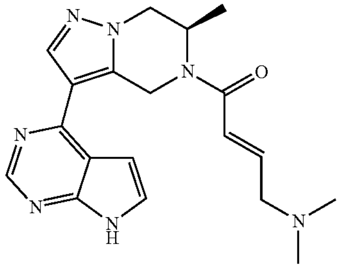
YZ001020
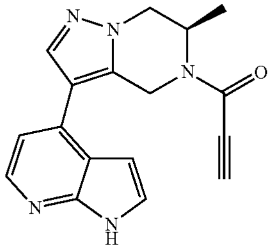
YZ001021
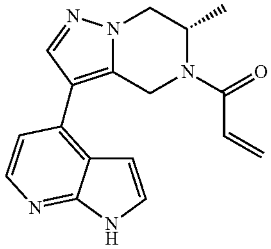
YZ001022
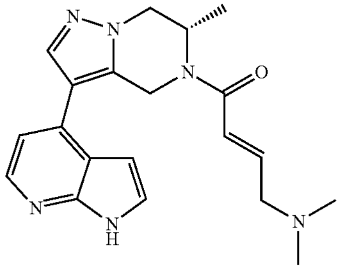
YZ001023
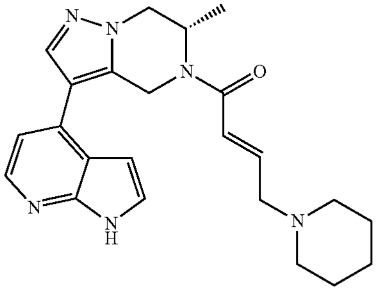
-continued
YZ001024
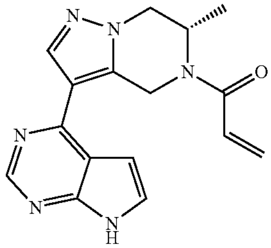
YZ001025
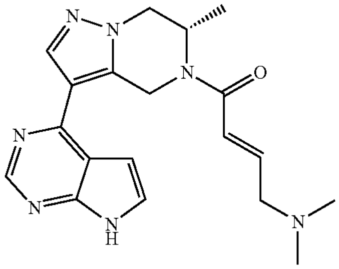
YZ001026
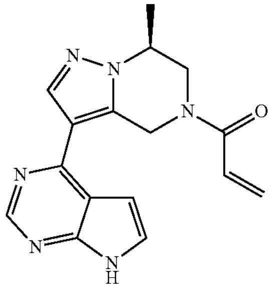
YZ001027
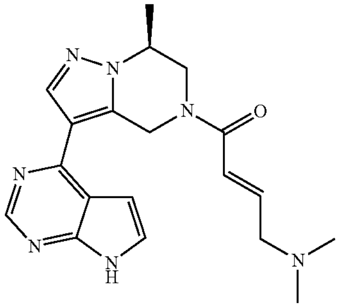
YZ001028
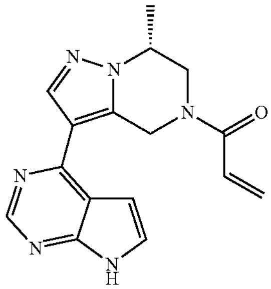

-continued
YZ001029
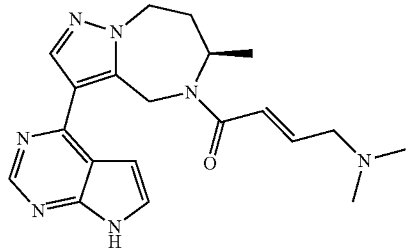
YZ001030
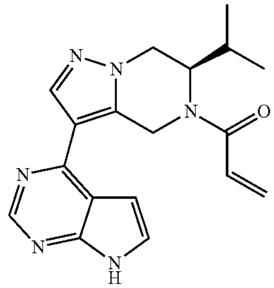
YZ001031
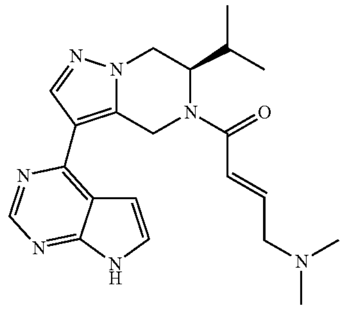
YZ001032
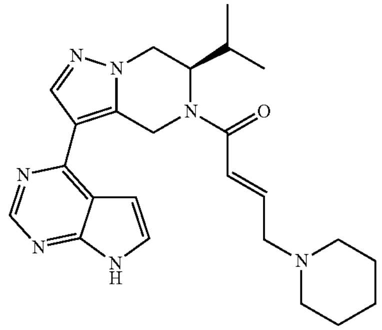
YZ001033
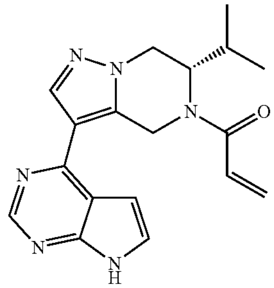
-continued
YZ001034
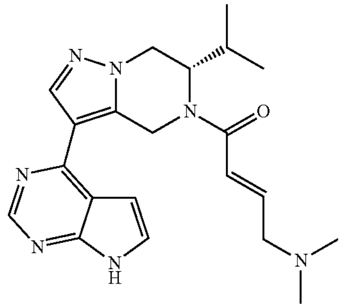
YZ001035
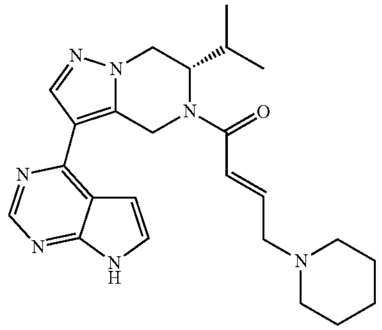
YZ001039
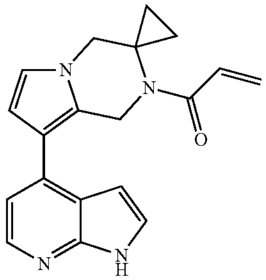
YZ001045
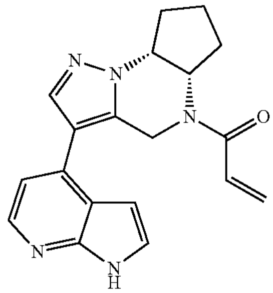
YZ001047
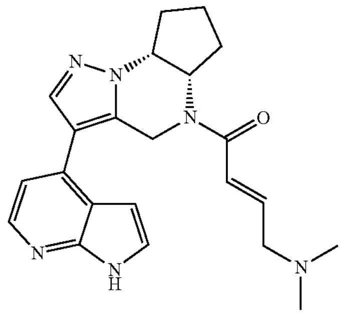

-continued
YZ001048
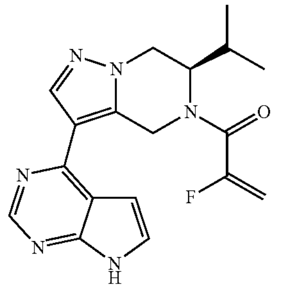
YZ001049
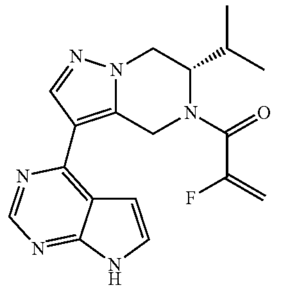
YZ001050
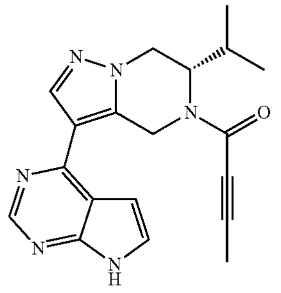
YZ001051
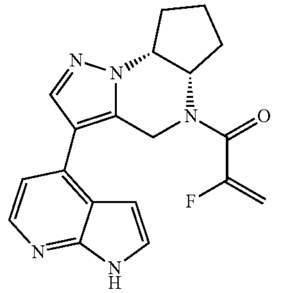
YZ001052
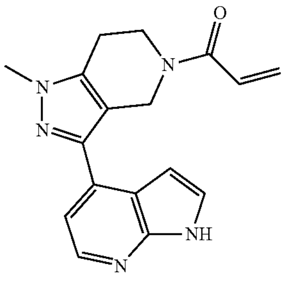
-continued
YZ001053
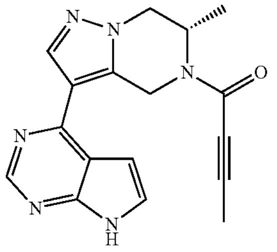
YZ001054
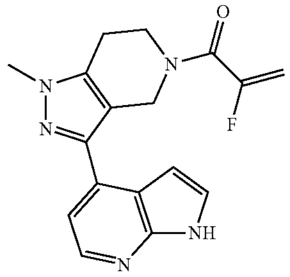
YZ001055
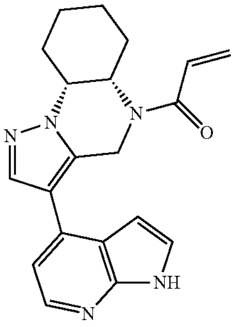
YZ001056
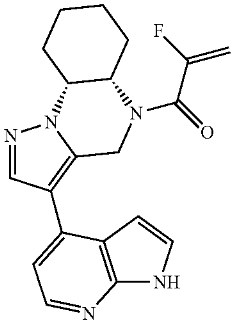
YZ001057
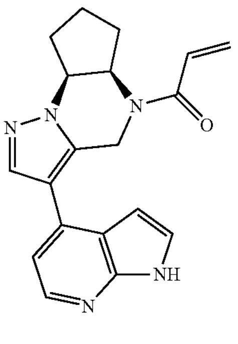

-continued
YZ001058
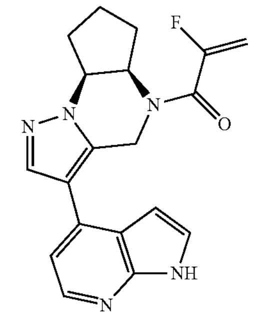
YZ001059
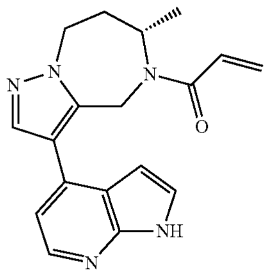
YZ001060
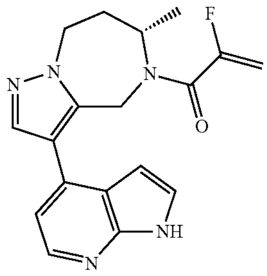
YZ001063
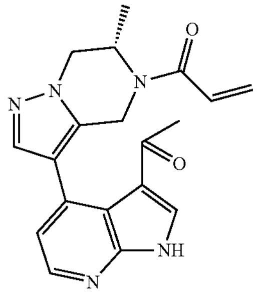
YZ001064
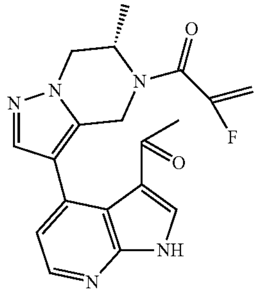
-continued
YZ001065
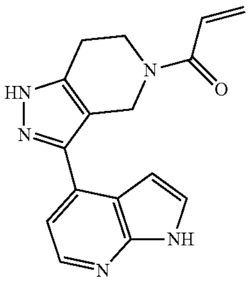
YZ001066
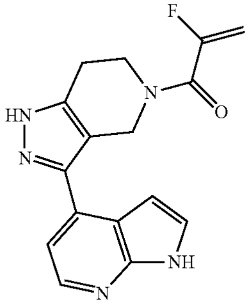
YZ001067
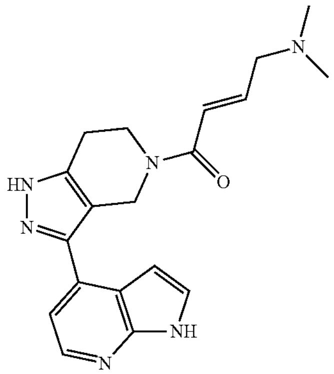
YZ001068
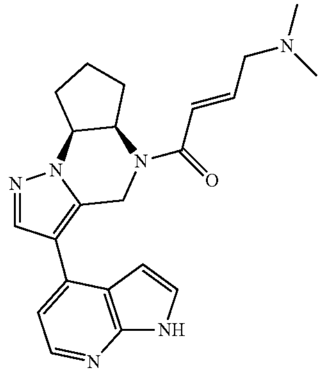
YZ001069
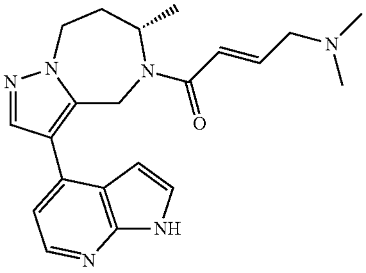

-continued
YZ001070
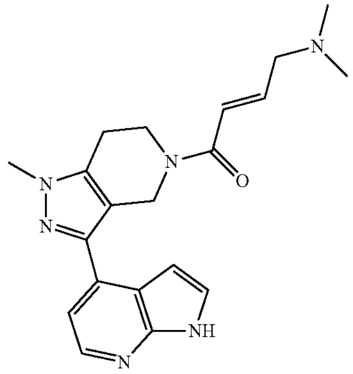
YZ001071
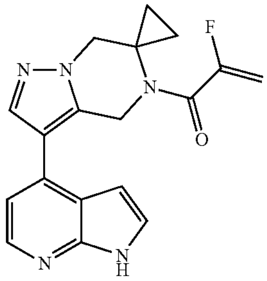
YZ001072
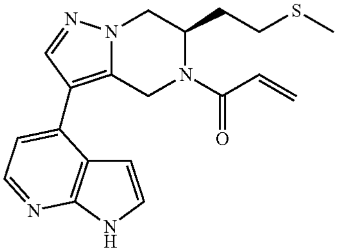
YZ001073
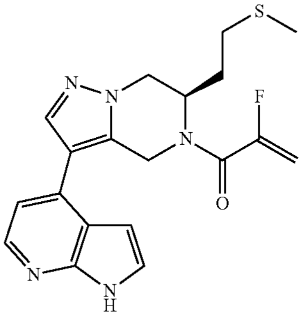
YZ001074
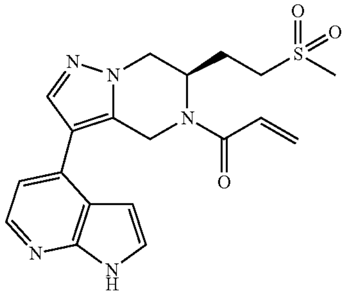
-continued
YZ001075
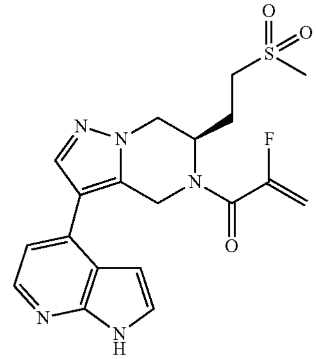
YZ001076
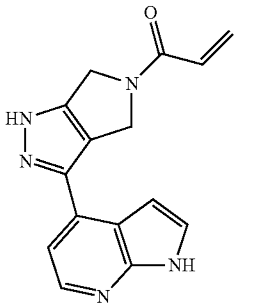
YZ001077
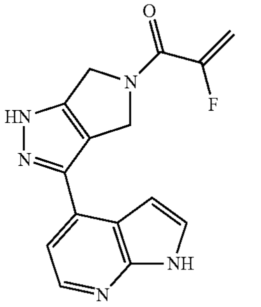
YZ001083
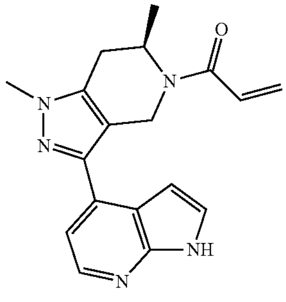
YZ001084
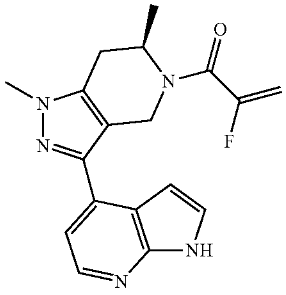

-continued
YZ001085
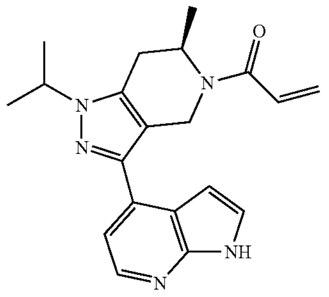
YZ001086
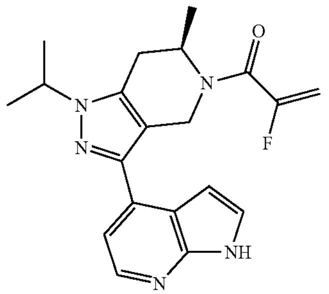
YZ001087
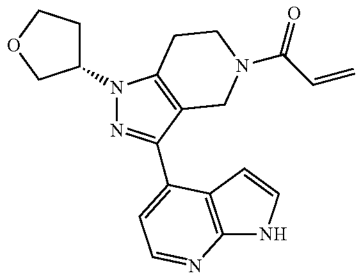
YZ001088
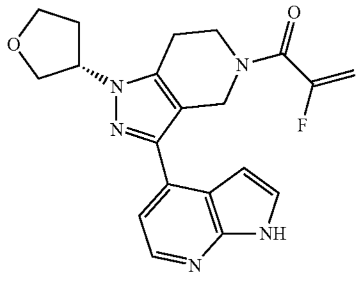
YZ001091
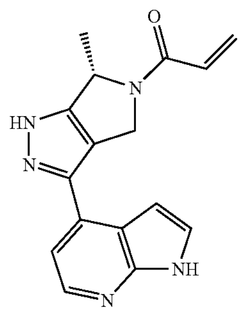
-continued
YZ001093
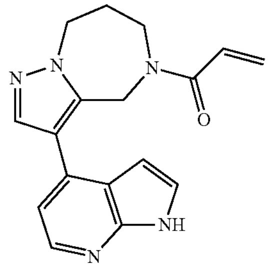
YZ001094
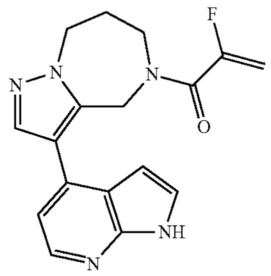
YZ001095
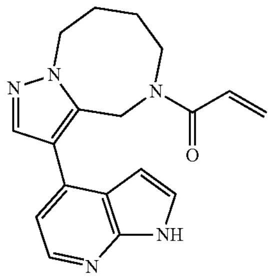
YZ001096
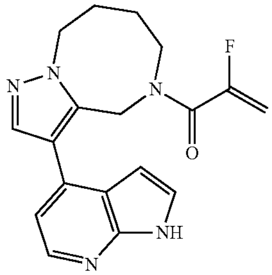
YZ001099
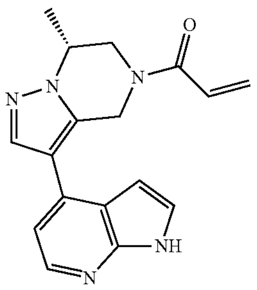

-continued

YZ001100

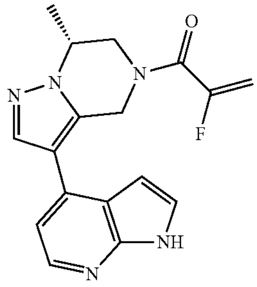

YZ001103

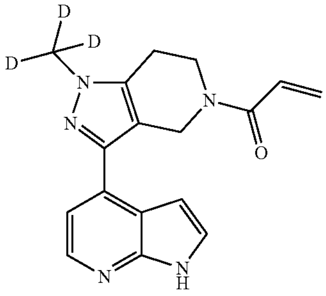

YZ001104

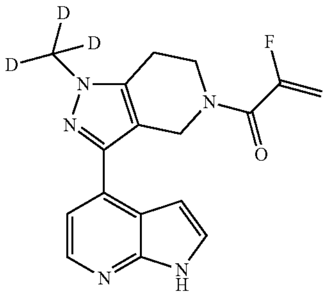

YZ001107

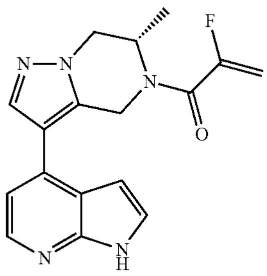

YZ001108

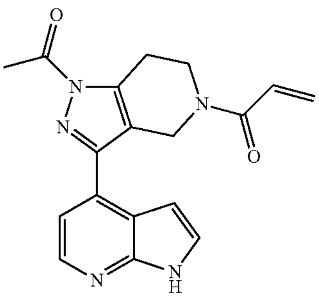

-continued

YZ001109

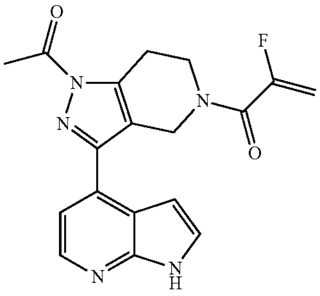

YZ001115

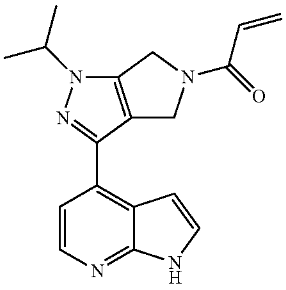

YZ001117

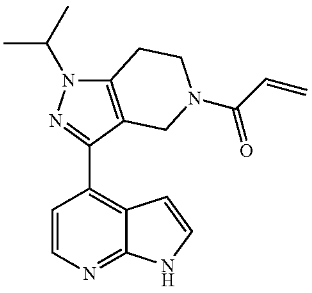

YZ001118

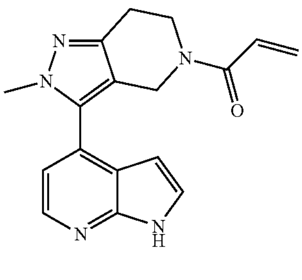

, or an optical isomer thereof, a deuterated compound thereof or a pharmaceutically acceptable salt thereof.

5. A pharmaceutical composition comprising a compound with a structure represented by general formula II, an optical isomer thereof, a deuterated compound thereof or a pharmaceutically acceptable salt thereof:

II

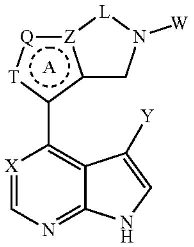

wherein:

the ring A is a five-membered heterocyclic ring containing 2 double bonds; Z is N or C, Q is N or $NR_7$, Tis CH or N or $NR_8$, and when Z and T are N at the same time, Q is N; wherein $R_7$ and $R_8$ are independently hydrogen, deuterated methyl, $C_1$-$C_4$ alkanoyl, $C_1$-$C_4$ alkyl or $C_4$-$C_6$ heterocycloalkyl respectively, wherein the $C_4$-$C_6$ heterocycloalkyl contains 1 heteroatom, and the heteroatom is an oxygen atom;

L is selected from

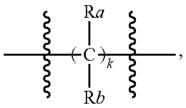

,

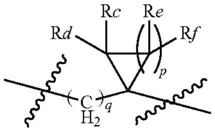

or

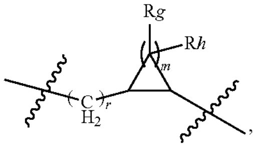

, wherein $R_a$, $R_b$, $R_c$, $R_d$, $R_e$, $R_f$, $R_e$, and Rn are each independently selected from hydrogen, $C_1$-$C_4$ alkyl, and monosubstituted $C_1$-$C_4$ alkyl, the substituent in the "monosubstituted $C_1$-$C_4$ alkyl" is selected from $C_1$-$C_3$ alkylthio, $C_1$-$C_3$ alkanesulfonyl, and cyano; k is an integer of 1-4, q is an integer of 0-3, r is an integer of 0-2, p is 1 or 2, and m is 3 or 4;

W is selected from

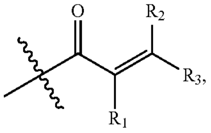

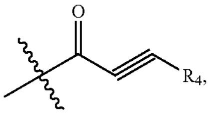

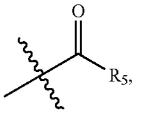

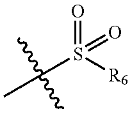

or a nitrile group; wherein $R_1$ and $R_2$ are each independently selected from hydrogen, deuterium, halogen, cyano, $C_1$-$C_4$ alkyl, $R_3$ is selected from hydrogen, deuterium, halogen, cyano, $C_1$-$C_4$alkyl, halomethyl,

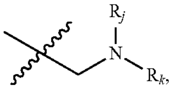

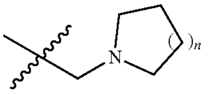

or

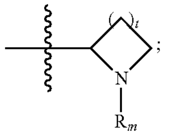

n and t are each independently selected from an integer of 1-3; $R_j$, $R_k$ and $R_m$ are each independently selected from hydrogen, methyl or ethyl; $R_4$ is selected from hydrogen or methyl; $R_5$ is halomethyl; and $R_6$ represents vinyl;

X is selected from N or CH; and Y is selected from hydrogen or $C_1$-$C_4$ alkanoyl.

* * * * *